United States Patent
Zhou

(10) Patent No.: US 7,193,044 B1
(45) Date of Patent: Mar. 20, 2007

(54) COMPOUNDS AND METHODS FOR REGULATING APOPTOSIS, AND METHODS OF MAKING AND SCREENING FOR COMPOUNDS THAT REGULATE APOPTOSIS

(75) Inventor: Xiao-Mai Zhou, Brookline, MA (US)

(73) Assignee: Immunogen, Inc., Cambridge, MA (US)

( * ) Notice: Subject to any disclaimer, the term of this patent is extended or adjusted under 35 U.S.C. 154(b) by 1104 days.

(21) Appl. No.: 09/580,523

(22) Filed: May 30, 2000

(51) Int. Cl.
*C07K 14/00* (2006.01)

(52) U.S. Cl. .................. 530/350; 530/300; 530/402; 514/2; 435/7.1

(58) Field of Classification Search ............. 530/350, 530/300, 402; 536/23.1; 514/2; 435/7.1
See application file for complete search history.

(56) References Cited

U.S. PATENT DOCUMENTS 5,622,852 A * 4/1997 Korsmeyer ................ 435/325
5,965,703 A * 10/1999 Horne et al. ............... 530/350

OTHER PUBLICATIONS

Letai, A et al, 2002, Cancer Cell, 2: 183-192.*
Drexler et al. Leukemia and Lymphoma, 1993, 9:1-25.*
Embleton et al. Immunol Ser, 1984, 23:181-207.*
Hsu. in: Tissue Culture Methods and Applications, Kruse and Patterson, Eds, 1973, Academic Press, NY, see abstract, p. 764.*
Freshney. Culture of Animal Cells, A Manual of Basic Technique, Alan R. Liss, Inc., 1983, New York, p. 4.*
Dermer. Bio/Technology, 1994, 12:320.*
MPSRCH search report, 2001, 09-580523-1b.rai, pp. 1-2.*
Bowie et al (Science, 1990, 257 : 1306-1310).*
Burgess et al, (Journal of Cell Biology, 1990, 11: 2129-2138).*
Lazar et al. Molecular and Cell Biology, 1988, 8: 1247-1252.*
Tao. et al. The Journal of Immunology, 1989, 143(8): 2595-2601, and Gillies et al. Human Antibodies and Hybridomas, 1990, 1(1): 47-54.*
Gillies et al. Human Antibodies and Hybridomas, 1990, 1(1): 47-54.*
Bowie et al (Science, 1990, 257 : 1306-1310).*
Yin XM et al, 1994, Nature, 369: 321-323.*
Straub P et al, 1993, J Biol Chem 268(29): 21997-20003.*
Kouklis PD et al, 1993, J Cell Science, 106(pt 3): 919-28.*
Kelelar et al, 1997, Mol Cell Biol, 17(12): 7040-7046.*
Zha et al, 1997, JBC, 272(39): 24101-24104.*
Moreau et al, 2003 (JBC, 278 (21): 19426-19435).*
MEDLINE Database, Accession #054920, Jun. 1, 1998.
O'Connor et al., EMBO Journal, Jan. 15, 1998, vol. 17, pp. 384-395.
MEDLINE Database, Accession #P55472, Nov. 1, 1997.
Ottilie et al, *J. of Biol. Chem.*, 272(49):30866-30872 (1997).
Harada et al, *Mol. Cell*, 3(4):413-422 (1999).
Datta et al, *Cell*, 91(2):231-241 (1997).
Zha et al, *Cell*, 87(4):619-628 (1996).
Datta et al, *Mol. Cell*, 6(1):41-51 (2000).
Zhou et al, *J. of Biol. Chem.*, 275(32):25046-25051 (2000).
Ottilie, S. et al.: "Dimerization properties of human BAD. Identification of a BH-3 domain and analysis of its binding to mutant BCL-2 and BCL-XL proteins.", The Journal of Biological Chemistry, U.S., Dec. 5, 1997, vol. 272, No. 49, pp. 30866-30872.
Harada, H. et al.: "Phosphorylation and inactivation of BAD by mitochondria-anchored protein kinase A.", Molecular Cell, vol. 3, No. 4, Apr. 1999, pp. 413-422.
Datta, S. R., et al.: "Akt phosphorylation of BAD couples survival signals to the cell-intrinsic death machinery", Cell, vol. 91, No. 2, 1997, pp. 231-241.
Zha, J. et al.: "Serine phosphorylation of death agonist BAD in response to survival factor results in binding to 14-3-3 not BCL-$X_L$", Cell, vol. 87, No. 4, 1996, pp. 619-628.

* cited by examiner

*Primary Examiner*—Jeffrey Siew
*Assistant Examiner*—Minh-Tam Davis

(57) ABSTRACT

Novel forms of mutant BAD polypeptides or fragments thereof having amino acid substitutions for serine-155 are provided along with their encoding polynucleotides. Also disclosed are methods for preparation of the mutant BAD polypeptides, methods for screening candidate compounds and drugs for activity that promotes cell survival or apoptosis, methods for screening candidate compounds and drugs for phosphatase activity capable of dephosphorylating BAD, methods for screening candidate compounds and drugs for kinase activity capable of phosphorylating BAD, methods for screening candidate compounds and drugs for activity that promotes phosphorylation of BAD, anti-BAD antibodies, and methods for inhibiting and inducing apoptosis.

16 Claims, 23 Drawing Sheets anti-HA Ab probe anti-HA Ab probe anti-HA Ab probe

| GST-BAD: | wildtype | S112A | S136A | S155A | S112A/ S136A | S112A/ S136A/ S155A |

1 2 3 4 5 6
$^{32}$P-autoradiograph 1 2 3 4 5 6
anti-BAD Ab probe anti-BAD Ab probe anti-BAD Ab probe anti-BAD Ab probe

COMPOUNDS AND METHODS FOR REGULATING APOPTOSIS, AND METHODS OF MAKING AND SCREENING FOR COMPOUNDS THAT REGULATE APOPTOSIS

FIELD OF THE INVENTION

The present invention relates generally to the field of cell physiology, and more particularly, to apoptosis or programmed cell death, a process whereby developmental or environmental stimuli activate a genetically programmed cascade of events that results in cell death. Specifically, the invention relates to the regulation of apoptosis, including the regulation of apoptosis resulting in cell survival, compounds therefor, and methods of making and screening for such compounds. More specifically, the invention relates to mutants of Bcl-$X_L$/Bcl-2 Associated Cell Death Regulator polypeptides ("BAD"), methods of making such mutants, and methods of screening for compounds that promote, induce, inhibit, or modulate apoptosis, or promote, induce, inhibit, or modulate cell survival.

BACKGROUND OF THE INVENTION

Throughout the life of an organism, there is a constant progression of cellular development. New cells are continually being produced, through such mechanisms as mitosis and meiosis, to replace old or damaged cells that are targeted for destruction due to disease, injury, extracellular cues and internal instructions. This cellular life-death balance is a critical feature not only in normal animal development, but also in pathogenesis. Indeed, diseases such as cancer and autoimmune disorders are associated with decreased cell death, whereas AIDS and neurodegenerative disorders are associated with increased cell death (Thompson, 1995).

Programmed cell death, or apoptosis, is one manner in which cells that are no longer needed or that no longer function normally can be eliminated. Apoptosis is believed to be a process actively regulated by the environment in which cells live. This process is critical to the normal development of all multicellular organisms and to the maintenance of homeostasis within such organisms (Raff, 1992). Moreover, apoptosis is vital in the defense against viral infection and in preventing the development of carcinogenesis. Amongst multicellular organisms, the apoptotic pathway leading to cell death is highly conserved (Hengartner, 1994).

Many molecules that regulate the apoptotic pathway have been identified, including both positive regulators (agonists) and negative regulators (antagonists). Such regulators are often members of the same family of polypeptides, and can have roles important in the extracellular, cell surface, and/or intracellular steps of the apoptotic pathway (Oltvai and Korsmeyer, 1994). One such family of polypeptides, constituting an intracellular checkpoint in the apoptotic pathway, is the Bcl-2 family of polypeptides ("Bcl-2 family"). This important family of apoptotic regulators can be divided into two classes: those that suppress cell death (apoptotic antagonists) (e.g., Bcl-2, Bcl-$X_L$, MCL-1, and A1) and those that appear to promote apoptosis (apoptotic agonists) (e.g., BAX, BAK, Bcl-$X_S$, and BAD). The first member of the Bcl-2 family to be identified was Bcl-2, a cell death inhibitor encoded by the bcl-2 proto-oncogene, initially isolated from cells of a follicular lymphoma (Bakhshi et al., 1985; Tsujimoto et al., 1985; Cleary and Sklar, 1985). Bcl-2 is a 26 kD integral membrane polypeptide localized to the mitochondria that extends or promotes the survival of many different cell types by inhibiting apoptosis induced by a variety of cell death-inducing stimuli (Korsmeyer, 1992).

The Bcl-2 family contains members that are structurally and functionally related to Bcl-2, and is defined by polypeptides having amino acid sequence homology to one or more of four conserved motifs, termed Bcl-homology (BH1, BH2, BH3, and BH4) domains (for reviews see Reed, 1997 and Chittenden, 1998). The Bcl-homology domains have been shown to be important in the formation of homodimers and heterodimers, both among and between Bcl-2 family members.

The functional characteristics of these proteins vary, depending on their dimerization partners (Yin et al., 1994; Boyd et al., 1995; Chittenden et al., 1995; Farrow and Brown, 1996). The dimerization status of the proteins has been shown to depend on the intracellular concentrations of the particular family members, and is directly related to whether a cell will respond to an apoptotic signal (Oltvai and Korsmeyer, 1994). Moreover, the formation of dimers between cell death promoters and cell death inhibitors is competitive. For example, both Bcl-2 and Bcl-$X_L$ enhance cellular survival, while BAD and BAX promote cell death (Oltvai et al., 1993). However, when BAD is overexpressed, it counters the death inhibitory activity of Bcl-$X_L$, and to a lesser extent Bcl-2, by the formation of heterodimers. It is thought that BAD competes with BAX for binding to Bcl-$X_L$. Therefore, when the intracellular levels of BAD increase, there is a sequestration of Bcl-$X_L$ in BAD:Bcl-$X_L$ heterodimers, and a concomitant increase in the amount of free BAX present in the cell as BAX monomers or BAX:BAX homodimers. The increased levels of BAX monomer and homodimers, in turn, promote cellular susceptibility to apoptosis (Korsmeyer, U.S. Pat. No. 5,856,445).

BAD (Bcl-$X_L$/Bcl-2 Associated Cell Death Regulator polypeptide) is a cell death promoter distantly related to Bcl-2. It has been sequenced and shown to share identity with Bcl-2 only within the BH3 domain. BAD is an unique pro-apoptotic member of the Bcl-2 family in that its function is regulated by phosphorylation (Yang et al., 1995), suggesting an important connection between extracellular apoptosis regulatory agents, intracellular signaling pathways and the function of this Bcl-2 family member. As discussed above, BAD is believed to play a role in the apoptotic signaling pathway through an association with Bcl-2 family members, chiefly the cell death inhibitors Bcl-$X_L$ and Bcl-2 (Yang et al., 1995). Upon being dephosphorylated, BAD is active and forms heterodimers with Bcl-$X_L$ and Bcl-2, thereby displacing BAX and promoting cell death. The death-promoting activity of BAD can be inhibited by the phosphorylation of either of two serine residues, corresponding to the serines at position 112 and position 136 in the amino acid sequence of murine BAD (SEQ ID NO:2). Upon phosphorylation of either of these two sites, BAD no longer binds Bcl-$X_L$ or Bcl-2 and instead, is thought to be bound by the phosphoserine-binding protein 14-3-3, thereby allowing Bcl-$X_L$ and Bcl-2 to perform their anti-apoptotic functions (Zha et al., 1996).

The interaction of murine BAD and the cytosol polypeptide 14-3-3 was discovered using a GST-BAD fusion polypeptide having a heart muscle kinase (HMK) motif. The fusion polypeptide was labeled with $\gamma^{32}$P-ATP in vitro and used as a probe to screen an oligo (dT)-primed day-16 mouse embryonic EXlox cDNA expression library (Blanar and Rutter, 1992). Thereby two independent clones, each encoding a polypeptide of the tau form (τ) of 14-3-3 that bound to the BAD fusion polypeptide, were isolated (Nielsen, 1991).

The members of the 14-3-3 family, identified in at least seven mammalian isoforms, are highly conserved and ubiquitously expressed. They bind to and regulate a variety of proteins, including a number of proteins involved in signal transduction. Family members recognize and bind sequences containing a conserved phosphoserine motif (Muslin et al, 1996).

Muslin et al. identified a number of polypeptides, including BAD, that contain this motif and postulated that if these other polypeptides were appropriately phosphorylated, 14-3-3 would bind them as well. However, they did not perform any experiments to determine whether 14-3-3 in fact binds phosphorylated BAD, nor did they discuss possible physiological consequences of such binding. Moreover, there was no discussion of other potential BAD serine phosphorylation sites. Only the general suggestion that 14-3-3 might interact with polypeptides to perform an essential chaperone function was advanced. Korsmeyer also suggested a likely role for 14-3-3 as a chaperone or protective binding polypeptide. In the case of BAD, it was suggested that 14-3-3 might facilitate the translocation of phosphorylated BAD from the mitochondrial membrane to cytosolic compartments, sequestering it therein (U.S. Pat. No. 5,856,445).

Thus far, BAD is the only known pro-apoptotic member of the Bcl-2 family whose function is regulated by phosphorylation. The serine/threonine kinase Akt, a downstream effector of PI 3-kinase, phosphorylates murine BAD on the serine at position 136 (also called "Ser136" or "serine-136"), thereby preventing murine BAD from associating with Bcl-2 or Bcl-$X_L$, and freeing these proteins to promote cell survival. (Datta et al., 1997; del Peso et al., 1997).

In addition, murine BAD is phosphorylated at the serine at position 112 (also called "Ser112" or "serine-112"). Although phosphorylation of Ser136 was sufficient to prevent BAD from binding to Bcl-$X_L$, phosphorylation of Ser112 appeared critical for cellular survival in some cell types but not in others (Zha et al., 1996; Datta et al., 1997). Several candidate enzymes have been proposed to be responsible for the phosphorylation of Ser112, including PKA, c-Raf, and MEK (Harada et al., 1999; Wang and Reed, 1998; Scheid and Duronio, 1998). However, the discoveries of the present invention indicate that Ser112 is, at best, a minor site of phosphorylation by PKA. Similarly, Akt does not appear to phosphorylate BAD on Ser112.

Some disease conditions may be related to the development of a defective down-regulation (i.e., inhibition or modulation) of apoptosis in the affected cells. For example, neoplasias may result, at least in part, from an apoptosis-resistant state in which cell proliferation signals inappropriately exceed cell death signals and apoptosis is thereby down-regulated. Furthermore, some DNA viruses such as Epstein-Barr virus, African swine fever virus and adenovirus, parasitize the host's cellular machinery to drive their own replication and at the same time inhibit or modulate apoptosis, thereby repressing cell death and allowing the host cell to continue reproducing the virus. Moreover, certain other disease conditions such as lymphoproliferative conditions, arthritis, inflammation, autoimmune diseases, and cancers, including drug-resistant cancers, may result from a down-regulation (e.g., inhibition or modulation) of apoptosis. In such disease conditions it would be desirable to promote or induce apoptosis. By manipulating members of the signal transduction cascade that trigger apoptosis, one could selectively induce apoptosis. For example, BAD could be altered to promote or induce its binding to Bcl-$X_L$ and/or Bcl-2 and, thereby, diminish (or inhibit or modulate) the cell-survival promoting activity of these cell death inhibitors.

Conversely, in certain disease conditions it would be desirable to inhibit or modulate apoptosis, for example, in the treatment of immunodeficiency diseases, including AIDS, senescence, neurodegenerative disease, ischemic and reperfusion cell death, infertility, and wound-healing. In such cases, BAD could be altered to block its ability to bind Bcl-$X_L$ and/or Bcl-2 and, thereby, promote or induce the cell death repressor, or anti-apoptotic, activity of these cell death inhibitors.

Accordingly, it would be desirable to identify novel compositions and methods that could be used to modulate the binding of BAD to members of the Bcl-2 family, such as Bcl-$X_L$ and Bcl-2, and thereby induce, promote, inhibit or modulate apoptosis, or induce, promote, inhibit, or modulate cell survival, and to utilize these novel compositions and methods as a basis for treatment of disease conditions involving either inappropriate inhibition or inappropriate acceleration of cell death.

SUMMARY OF THE INVENTION

The present invention relates to the discovery of a novel phosphorylation site of BAD that is regulated differentially from other known phosphorylation events of BAD. The novel phosphorylation site is at the serine at position 155 (also called "Ser155" or "serine-155") of SEQ ID NO:2 of a murine BAD ("longer murine BAD") that corresponds to the serine at position 118 (also called "Ser118" and "serine-118") of SEQ ID NO:1 of a human BAD, and the serine at position 113 (also called "Ser113" or Serine-113") of SEQ ID NO:3 of a murine BAD ("shorter murine BAD"). A particularly significant aspect of the present invention relates to the discovery that the phosphorylation of BAD at the novel phosphorylation site renders BAD unable to bind to Bcl-$X_L$, and promotes, induces, or modulates cell survival (and/or inhibits or modulates apoptosis). Moreover, the phosphorylation of BAD at the novel site is not dependent on the activation of PI 3-kinase and Akt. Rather, the phosphorylation of BAD at the novel phosphorylation site is regulated by the cAMP-dependent protein kinase ("PKA"). For example, the phosphorylation of endogenous BAD at Ser155 in Rat-1 fibroblasts and several tumor cell lines, such as A275 and A431, can be induced by growth factors at physiological levels in a PKA-dependent manner, but not in a PI 3-kinase dependent and Akt-dependent manner. Consistent with these findings, cells treated with L-epinephrine, a G-protein-coupled receptor ligand that induces elevation of intracellular cAMP levels, exhibit phosphorylation of BAD at Ser155. In addition, the present invention relates to the discovery that, both in vitro and in vivo, Ser155 is the only major site of BAD phosphorylation by PKA, and that the phosphorylation of BAD at Ser155 contributes significantly to the overall phosphorylation of BAD.

The present invention further relates to the discovery that BAD, having a mutation wherein Ser155 is changed to an alanine, promotes, agonizes, induces or modulates apoptotic activity in HeLa cells, as compared to the naturally-occurring or wild-type mammalian BAD. Similarly, the elevation of the level of intracellular cAMP promotes, induces, or modulates cell survival (and/or inhibits or modulates apoptosis) in HeLa cells expressing the naturally-occurring or wild-type mammalian BAD, but not in HeLa cells expressing the BAD having a mutation at Ser155. In contrast, the change of serine 155 to an aspartic acid, which mimics the phospho-Ser155 BAD, showed no apoptotic activity when expressed in cells.

Accordingly, the object of the present invention is to provide compositions and methods that regulate apoptosis and/or cell survival (apoptotic agonists and antagonists), for example, by promoting, inducing, inhibiting, or modulating apoptosis, or promoting, inducing, inhibiting, or modulating cell survival, and to provide methods of making and screening for such compositions.

More specifically, an object of the present invention is to provide novel compounds and methods that can alter the phosphorylation of BAD and/or binding of BAD to members of the Bcl-2 family, such as Bcl-$X_L$ and Bcl-2, and thereby regulate apoptosis and/or cell survival, for example, by promoting, inducing, inhibiting, or modulating apoptosis, or promoting, inducing, inhibiting, or modulating cell survival, and to provide methods of making and screening for such compounds. Another object of the present invention is to provide methods that utilize such novel compounds as a basis for treatment of disease conditions involving either inappropriate inhibition or inappropriate acceleration of cell death. Such novel compounds include, for example, polypeptides and polynucleotides, fragments of full-length polypeptides and polynucleotides, including mutants and homologs thereof, and chemical compounds, including peptide mimetics.

An embodiment of the present invention provides isolated or synthetic polypeptides comprising an amino acid sequence of a mutant BAD, or fragments of said isolated or synthetic polypeptides comprising a less than full-length amino acid sequence of a mutant BAD, having cell death promoting activity. The amino acid sequence of the isolated or synthetic polypeptides of a mutant BAD, or said fragments, wherein the amino acid sequence of said mutant BAD, or said fragment, is identical to or substantially identical to either SEQ ID NO:1, SEQ ID NO:2, or SEQ ID NO:3, contains a domain that is substantially identical to a BH3 domain of a naturally-occurring or wild-type mammalian BAD, and does not contain a serine at a position corresponding to position 118 of SEQ ID NO:1, position 155 of SEQ ID NO:2, or position 113 of SEQ ID NO:3. The position corresponding to position 118 of SEQ ID NO:1, position 155 of SEQ ID NO:2, or position 113 of SEQ ID NO:3 is determined by alignment of the amino acid sequence of the isolated or synthetic polypeptides of the mutant BAD, or said fragments, to SEQ ID NO:1, SEQ ID NO:2, or SEQ ID NO:3, respectively.

More particularly, an embodiment of the present invention provides isolated or synthetic polypeptides comprising an amino acid sequence of a mutant BAD, or fragments of an isolated or synthetic polypeptide comprising a less than full-length amino acid sequence of a mutant BAD, having cell death promoting activity, and/or having the ability to bind Bcl-$X_L$ and/or Bcl-2. The binding of said isolated or synthetic polypeptides comprising an amino acid sequence of a mutant BAD, or said fragments, may occur, for example, through a domain that is substantially identical to a BH3 domain of a naturally-occurring or wild-type mammalian BAD. The amino acid sequence of the isolated or synthetic polypeptides of a mutant BAD, or said fragments, is derived from a naturally-occurring or wild-type mammalian BAD, contains a domain that is substantially identical to a BH3 domain of a naturally-occurring or wild-type mammalian BAD, and does not contain a serine at a position corresponding to position 118 of SEQ ID NO:1, position 155 of SEQ ID NO:2, or position 113 of SEQ ID NO:3. The position corresponding to position 118 of SEQ ID NO:1, position 155 of SEQ ID NO:2, or position 113 of SEQ ID NO:3 is determined by alignment of the amino acid sequence of the isolated or synthetic polypeptides of a mutant BAD, or said fragments, to SEQ ID NO:1, SEQ ID NO:2, or SEQ ID NO:3, respectively.

An embodiment of the present invention provides isolated or synthetic polypeptides comprising an amino acid sequence of a mutant BAD, or fragments of an isolated or synthetic polypeptide comprising a less than full-length amino acid sequence of a mutant BAD, having cell death promoting activity. The amino acid sequence of the isolated or synthetic polypeptides of a mutant BAD, or said fragments, is derived from a naturally-occurring or wild-type mammalian BAD, contains a domain that is substantially identical to a BH3 domain of a naturally-occurring or wild-type mammalian BAD, and contains an alanine at a position corresponding to position 118 of SEQ ID NO:1, position 155 of SEQ ID NO:2, or position 113 of SEQ ID NO:3. The position corresponding to position 118 of SEQ ID NO:1, position 155 of SEQ ID NO:2, or position 113 of SEQ ID NO:3 is determined by alignment of the amino acid sequence of the isolated or synthetic polypeptides of the mutant BAD, or said fragments, to SEQ ID NO:1, SEQ ID NO:2, or SEQ ID NO:3, respectively.

An embodiment of the present invention provides isolated or synthetic polypeptides comprising an amino acid sequence of a mutant BAD, or fragments of an isolated or synthetic polypeptide comprising a less than full-length amino acid sequence of a mutant BAD, having cell death promoting activity. The amino acid sequence of the isolated or synthetic polypeptides of a mutant BAD, or said fragments, is derived from a naturally-occurring or wild-type mammalian BAD, contains a domain that is substantially identical to a BH3 domain of a naturally-occurring or wild-type mammalian BAD, and does not contain a glycine at a position corresponding to position 118 of SEQ ID NO:1, position 155 of SEQ ID NO:2, or position 113 of SEQ ID NO:3. The position corresponding to position 118 of SEQ ID NO:1, position 155 of SEQ ID NO:2, or position 113 of SEQ ID NO:3 is determined by alignment of the amino acid sequence of the isolated or synthetic polypeptides of the mutant BAD, or said fragments, to SEQ ID NO:1, SEQ ID NO:2, or SEQ ID NO:3, respectively.

An embodiment of the present invention provides isolated or synthetic polypeptides comprising an amino acid sequence of a mutant BAD, or fragments of an isolated or synthetic polypeptide comprising a less than full-length amino acid sequence of a mutant BAD, having cell death promoting activity. The amino acid sequence of the isolated or synthetic polypeptides of a mutant BAD, or said fragments, is derived from a naturally-occurring or wild-type mammalian BAD, contains a domain that is substantially identical to a BH3 domain of a naturally-occurring or wild-type mammalian BAD, and does not contain an alanine at a position corresponding to position 118 of SEQ ID NO:1, position 155 of SEQ ID NO:2, or position 113 of SEQ ID NO:3. The position corresponding to position 118 of SEQ ID NO:1, position 155 of SEQ ID NO:2, or position 113 of SEQ ID NO:3 is determined by alignment of the amino acid sequence of the isolated or synthetic polypeptides of a mutant BAD, or said fragments, to SEQ ID NO:1, SEQ ID NO:2, or SEQ ID NO:3, respectively.

More particularly, an embodiment of the present invention provides isolated or synthetic polypeptides comprising an amino acid sequence of a mutant BAD, or fragments of an isolated or synthetic polypeptide comprising a less than full-length amino acid sequence of a mutant BAD, having cell death promoting activity. The amino acid sequence of the isolated or synthetic polypeptides of a mutant BAD, or said fragments, comprises the amino acid sequence corresponding to positions 103–123 of SEQ ID NO:1, positions 140–160 of SEQ ID NO:2, or positions 98–118 of SEQ ID NO:3, contains a domain that is substantially identical to a BH3 domain of a naturally-occurring or wild-type mammalian BAD, and does not contain a serine at a position corresponding to position 118 of SEQ ID NO:1, position 155 of SEQ ID NO:2, or position 113 of SEQ ID NO:3. The position corresponding to position 118 of SEQ ID NO:1, position 155 of SEQ ID NO:2, or position 113 of SEQ ID NO:3 is determined by alignment of the amino acid sequence of the isolated or synthetic polypeptides of the mutant BAD, or said fragments, to SEQ ID NO:1, SEQ ID NO:2, or SEQ ID NO:3, respectively.

An embodiment of the present invention provides isolated or synthetic polypeptides comprising an amino acid sequence of a mutant BAD, or fragments of an isolated or synthetic polypeptide comprising a less than full-length amino acid sequence of a mutant BAD, having cell death promoting activity. The amino acid sequence of the isolated or synthetic polypeptides of a mutant BAD, or said fragments, contains a domain that is substantially identical to a BH3 domain of a naturally-occurring or wild-type mammalian BAD, wherein the amino acid sequence of the naturally-occurring or wild-type mammalian BAD is SEQ ID NO:1, SEQ ID NO:2, or SEQ ID NO:3, and does not contain a serine at a position corresponding to position 118 of SEQ ID NO:1, position 155 of SEQ ID NO:2, or position 113 of SEQ ID NO:3. The position corresponding to position 118 of SEQ ID NO:1, position 155 of SEQ ID NO:2, or position 113 of SEQ ID NO:3 is determined by alignment of the amino acid sequence of the isolated or synthetic polypeptides of the mutant BAD, or said fragments, to SEQ ID NO:1, SEQ ID NO:2, or SEQ ID NO:3, respectively.

Another embodiment of the present invention provides methods for making polypeptides of a mutant BAD comprising an amino acid sequence of a naturally-occurring or wild-type mammalian BAD, or said fragments comprising a less than full-length amino acid sequence of a naturally-occurring or wild-type mammalian BAD. The methods comprise first selecting an amino acid sequence of a naturally-occurring or wild-type mammalian BAD, or selecting a less than full-length amino acid sequence of a naturally-occurring or wild-type mammalian BAD, comprising a BH3 domain substantially identical to the BH3 domain encoded by the amino acids at positions 114–122 of SEQ ID NO:1, positions 151–159 of SEQ ID NO:2, or positions 109–117 of SEQ ID NO:3. The BH3 domain of the naturally-occurring or wild-type mammalian BAD, or the BH3 domain of said fragment, is identified by alignment of the amino acid sequence of the naturally-occurring or wild-type mammalian BAD, or the amino acid sequence of said fragment, to SEQ ID NO:1, SEQ ID NO:2, or SEQ ID NO:3, respectively. Second, the amino acid of the amino acid sequence of the naturally-occurring or wild-type mammalian BAD, or said fragment, at a position corresponding to position 118 of SEQ ID NO:1, position 155 of SEQ ID NO:2, or position 113 of SEQ ID NO:3 is changed to an amino acid other than serine. Thereby, polypeptides of a mutant BAD, or said fragments, comprising the amino acid sequence of a naturally-occurring or wild-type mammalian BAD having a mutation of the amino acid corresponding to position 118 of SEQ ID NO:1, position 155 of SEQ ID NO:2, or position 113 of SEQ ID NO:3, are made.

In particular, an embodiment of the present invention provides methods for making polypeptides of a mutant BAD comprising an amino acid sequence of a naturally-occurring or wild-type mammalian BAD, or said fragments comprising a less than full-length amino acid sequence of a naturally-occurring or wild-type mammalian BAD. The methods comprise first selecting an amino acid sequence of a naturally-occurring or wild-type mammalian BAD, or selecting a less than full-length amino acid sequence of a naturally-occurring or wild-type mammalian BAD, comprising a BH3 domain substantially identical to the BH3 domain encoded by the amino acids at positions 114–122 of SEQ ID NO:1, positions 151–159 of SEQ ID NO:2, or positions 109–117 of SEQ ID NO:3. The BH3 domain of the naturally-occurring or wild-type mammalian BAD, or the BH3 domain of said fragment, is identified by alignment of the amino acid sequence of the naturally-occurring or wild-type mammalian BAD, or the amino acid sequence of said fragment, to SEQ ID NO:1, SEQ ID NO:2, or SEQ ID NO:3, respectively. Second, the amino acid of the amino acid sequence of the naturally-occurring or wild-type mammalian BAD, or said fragment, at a position corresponding to position 118 of SEQ ID NO:1, position 155 of SEQ ID NO:2, or position 113 of SEQ ID NO:3 is changed to alanine.

Also in particular, an embodiment of the present invention provides methods for making polypeptides of a mutant BAD comprising an amino acid sequence of the naturally-occurring or wild-type mammalian BAD encoded by SEQ ID NO:1, SEQ ID NO:2, or SEQ ID NO:3, or said fragments comprising a less than full-length amino acid sequence of the naturally-occurring or wild-type mammalian BAD encoded by SEQ ID NO:1, SEQ ID NO:2, or SEQ ID NO:3. The methods comprise first selecting an amino acid sequence of a naturally-occurring or wild-type mammalian BAD, or selecting a less than full-length amino acid sequence of a naturally-occurring or wild-type mammalian BAD, comprising a BH3 domain substantially identical to the BH3 domain encoded by the amino acids at positions 114–122 of SEQ ID NO:1, positions 151–159 of SEQ ID NO:2, or positions 109–117 of SEQ ID NO:3. The BH3 domain of the naturally-occurring or wild-type mammalian BAD, or the BH3 domain of said fragment, is identified by alignment of the amino acid sequence of the naturally-occurring or wild-type mammalian BAD, or the amino acid sequence of said fragment, to SEQ ID NO:1, SEQ ID NO:2, or SEQ ID NO:3, respectively. Second, the amino acid of the amino acid sequence of the naturally-occurring or wild-type mammalian BAD, or said fragment, at a position corresponding to position 118 of SEQ ID NO:1, position 155 of SEQ ID NO:2, or position 113 of SEQ ID NO:3 is changed to an amino acid other than serine.

Another embodiment of the present invention provides methods for making polypeptides of a mutant BAD comprising an amino acid sequence of a naturally-occurring or wild-type mammalian BAD, or fragments comprising a less than full-length amino acid sequence of a naturally-occurring or wild-type mammalian BAD. The methods comprise first selecting an amino acid sequence of a naturally-occurring or wild-type mammalian BAD, or selecting a less than full-length amino acid sequence of a naturally-occurring or wild-type mammalian BAD, comprising a BH3 domain substantially identical to the BH3 domain encoded by the amino acids at positions 114–122 of SEQ ID NO:1, positions 151–159 of SEQ ID NO:2, or positions 109–117 of SEQ ID NO:3. The BH3 domain of the naturally-occurring or wild-type mammalian BAD, or the BH3 domain of said fragment, is identified by alignment of the amino acid sequence of the naturally-occurring or wild-type mammalian BAD, or the amino acid sequence of said fragment, to SEQ ID NO:1, SEQ ID NO:2, or SEQ ID NO:3, respectively. Second the amino acid of the amino acid sequence of the naturally-occurring or wild-type mammalian BAD, or said fragment, at a position corresponding to position 118 of SEQ ID NO:1, position 155 of SEQ ID NO:2, or position 113 of SEQ ID NO:3 is changed to an amino acid other than serine. Third, the polypeptide of the mutant BAD, or said fragment, is expressed in a host cell, wherein the host cell is transformed with a polynucleotide comprising the amino acid sequence of the mutant BAD, or comprising the amino acid sequence of said fragment, respectively.

Another embodiment of the present invention provides methods of screening a candidate drug for activity that promotes apoptosis. The methods comprise first contacting a candidate drug with a sample comprising a mammalian BAD, or fragment of a mammalian BAD, and a kinase, to form a reacted fraction. The mammalian BAD, or said fragment, comprises an amino acid sequence containing a serine at a position corresponding to position 118 of SEQ ID NO:1, position 155 of SEQ ID NO:2, or position 113 of SEQ ID NO:3. The position of the serine is identified by alignment of the amino acid sequence of the mammalian BAD, or said fragment, to SEQ ID NO:1, SEQ ID NO:2, or SEQ ID NO:3, respectively. The kinase has phosphorylation activity capable of phosphorylating the mammalian BAD. Second, the reacted fraction is compared to a control fraction to determine whether the candidate drug inhibits the phosphorylation activity of the kinase and, thereby, has activity that promotes apoptosis, by assaying for the amount of the mammalian BAD, or said fragment, that is unphosphorylated at the identified serine in the reacted fraction as compared to a control fraction. Alternatively, the reacted fraction is compared to a control fraction to determine whether the candidate drug inhibits the phosphorylation activity of the kinase and, thereby, has activity that promotes apoptosis, by assaying the isolated fraction as compared to a control fraction, for an amount of the mammalian BAD, or said fragment, that is bound to Bcl-$X_L$ and/or Bcl-2. Preferably, treatment of the control fraction is essentially identical to that of the reacted fraction, except the mammalian BAD, or said fragment, in the control fraction is not contacted with the candidate drug.

Another embodiment of the present invention provides methods of inducing apoptosis in a cell expressing a mammalian BAD, or fragment of a mammalian BAD. The methods comprise first preparing a culture containing a cell line expressing the mammalian BAD, or said fragment. The mammalian BAD, or said fragment, comprises an amino acid sequence containing a serine at a position corresponding to position 118 of SEQ ID NO:1, position 155 of SEQ ID NO:2, or position 113 of SEQ ID NO:3. The position of the serine is identified by alignment of the amino acid sequence of the mammalian BAD, or said fragment, to SEQ ID NO:1, SEQ ID NO:2, or SEQ ID NO:3, respectively. Second, the cultured cells are contacted with an extracellular agent, and/or an intracellular agent is induced in the cultured cells, to form a reacted fraction, wherein the extracellular and/or the intracellular agent is capable of inhibiting the phosphorylation activity of a kinase in the cell that is capable of phosphorylating the serine at position 118 of SEQ ID NO:1, position 155 of SEQ ID NO:2, or position 113 of SEQ ID NO:3. An example of such an extracellular or intracellular agent is inhibitor H89, wherein H89 inhibits the phosphorylation activity of an intracellular kinase. Kinase inhibition can also be achieved, for example, by the binding of a polypeptide or a polynucleotide to the kinase, thereby inhibiting the phosphorylation activity of the kinase, or by the binding of a polypeptide or polynucleotide to a polynucleotide that encodes the kinase, thereby preventing the expression of the kinase. An example of such a kinase is PKA, the cyclic AMP (cAMP)-dependent protein kinase. Alternatively, the cultured cells are contacted with an extracellular agent, and/or an intracellular agent is induced in the cultured cells, wherein the extracellular and/or intracellular agent is capable of activating the phosphatase activity of a phosphatase in the cell that is capable of dephosphorylating the mammalian BAD, or said fragment, that is phosphorylated at the serine corresponding to position 118 of SEQ ID NO:1, position 155 of SEQ ID NO:2, or position 113 of SEQ ID NO:3. Third, treated cells in the reacted fraction are compared with untreated control cells to determine whether apoptosis is induced in the treated cells by assaying for the amount of the mammalian BAD, or said fragment, that is unphosphorylated and/or dephosphorylated in each. Alternatively, the treated cells in the reacted fraction are compared to untreated control cells to determine whether apoptosis is induced in the treated cells at a higher level by monitoring indicia of apoptosis in each. Preferably, treatment of the control cells is essentially identical to that of the treated cells, except the control cells are not contacted with an extracellular agent and/or an intracellular agent is not induced in the control cells.

Another embodiment of the present invention provides methods of assaying a candidate compound for phosphatase activity capable of dephosphorylating a mammalian BAD, or fragment of a mammalian BAD, at a serine at a position in the amino acid sequence of the mammalian BAD, or said fragment, corresponding to position 118 of SEQ ID NO:1, position 155 of SEQ ID NO:2, or position 113 of SEQ ID NO:3. The position of the serine is identified by alignment of the amino acid sequence of the mammalian BAD, or said fragment, to SEQ ID NO:1, SEQ ID NO:2, or SEQ ID NO:3, respectively. The methods comprise first contacting the candidate compound with the mammalian BAD, or said fragment, to form a reacted fraction, wherein the mammalian BAD, or said fragment, is de-phosphorylated at the specified serine. Second, the reacted fraction is compared to a control fraction to determine whether the candidate compound has phosphatase activity by assaying for the amount of the mammalian BAD, or said fragment, that is bound to Bcl-$X_L$ and/or Bcl-2 in the reacted fraction as compared to a control fraction. Preferably, treatment of the control fraction is essentially identical to that of the reacted fraction, except the control fraction is not contacted with the candidate compound.

Another embodiment of the present invention provides methods of assaying a candidate compound for phosphatase activity capable of dephosphorylating a mammalian BAD, or fragment of a mammalian BAD, at a serine at a position in the amino acid sequence of the mammalian BAD, or said fragment, corresponding to position 118 of SEQ ID NO:1, position 155 of SEQ ID NO:2, or position 113 of SEQ ID NO:3. The position of the serine is identified by alignment of the amino acid sequence of the mammalian BAD, or said fragment, to SEQ ID NO:1, SEQ ID NO:2, or SEQ ID NO:3, respectively. The methods comprise first contacting the candidate compound with the mammalian BAD, or said fragment, to form a reacted fraction, wherein the mammalian BAD, or said fragment, is de-phosphorylated at the specified serine. Second, the reacted fraction is compared to a control fraction to determine whether the candidate compound has phosphatase activity by assaying for an amount of the mammalian BAD, or said fragment, that is dephosphorylated at the serine in the reacted fraction as compared to the control fraction. Preferably, treatment of the control fraction is essentially identical to that of the reacted fraction, except the control fraction is not contacted with the candidate compound.

Another embodiment of the present invention provides methods of screening a candidate drug for activity that promotes cell survival. The methods comprise first contacting the candidate drug with a mammalian BAD, or fragment of a mammalian BAD, and, optionally, a kinase, to form a reacted fraction. The mammalian BAD, or said fragment, is capable of being phosphorylated at a serine at a position in the amino acid sequence of the mammalian BAD, or said fragment, corresponding to position 118 of SEQ ID NO:1, position 155 of SEQ ID NO:2, or position 113 of SEQ ID NO:3. The position of the serine is identified by alignment of the amino acid sequence of the mammalian BAD, or said fragment, to SEQ ID NO:1, SEQ ID NO:2 and SEQ ID NO:3, respectively. Second, the reacted fraction is compared to a control fraction to determine whether the candidate drug has activity that promotes cell survival by assaying for the amount of the mammalian BAD, or said fragment, that is phosphorylated at the serine in the reacted fraction as compared to the control fraction. Preferably, treatment of the control fraction is essentially identical to that of the reacted fraction, except the control fraction is not contacted with the candidate drug.

Another embodiment of the present invention provides methods of screening a candidate drug for activity that promotes cell survival. The methods comprise first contacting the candidate drug with a mammalian BAD, or fragment of a mammalian BAD, and, optionally, a kinase, to form a reacted fraction. The mammalian BAD, or said fragment, is capable of being phosphorylated at a serine at a position in the amino acid sequence of the mammalian BAD, or said fragment, corresponding to position 118 of SEQ ID NO:1, position 155 of SEQ ID NO:2, or position 113 of SEQ ID NO:3. The position of the serine is identified by alignment of the amino acid sequence of the mammalian BAD, or said fragment, to SEQ ID NO:1, SEQ ID NO:2 and SEQ ID NO:3, respectively. Second, the reacted fraction is contacted with Bcl-$X_L$ and/or Bcl-2. Third, the reacted fraction is compared to a control fraction to determine whether the candidate drug has activity that promotes cell survival by assaying for the amount of the mammalian BAD bound to Bcl-$X_L$ and/or Bcl-2, or the amount of said fragment bound to Bcl-$X_L$ and/or Bcl-2. Alternatively, the reacted fraction is compared to a control fraction to determine whether the candidate drug has activity that promotes cell survival by assaying for the amount of the mammalian BAD, or said fragment, that is phosphorylated at the specified serine in the reacted fraction as compared to the control fraction. Preferably, treatment of the control fraction is essentially identical to that of the reacted fraction, except the control fraction is not contacted with the candidate drug.

Another embodiment of the present invention provides methods of screening a candidate drug for activity that promotes cell survival. The methods comprise first preparing a cell culture containing a cell line expressing a mammalian BAD, or fragment of a mammalian BAD, wherein the cell line has activity that promotes apoptosis, or is capable of having activity that promotes apoptosis. The mammalian BAD, or said fragment, comprises an amino acid sequence containing a serine at a position corresponding to position 118 of SEQ ID NO:1, position 155 of SEQ ID NO:2, or position 113 of SEQ ID NO:3. The position of the serine is identified by alignment of the amino acid sequence of the mammalian BAD, or fragment of the mammalian BAD, to SEQ ID NO:1, SEQ ID NO:2, or SEQ ID NO:3, respectively. Second, the cell culture is contacted with the candidate drug to form a reacted fraction. Third, the cells in the reacted fraction are compared to cells of a control culture to determine whether the candidate drug has activity promoting cell survival by monitoring the viability of the cells in the reacted fraction as compared to the cells of the control culture. Preferably, treatment of the control cell culture is essentially identical to that of the cell culture of the reacted fraction, except that the control cell culture is not contacted with the candidate drug.

Another embodiment of the present invention provides methods of screening a candidate drug for activity that promotes cell survival. The methods comprise first preparing a cell culture containing a cell line expressing a mammalian BAD, or fragment of a mammalian BAD, wherein the cell line has activity that promotes apoptosis, or is capable of having activity that promotes apoptosis. The mammalian BAD, or said fragment, comprises an amino acid sequence containing a serine at a position corresponding to position 118 of SEQ ID NO:1, position 155 of SEQ ID NO:2, or position 113 of SEQ ID NO:3. The position of the serine is identified by alignment of the amino acid sequence of the mammalian BAD, or fragment of the mammalian BAD, to SEQ ID NO:1, SEQ ID NO:2, or SEQ ID NO:3, respectively. Second, the cell culture is contacted with the candidate drug to form a reacted fraction. Third, cultured cells in the reacted fraction are compared to cells of a control culture, to determine whether the candidate drug has activity promoting cell survival, by monitoring the viability of the cells in the reacted fraction as compared to the control cells. Alternatively, the cells in the reacted fraction can be compared to the control cells, in order to determine whether the candidate drug has activity promoting cell survival, by further contacting the cells of both cultures with at least one antibody specific for: 1) the mammalian BAD, or said fragment, that is phosphorylated at the serine; or 2) the mammalian BAD, or said fragment, that is unphosphorylated at the serine; and then assaying for the amount of the antibody binding to the mammalian BAD, or said fragment. Preferably, treatment of the control cells is essentially identical to treatment of the cells in the reacted fraction, except that the control cells are not contacted with the candidate drug.

Another embodiment of the present invention provides methods of inhibiting apoptosis in a cell expressing a mammalian BAD, or fragment of a mammalian BAD. The methods comprise first preparing a cell culture containing a cell line expressing a mammalian BAD, or said fragment. The mammalian BAD, or said fragment, comprises an amino acid sequence containing a serine at a position corresponding to position 118 of SEQ ID NO:1, position 155 of SEQ ID NO:2, or position 113 of SEQ ID NO:3. The position of the serine is identified by alignment of the amino acid sequence of the mammalian BAD, or fragment of the mammalian BAD, to SEQ ID NO:1, SEQ ID NO:2, or SEQ ID NO:3, respectively. Second, the cultured cells are contacted with an extracellular agent, and/or an intracellular agent is induced, to form a reacted fraction and, thereby, a kinase in the cells is activated, wherein the kinase is capable of phosphorylating the mammalian BAD, or said fragment, at the specified serine. Third, the cells in the reacted fraction are compared to a control cell line to determine whether apoptosis is inhibited in the cells in the reacted fraction, by 1) assaying for the amount of the mammalian BAD, or said fragment, that is phosphorylated at the specified serine in the cells in the reacted fraction as compared to the control cells; and/or 2) monitoring indicia of apoptosis in the cells in the reacted fraction as compared to the control cells. Preferably, treatment of the control cells is essentially identical to treatment of the cells in the reacted fraction, except that the control cells do not express a mammalian BAD, or said fragment, that is capable of being phosphorylated by the kinase. Examples of a serine kinase capable of phosphorylating the mammalian BAD, or said fragment, at the serine include PKA. Further examples of serine kinases capable of phosphorylating the mammalian BAD, or fragment of the mammalian BAD, include a heterologous kinase. Examples of a mammalian BAD include a heterologous mammalian BAD, and examples of a fragment of a mammalian BAD include a fragment of a heterologous mammalian BAD. Examples of an extracellular agent and/or said intracellular agent include a ligand of a G-protein-coupled receptor, such as L-epinephrine.

Another embodiment of the present invention provides methods of assaying a candidate compound for a kinase activity capable of phosphorylating a mammalian BAD, or fragment of a mammalian BAD, at a serine at a position in the amino acid sequence of the mammalian BAD, or said fragment, corresponding to position 118 of SEQ ID NO:1; position 155 of SEQ ID NO:2; or position 113 of SEQ ID NO:3. The position of the serine is identified by alignment of the amino acid sequence of the mammalian BAD, or fragment of mammalian BAD, to SEQ ID NO:1, SEQ ID NO:2, or SEQ ID NO:3, respectively. The methods comprise first contacting the candidate compound with the mammalian BAD, or said fragment, to form a reacted fraction. Second, to determine whether the candidate compound has kinase activity capable of phosphorylating the mammalian BAD, or said fragment, the reacted fraction is assayed for the amount of the mammalian BAD, or said fragment, that is phosphorylated at the specified serine. Alternatively, to determine whether the candidate compound has kinase activity capable of phosphorylating the mammalian BAD, or said fragment, at the specified serine, the reacted fraction is assayed, for example, by detecting: 1) the amount of radioactive label on the serine, wherein the cell is contacted with radioactive label and the radioactive label is attached to the serine when the serine is phosphorylated; 2) a difference in the electrophoretic mobility of the mammalian BAD, or said fragment, that is phosphorylated at the serine as compared to the mammalian BAD, or said fragment, that is unphosphorylated at the serine; or 3) the amount of the mammalian BAD, or said fragment, bound to an antibody specific for the mammalian BAD, or said fragment, that is phosphorylated at the serine. Examples of an antibody specific for the mammalian BAD, or said fragment, that is phosphorylated at the serine include a monoclonal antibody.

Another embodiment of the present invention provides methods of screening a candidate drug for activity that promotes the phosphorylation of a mammalian BAD, or fragment of a mammalian BAD, at a serine at a position in the amino acid sequence of the mammalian BAD, or said fragment, corresponding to position 118 of SEQ ID NO:1, position 155 of SEQ ID NO:2, or position 113 of SEQ ID NO:3. The position of the serine is identified by alignment of the amino acid sequence of the mammalian BAD, or said fragment, to SEQ ID NO:1, SEQ ID NO:2, or SEQ ID NO:3, respectively. The methods comprise first contacting the candidate drug with a sample comprising $Bcl-X_L$ and the mammalian BAD, or said fragment, to form a reacted fraction, wherein the mammalian BAD, or said fragment is capable of being phosphorylated at the serine. Second, the reacted fraction is compared to a control fraction to determine whether the candidate drug has activity that promotes phosphorylation, by assaying for: 1) the amount of mammalian BAD, or said fragment, that is not bound to $Bcl-X_L$ in the reacted fraction as compared to the control fraction; and/or 2) the amount of the mammalian BAD, or said fragment, that is phosphorylated at the serine in the reacted fraction as compared to the control fraction. Preferably, treatment of the control fraction is essentially identical to that of the reacted fraction, except the mammalian BAD, or fragment of the mammalian BAD, in the control fraction is not contacted with the candidate drug, and/or the control fraction contains a mammalian BAD, or said fragment, that is not capable of being phosphorylated at the specified serine.

Another embodiment of the present invention provides methods of screening a candidate drug for an activity that promotes the phosphorylation of a mammalian BAD, or fragment of a mammalian BAD, at a serine at a position in the amino acid sequence of the mammalian BAD, or said fragment, corresponding to position 118 of SEQ ID NO:1, position 155 of SEQ ID NO:2, or position 113 of SEQ ID NO:3. The position of the serine is identified by alignment of the amino acid sequence of the mammalian BAD, or said fragment, to SEQ ID NO:1, SEQ ID NO:2, or SEQ ID NO:3, respectively. The methods comprise first contacting a candidate drug with a sample comprising the mammalian BAD, or said fragment, and a kinase, to form a reacted fraction, wherein the mammalian BAD, or said fragment, is capable of being phosphorylated by the kinase. Second, the reacted fraction is compared to a control fraction to determine whether the candidate drug has activity that promotes phosphorylation by the kinase by assaying for the amount of the mammalian BAD, or said fragment, that is phosphorylated at the specified serine in the reacted fraction as compared to the control fraction. Preferably, treatment of the control fraction is essentially identical to that of the reacted fraction, except the control fraction is not contacted with the candidate drug and/or the control fraction contains a mammalian BAD, or said fragment, that is not capable of being phosphorylated at the specified serine.

Another embodiment of the present invention provides methods of screening a candidate drug for activity that promotes phosphorylation in a cell of a mammalian BAD, or fragment of a mammalian BAD, at a serine at a position in the amino acid sequence of the mammalian BAD, or said fragment, corresponding to position 118 of SEQ ID NO:1, position 155 of SEQ ID NO:2, or position 113 of SEQ ID NO:3. The position is identified by alignment of the amino acid sequence of the mammalian BAD, or said fragment, to SEQ ID NO:1, SEQ ID NO:2, or SEQ ID NO:3, respectively. The methods comprise first preparing a cell culture containing a cell line expressing the mammalian BAD, or said fragment, wherein the cell line has activity that promotes apoptosis, or is capable of having activity that promotes apoptosis. Second, the cells are contacted with a candidate drug to form a reacted fraction. Third, the cells in the reacted fraction are compared to a control cell line to determine whether the candidate drug has activity that promotes phosphorylation by assaying for the amount of the mammalian BAD, or said fragment, that is phosphorylated at the specified serine, in the cells in the reacted fraction as compared to the control cells, and/or monitoring indicia of apoptosis in the cells in the reacted fraction as compared to the control cells. Alternatively, the cells in the reacted fraction are compared to control cells to determine whether the candidate drug has activity that promotes phosphorylation by further contacting cells of both fractions with at least one antibody, wherein the antibody is selected from a group consisting of at least one antibody specific for the mammalian BAD, or said fragment, that is phosphorylated at the serine, or at least one antibody specific for the mammalian BAD, or said fragment, that is unphosphorylated at the serine. Preferably, treatment of the control cell line is essentially identical to that of the cells in the reacted fraction, except the control cells are not contacted with the candidate drug.

Another embodiment of the present invention provides methods of screening a candidate drug for activity that modulates apoptosis promoting activity in a cell. The methods comprise first preparing a cell culture containing a cell line expressing a mammalian BAD, or fragment of a mammalian BAD. The mammalian BAD, or said fragment, comprises an amino acid sequence containing a serine at a position corresponding to position 118 of SEQ ID NO:1, position 155 of SEQ ID NO:2, or position 113 of SEQ ID NO:3. The position of the serine is identified by alignment of the amino acid sequence of the mammalian BAD, or said fragment, to SEQ ID NO:1, SEQ ID NO:2 or SEQ ID NO:3, respectively. Second, the cells are contacted with an apoptosis promoting substance, wherein the cell line has activity that promotes apoptosis, or is capable of having activity that promotes apoptosis. Third, the cells are contacted with the candidate drug to form a reacted fraction. Fourth, the cells in the reacted fraction are compared to a control cell line to determine whether the candidate drug has activity that modulates apoptosis promoting activity by: 1) assaying for the amount of the mammalian BAD, or said fragment, that is phosphorylated or unphosphorylated at the specified serine in the cells in the reacted fraction as compared to the control cells; or 2) monitoring indicia of apoptosis in the cells in the reacted fraction as compared to the control cells. Preferably, treatment of the control cell line is essentially identical to that of the cells in the reacted fraction, except that the control cells are not contacted with the candidate drug.

Another embodiment of the present invention provides antibodies that specifically bind to a mammalian BAD, or fragment of a mammalian BAD, phosphorylated at a serine at a position in the amino acid sequence of the mammalian BAD, or said fragment, corresponding to position 118 of SEQ ID NO:1, position 155 of SEQ ID NO:2, or position 113 of SEQ ID NO:3. The position of the serine is identified by alignment of the amino acid sequence of the mammalian BAD, or said fragment, to SEQ ID NO:1, SEQ ID NO:2, or SEQ ID NO:3, respectively.

More particularly, an embodiment of the present invention provides monoclonal antibodies that specifically bind to a mammalian BAD, or fragment of a mammalian BAD, phosphorylated at a serine at a position in the amino acid sequence of the mammalian BAD, or said fragment, corresponding to position 118 of SEQ ID NO:1, position 155 of SEQ ID NO:2, or position 113 of SEQ ID NO:3. The position of the serine is identified by alignment of the amino acid sequence of the mammalian BAD, or said fragment, to SEQ ID NO:1, SEQ ID NO:2, or SEQ ID NO:3, respectively.

Also more particularly, an embodiment of the present invention provides antibodies that specifically bind to a mammalian BAD, or fragment of a mammalian BAD, unphosphorylated at a serine at a position in the amino acid sequence of a mammalian BAD, or said fragment, corresponding to position 118 of SEQ ID NO:1, position 155 of SEQ ID NO:2, or position 113 of SEQ ID NO:3. The position of the serine is identified by alignment of the amino acid sequence of the mammalian BAD, or said fragment, to SEQ ID NO:1, SEQ ID NO:2, or SEQ ID NO:3, respectively.

Even more particularly, an embodiment of the present invention provides monoclonal antibodies that specifically bind to a mammalian BAD, or fragment of a mammalian BAD, unphosphorylated at a serine at a position in the amino acid sequence of a mammalian BAD, or said fragment, corresponding to position 118 of SEQ ID NO:1, position 155 of SEQ ID NO:2, or position 113 of SEQ ID NO:3. The position of the serine is identified by alignment of the amino acid sequence of the mammalian BAD, or said fragment, to SEQ ID NO:1, SEQ ID NO:2, or SEQ ID NO:3, respectively.

Another embodiment of the present invention provides polynucleotides encoding at least one isolated or synthetic polypeptide comprising an amino acid sequence of a mutant BAD, or at least one fragment of an isolated or synthetic polypeptide comprising a less than full-length amino acid sequence of a mutant BAD, having cell death promoting activity. The amino acid sequence of the encoded isolated or synthetic polypeptides of a mutant BAD, or fragment of a mutant BAD, is: 1) derived from a naturally-occurring or wild-type mammalian BAD; 2) contains a domain that is substantially identical to a BH3 domain of a naturally-occurring or wild-type mammalian BAD; and 3) does not contain a serine at a position corresponding to position 118 of SEQ ID NO:1, position 155 of SEQ ID NO:2, or position 113 of SEQ ID NO:3. The position corresponding to position 118 of SEQ ID NO:1, position 155 of SEQ ID NO:2, or position 113 of SEQ ID NO:3 is determined by alignment of the amino acid sequence of the isolated or synthetic polypeptides of the mutant BAD, or said fragments, to SEQ ID NO:1, SEQ ID NO:2, or SEQ ID NO:3, respectively.

BRIEF DESCRIPTION OF THE DRAWINGS

The foregoing and other objects of the present invention, the various features thereof, as well as the invention itself may be more fully understood from the following description, when read together with the accompanying drawings.

In a separate comparison (lower panel), cells were untreated ("−") (lane 1, lower panel), treated with Forskolin (lane 2, lower panel) or treated with Forskolin and lambda phosphatase (lane 3, lower panel) prior to lysis. Proteins were separated by SDS-PAGE. Blots were probed with an anti-BAD antibody.

Figure 8A:
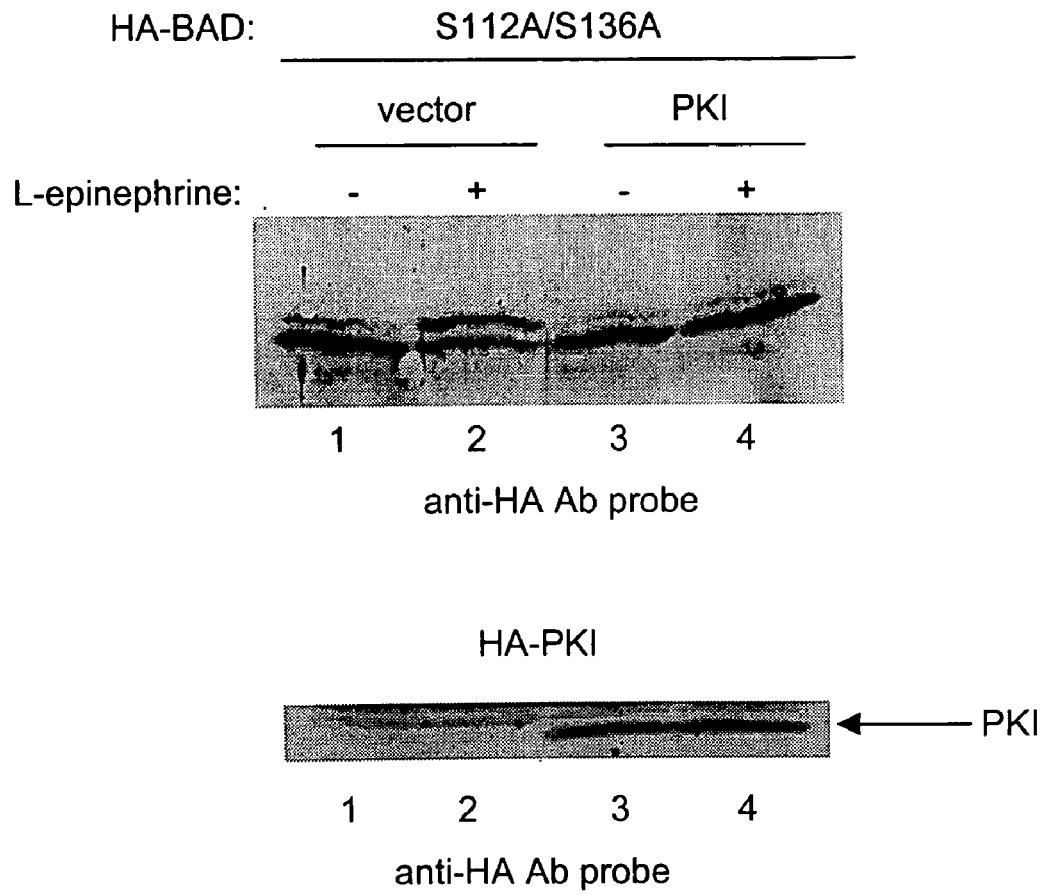

FIG. 8(A) is two western blots. HeLa cells transiently expressing HA-BAD S112A/S136A and either an empty expression vector ("vector") (lanes 1 and 2) or HA-PKI ("PKI") (lanes 3 and 4) were treated with L-epinephrine ("+") or a buffer control ("−"). Whole cell lysates were prepared and proteins were separated by SDS-PAGE. Blots were probed with an anti-HA antibody. The upper panel displays proteins corresponding, in size, to HA-BAD S112A/S136A. The lower panel displays proteins corresponding, in size, to HA-PKI.

Figure 8B:
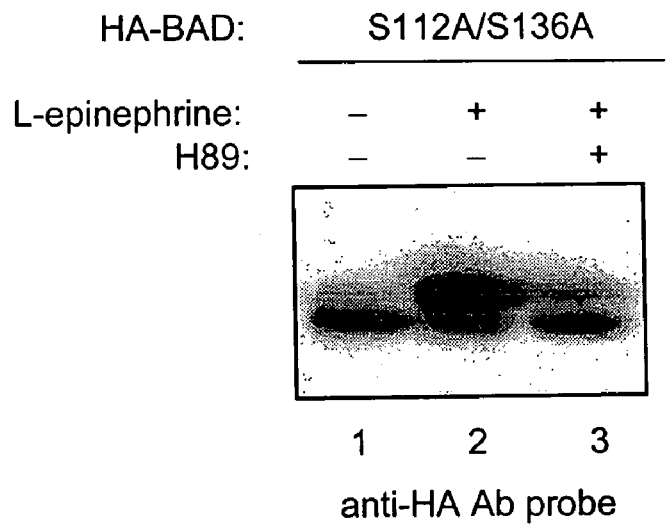

FIG. 8(B) is a western blot. Whole cell lysates were prepared from HeLa cells transiently expressing a HA-BAD S112A/S136A and untreated ("−") (lane 1), pretreated with L-epinephrine (lane 2) or pretreated with L-epinephrine and H89 (lane 3) prior to lysis. Proteins were separated by SDS-PAGE. Blots were probed with an anti-HA antibody.

Figure 9A:
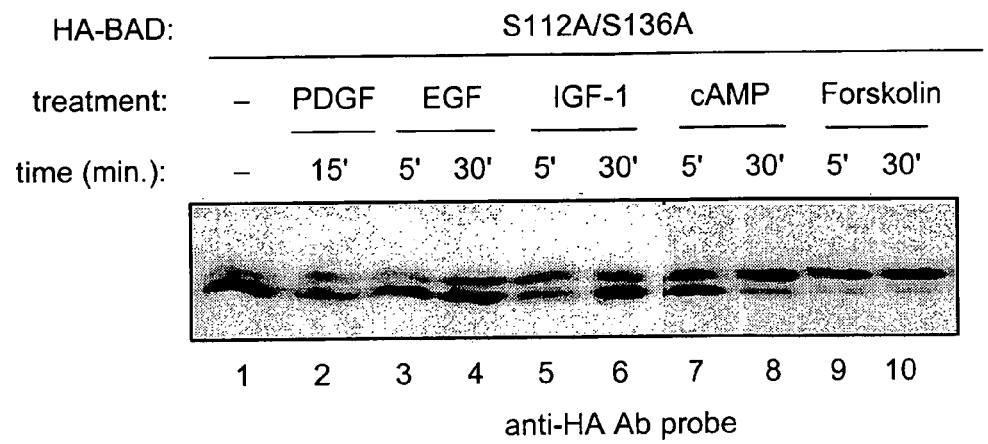

FIG. 9(A) is a western blot. Whole cell lysates were prepared from Rat-1 cells transiently expressing HA-BAD S112A/S136A, untreated ("−") (lane 1) or pretreated with platelet-derived growth factor ("PDGF") (lane 2), epidermal growth factor ("EGF") (lanes 3 and 4), insulin-like growth factor I ("IGF-1") (lanes 5 and 6), N6-benzoyl-adenosine 3',5'-cyclic monophosphate ("cAMP") (lanes 7 and 8), or Forskolin ("Forskolin") (lanes 9 and 10) prior to lysis, for the time periods indicated. Proteins were separated by SDS-PAGE. Blots were probed with an anti-HA antibody.

Figure 9B:
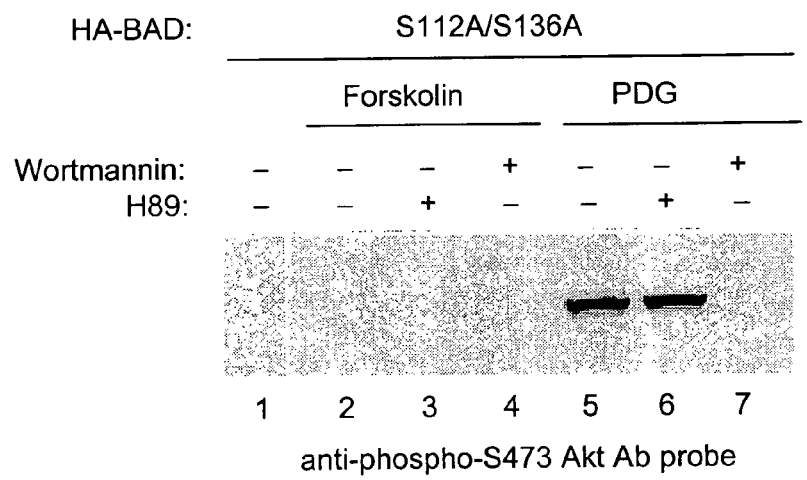
Figure 9B:
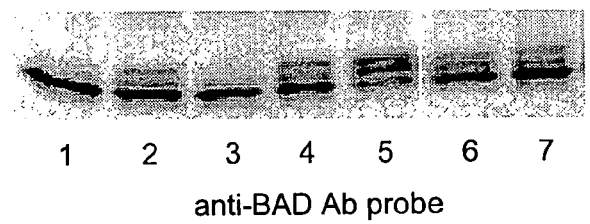

FIG. 9(B) is two western blots. Rat-1 cells transiently expressing HA-BAD S112A/S136A were treated with a buffer control, H89 (PKA inhibitor) or Wortmannin (PI 3-kinase inhibitor), prior to stimulation with Forskolin or platelet-derived growth factor ("PDGF"). Whole cell lysates were then prepared and proteins were separated by SDS-PAGE. Blots were separately probed with an anti-phospho-S473 Akt antibody (the kinase that phosphorylates Ser136) (upper panel) and an anti-BAD antibody (lower panel).

Figure 9C:
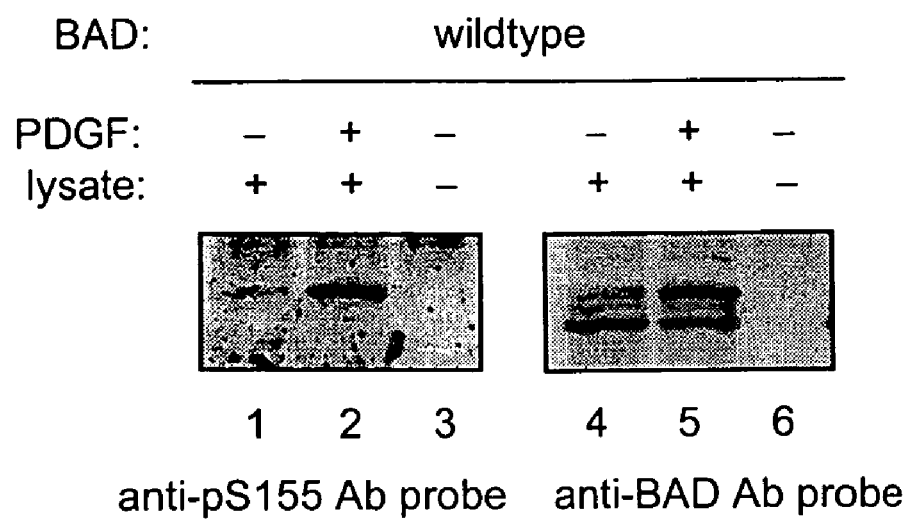

FIG. 9(C) is two western blots. Whole cell lysates were prepared from non-transfected, serum-starved, Rat-1 cells pretreated with PDGF ("+") or a buffer control ("−") prior to lysis. Endogenous BAD was immunoprecipitated from the lysates and separated by SDS-PAGE ("lysate +"). As a negative control, the anti-BAD antibody was incubated with beads without cell lysates and the collected fraction was subjected to the same anti-phospho-S155 BAD antibody analysis ("lysate −"). Blots were probed with the anti-phospho-Ser155 specific BAD antibody ("anti-pS155 Ab") (left panel) and then stripped and reprobed with an anti-BAD antibody ("anti-BAD Ab") (right panel).

Figure 10A:
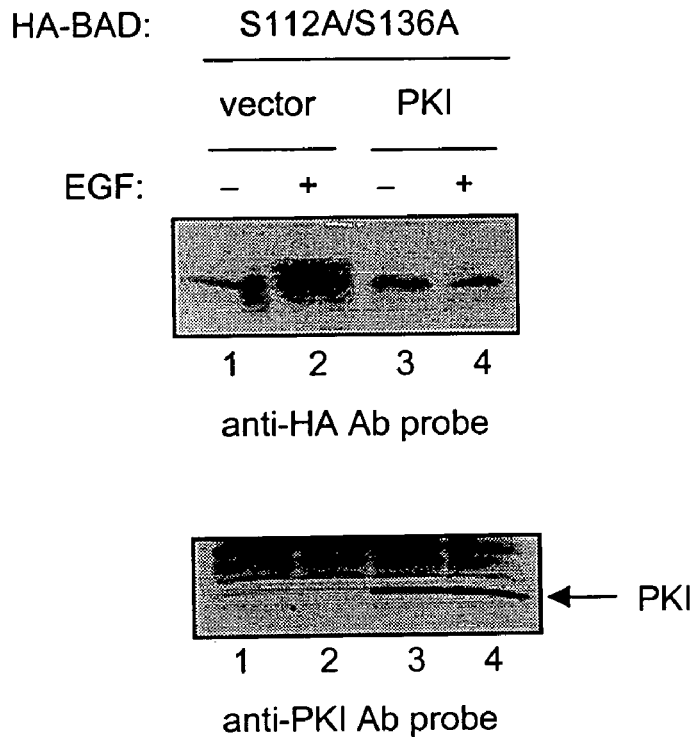

FIG. 10(A) is two western blots. Whole cell lysates were prepared from serum-starved HeLa cells co-transfected with HA-BAD S112A/S136 and either the PKI expression vector ("PKI") (lanes 3 and 4) or empty expression vector ("vector") (lanes 1 and 2), and then treated with EGF or a buffer control, prior to lysis. Proteins were separated by SDS-PAGE. Blots were probed with an anti-HA antibody (upper panel) or an anti-PKI antibody (lower panel).

Figure 10B:
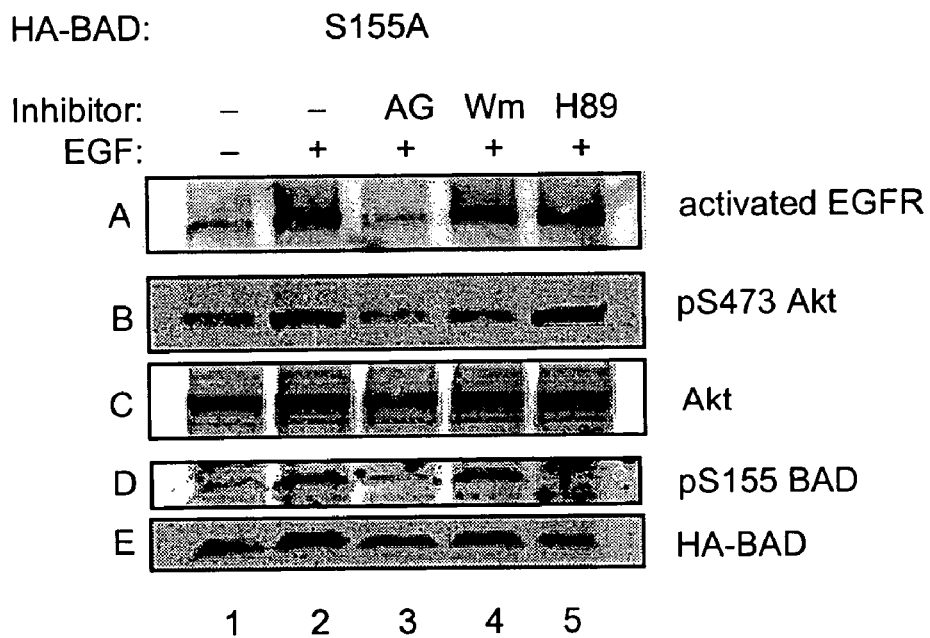

FIG. 10(B) is a series of western blots. Serum-starved HeLa cells expressing HA-BAD S155A, were pretreated with a buffer control (lanes 1 and 2), AG1478 ("AG") (lane 3), Wortmannin ("Wm") (lane 4), or H89 (lane 5). The cell cultures were then stimulated with a buffer control (lane 1) or EGF (lanes 2–5). Whole cell lysates were made from the cultures and the proteins were separated by SDS-PAGE. Blots were probed with either an anti-activated EGF receptor antibody ("activated EGFR") (panel A), an anti-phospho-S473 Akt antibody ("pS473 Akt") (panel B), or an anti-phospho-S155 BAD antibody ("pS155 BAD") (panel D). Reblots were probed with either an anti-Akt antibody ("Akt") (panel C) or an anti-HA BAD antibody ("HA-BAD") (panel E).

Figure 10C:
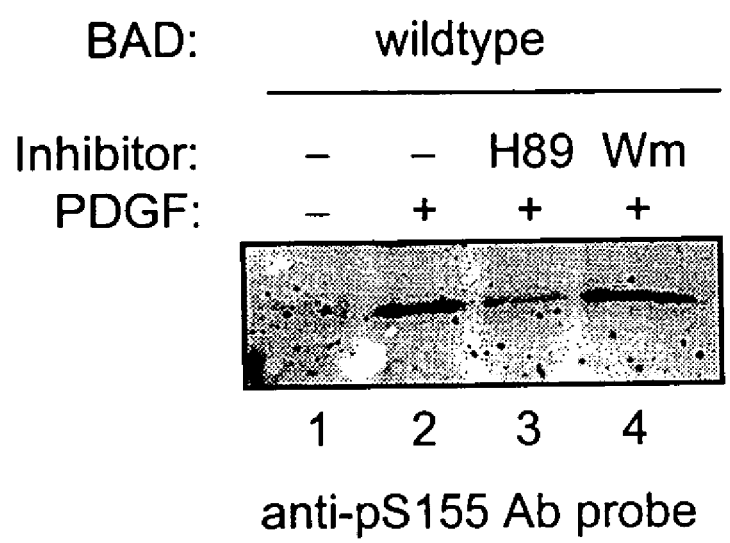

FIG. 10(C) is a western blot. Serum-starved Rat-1 cells were pretreated with a buffer control (lanes 1 and 2), H89 (lane 3) or Wortmannin ("Wm") (lane 4), followed by stimulation with PDGF. Whole cell lysates were prepared, endogenous BAD was immunoprecipitated and the resulting proteins were separated by SDS-PAGE. The blot was probed with an anti-phospho-Ser155 BAD antibody.

Figure 11A:
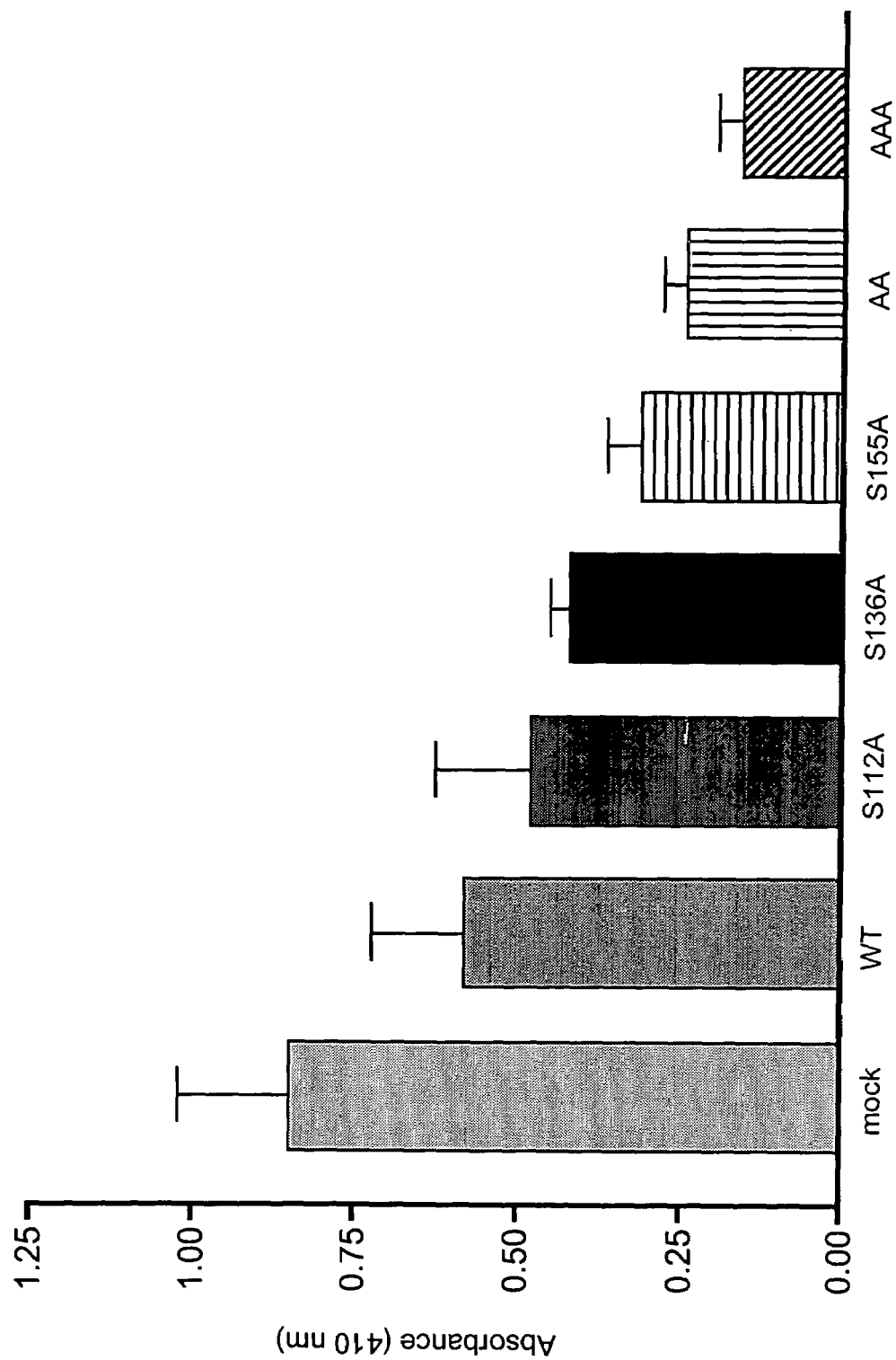

FIG. 11(A) is a graphic representation of the results of an enzyme-linked immunosorbent assay (ELISA). HeLa cells were co-transfected with β-galactosidase and one of the following: empty vector ("mock") (lane 1), wild-type BAD ("WT") (lane 2), BAD S112A ("S112A") (lane 3), BAD S136A ("S136A") (lane 4), BAD S155A ("S155A") (lane 5), BAD S112A/S136A ("AA") (lane 6), or BAD S112A/S136A/S155A ("AAA") (lane 7). Cells were treated with Forskolin four hours after co-transfection, and whole cell lysates were prepared 24 hours after co-transfection. The β-galactosidase activity was analyzed by ELISA (absorbance=410 nm).

Figure 11B:
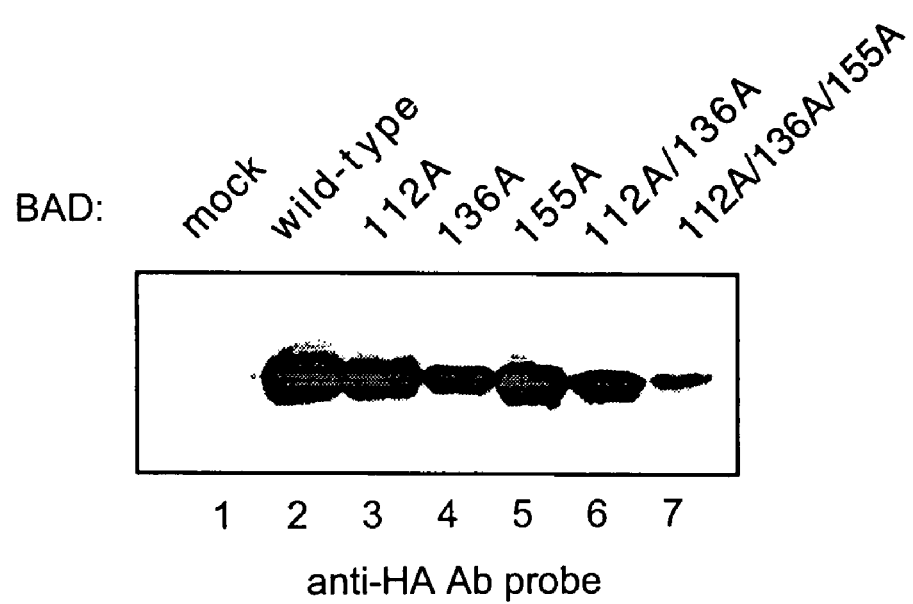

FIG. 11(B) is a western blot. Whole cell lysates were prepared as described above in FIG. 11(a). Empty vector ("mock") (lane 1), wild-type BAD ("wild-type") (lane 2), BAD S112A ("S112A") (lane 3), BAD S136A ("S136A") (lane 4), BAD S155A ("S155A") (lane 5), BAD S112A/S136A ("S112A/S136A") (lane 6), or BAD S112A/S136A/S155A ("S112A/S136A/S155A") (lane 7). Proteins were separated by SDS-PAGE. Blots were probed with an anti-HA antibody.

Figure 12A:
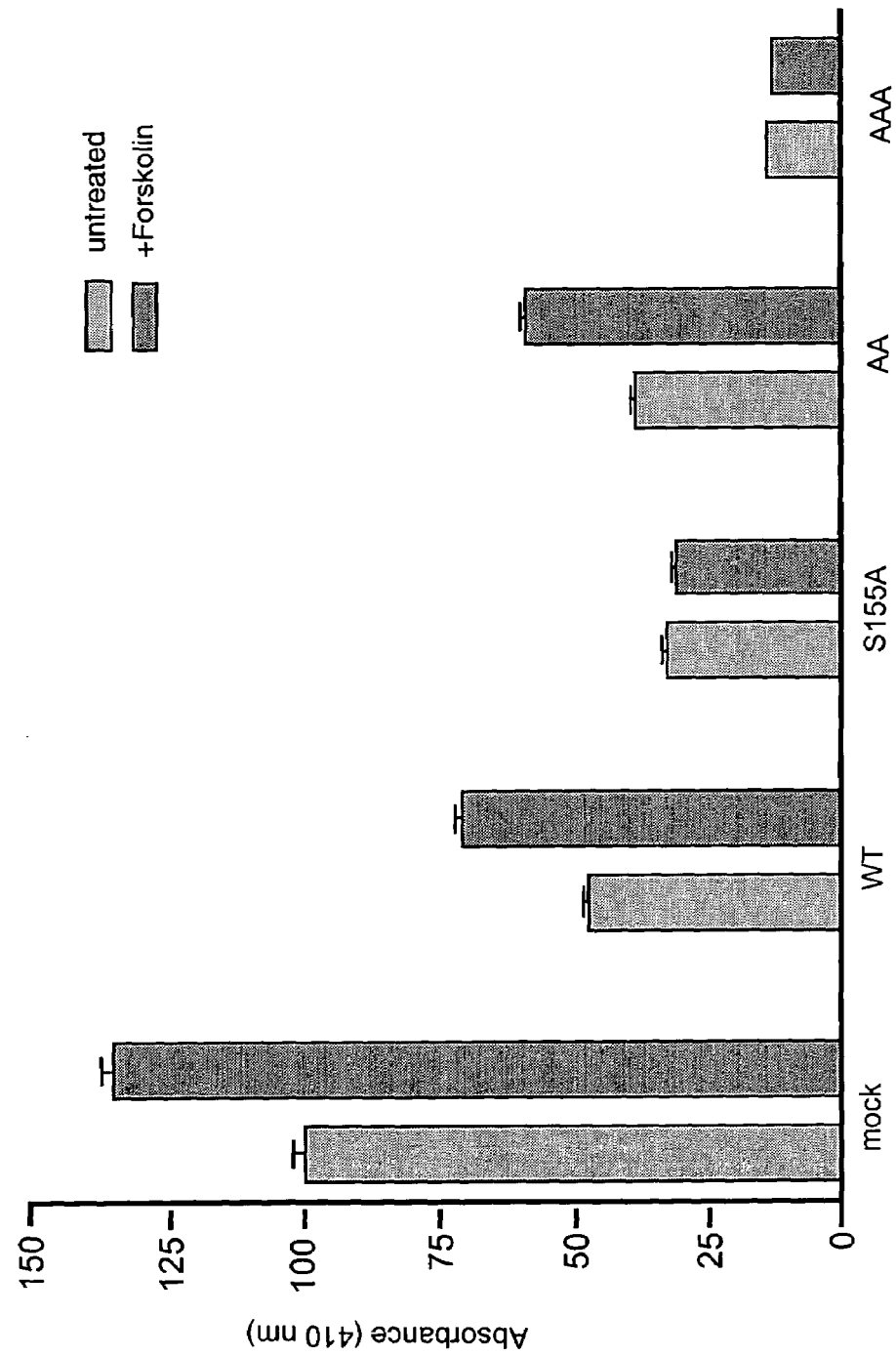

FIG. 12(A) is a graphic representation of the results of an ELISA. HeLa cells were co-transfected with β-galactosidase and one of the following: empty vector ("mock") (lanes 1 and 2), wild-type BAD ("WT") (lanes 3 and 4), BAD S155A ("S155A") (lanes 5 and 6), BAD S112A/S136A ("AA") (lanes 7 and 8), or BAD S12A/S136A/S155A ("AAA") (lanes 9 and 10). Cells were treated with Forskolin (open bars) or a buffer control (closed bars) four hours after co-transfection. Whole cell lysates were prepared 24 hours after co-transfection. The β-galactosidase activity was analyzed by ELISA (absorbance=410 nm).

Figure 12B:
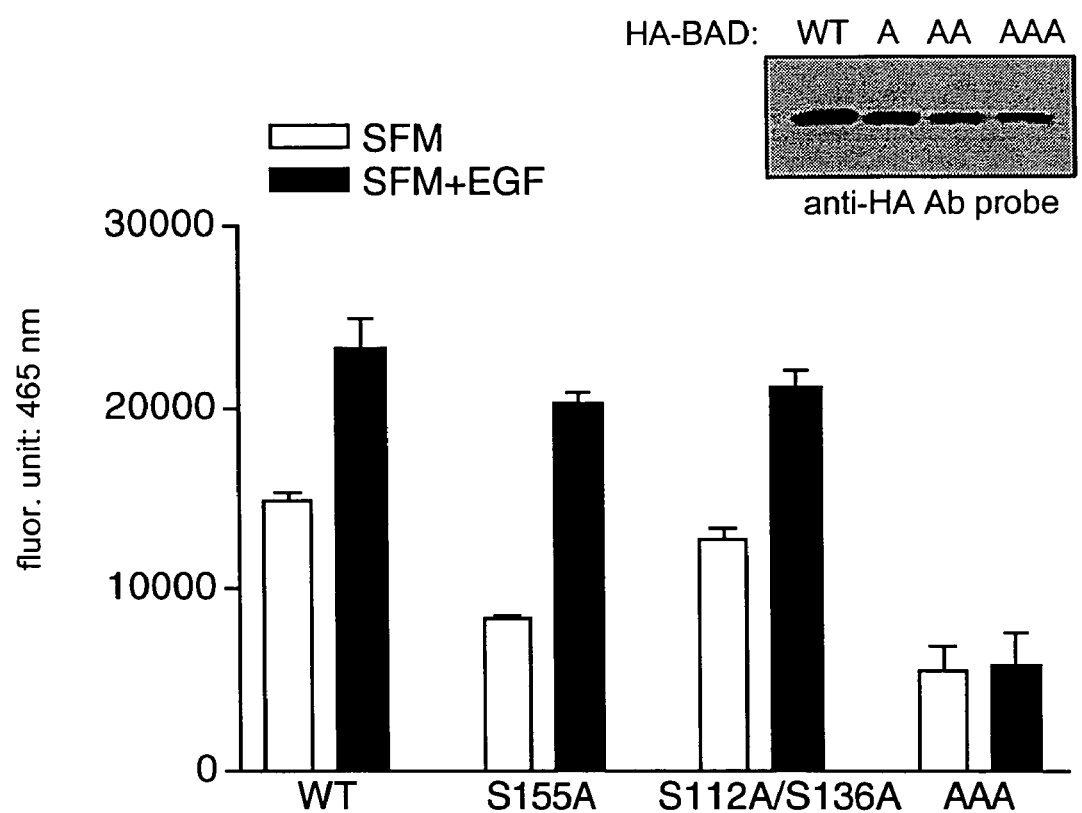

FIG. 12(B) is a graphic representation of the results of a β-galactosidase assay. HeLa cells were co-transfected with the β-galactosidase gene and either HA-BAD ("WT"), HA-BAD S155A ("S155A"), HA-BAD S112A/S136A ("S112A/S136A") or HA-BAD S112A/S136A/S155A ("AAA"). Transfected cells were then cultured in serum-free medium (SFM) or SFM supplemented with EGF (SFM+EGF) for 12 hours. Cell lysates were prepared and BAD-induced cell death was measured by the loss of β-galactosidase activity in a fluorescence-based assay. Fluorescence was measured at 465 nm. Results shown are the average and standard deviation of triplicate transfections (this experiment was repeated two more times with similar results). Expression levels of HA-tagged BAD and BAD mutants in transfected cell lysates were detected by anti-HA western blot analysis: HA-BAD ("WT"), HA-BAD S155A ("A"), HA-BAD S112A/S136A ("AA"), and HA-BAD S112A/S136A/S155A ("AAA").

Figure 12C:
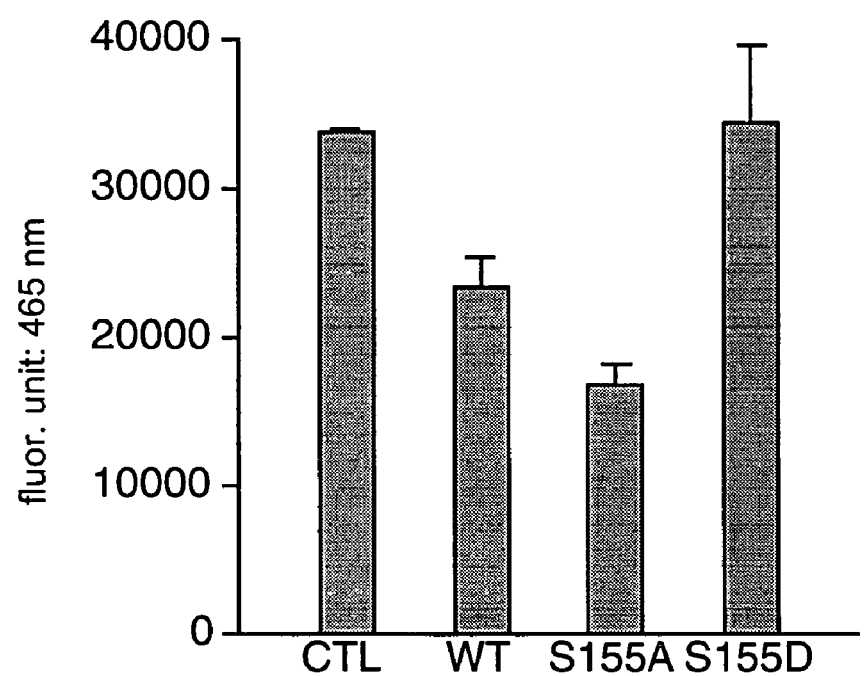

FIG. 12(C) is a graphic representation of the results of a β-galactosidase assay. HeLa cells were co-transfected with the β-galactosidase gene and either an empty vector ("CTL"), wild-type BAD ("WT"), the BAD S155A mutant ("S155A") or the BAD S155D mutant ("S155D"). Cell lysates were prepared and BAD-induced cell death was measured by the loss of β-galactosidase activity in a fluorescence-based assay. Fluorescence was measured at 465 nm. Results shown are the average and standard deviation of triplicate transfections (this experiment was repeated two more times with similar results).

Figure 13:
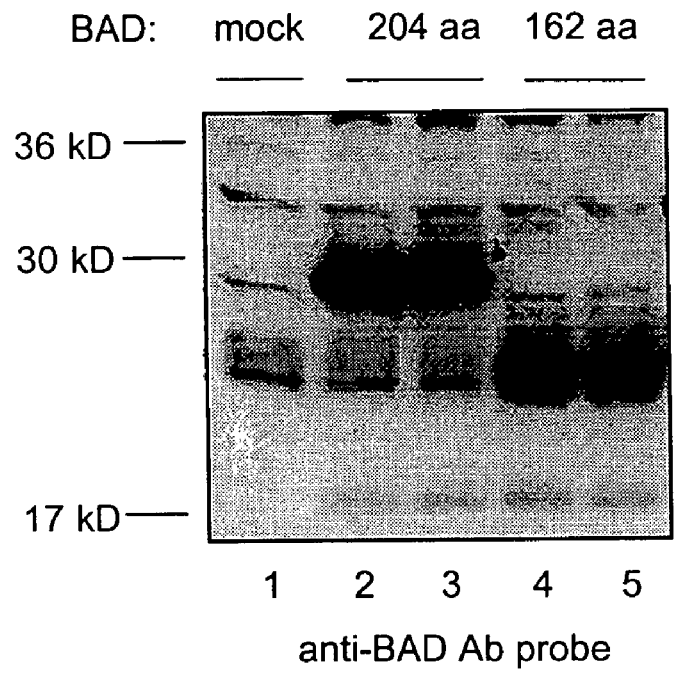
Figure 13:
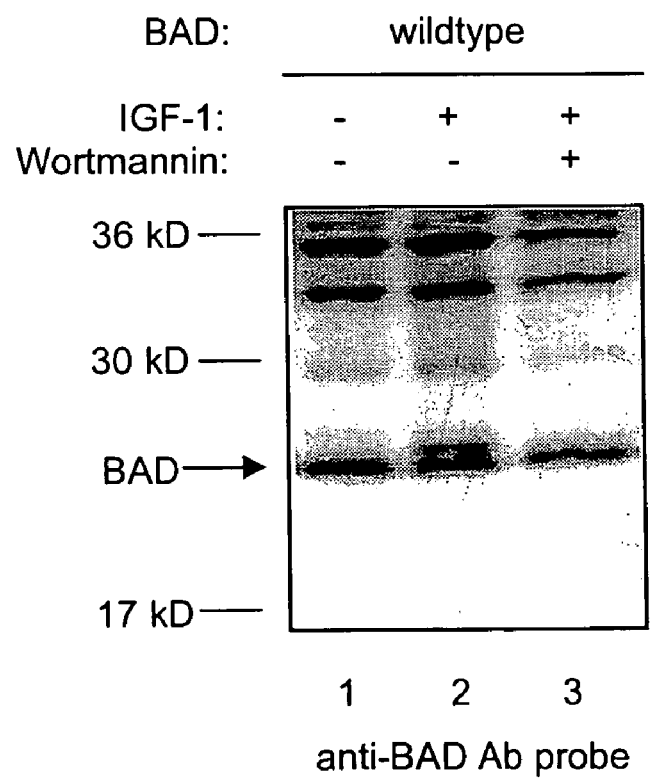

FIG. 13 is a western blot. Whole cell lysates were prepared from COS-7 cells expressing empty vector ("mock") (lane 1, upper panel), the 204 amino acid form of murine BAD (longer murine BAD) ("204 aa") (lanes 2 and 3, upper panel) or the 162 amino acid form of murine BAD (shorter murine BAD) ("162 aa") (lanes 4 and 5, upper panel). Proteins were separated by SDS-PAGE. Blots were probed with an anti-BAD antibody.

Whole cell lysates were also prepared from $FL_{5.12}$ cells expressing endogenous BAD, pretreated with IGF-1 ("+") (lanes 2 and 3, lower panel), Wortmannin ("+") (lane 3, lower panel) or a buffer control ("−") (lane 1, lower panel) prior to lysis. Proteins were separated by SDS-PAGE. Blots were probed with an anti-BAD antibody.

Figure 14:
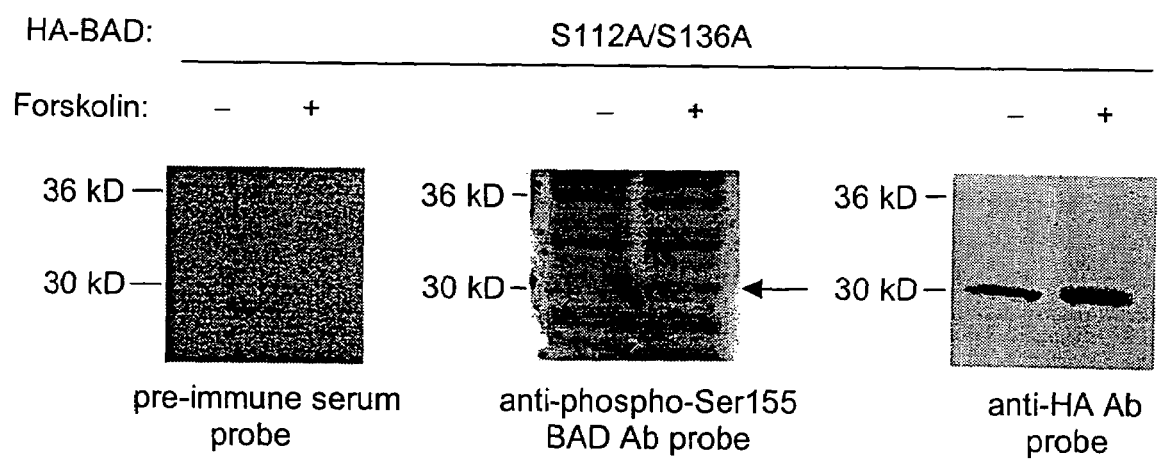

FIG. 14 is a western blot. Whole cell lysates were prepared from HeLa cells transiently expressing HA-BAD S112A/S136A, pretreated with Forskolin ("+") or a buffer control ("−") prior to lysis. Aliquots of the lysate were separated by SDS-PAGE and probed with pre-immune serum, crude rabbit anti-phospho-Ser155 BAD antibody or anti-HA antibody.

DETAILED DESCRIPTION OF THE INVENTION

The positions of amino acid residues in the sequences of BAD, mutant BAD, and fragments of a BAD or mutant BAD of the present invention are sometimes described in terms of their corresponding positions in the sequence of the human BAD of SEQ ID NO:1, murine BAD of SEQ ID NO:2 ("longer murine BAD"), and murine BAD of SEQ ID NO:3 ("shorter murine BAD"). However, since much of the published research on BAD has been performed using the murine BAD of SEQ ID NO:2, the positions of the amino acids in the sequences of BAD, mutant BAD, and fragments of BAD or mutant BAD of the present invention are sometimes described in terms of their corresponding positions in the sequence of the murine BAD of SEQ ID NO:2, for ease in understanding and cross comparing the present invention and the published works.

The amino acid sequence of the human BAD of SEQ ID NO:1 and of the murine BAD of SEQ ID NO:3 are aligned against the amino acid sequence of the murine BAD of SEQ ID NO:2 in Table 1, below, illustrating the corresponding positions of the amino acids. The serine phosphorylation sites at positions 112, 136, and 155 of SEQ ID NO:2 are denoted with an asterisk, and the corresponding positions in the amino acid sequences of SEQ ID NO:3 and SEQ ID NO:1 are given below the serine at positions 112, 136, and 155 of SEQ ID NO:2. The positions having an amino acid residue that is common between all three BAD amino acid sequences are denoted in bold.

TABLE 1

```
SEQ ID NO:2   1 MGTPKQPSLAPAHALGLRKSDPGIRSLGSDAGGRRWRPAAQSMFQIPEF
SEQ ID NO:3   1                                            MFQIPEF
SEQ ID NO:1   1                                            MFQIPEF

SEQ ID NO:2  50 EPSEQEDASATDRGLGPSLTEDQPGP          YLAPGLLGSNIHQQGRAA
SEQ ID NO:3   8 EPSEQEDASATDRGLGPSLTEDQPGP          YLAPGLLGSNIHQQGRAA
SEQ ID NO:1   8 EPSEQEDSSSAERGLGPSPAGDGPSGSGKHHRQAPGLLWDASHQQEQPT

*                                *
SEQ ID NO:2  94 TNSHHGGAGAMETRSRHSSYPAGTEEDEGMEEELSPFRGRSRSAPPNLW
SEQ ID NO:3  52 TNSHHGGAGAMETRSRHSSYPAGTEEDEGMGEELSPFRGRSRSAPPNLW
SEQ ID NO:1  57 SSSHHGGAGAVEIRSRHSSYPAGTEDDEGMGEEPSPFRGRSRSAPPNLW

*
SEQ ID NO:2 143 AAQRYGRELRRMSDEFEGSFK GLPRPKSAGTATQMRQSAGWTRIIQSW
SEQ ID NO:3 101 AAQRYGRELRRMSDEFEGSFK GLPRPKSAGTATQMRQSAGWTRIIQSW
SEQ ID NO:1 106 AAQRYGRELRRMSDEFVDSFKKGLPRPKSAGTATQMRQSSSWTRVFQSW

SEQ ID NO:2 191 WDRNLGKGGSTPSQ
SEQ ID NO:3 149 WDRNLGKGGSTPSQ
SEQ ID NO:1 155 WDRNLGRGSSAPSQ
```

* = serine phosphorylation site

The term "BAD" as used herein refers to a $Bcl-X_L$/Bcl-2 Associated Cell Death Regulator polypeptide, and includes any polypeptide of any origin that is a cell death promoter, that is substantially identical to and/or biologically equivalent to BAD, and that binds to $Bcl-X_L$ and/or Bcl-2 in competition with the cell death promoters BAX and/or BAK to inhibit the cell death repressor activity of $Bcl-X_L$ and/or Bcl-2.

The term "mutant BAD" as used herein refers to a BAD having at least an amino acid sequence in which the serine at a position corresponding to position 118 of SEQ ID NO:1, position 155 of SEQ ID NO:2, or position 113 of SEQ ID NO:3, has been replaced with an amino acid other than serine. The position of the serine, or other amino acid, corresponding to position 118 of SEQ ID NO:1, position 155 of SEQ ID NO:2, or position 113 of SEQ ID NO:3, is identified by alignment of the amino acid sequence of the mutant BAD to SEQ ID NO:1, SEQ ID NO:2, or SEQ ID NO:3, respectively.

The term "BAD mutants" as used herein refers to the plural of a "mutant BAD."

The term "fragment" as used herein refers to a polypeptide comprising an amino acid sequence of a less than full-length polypeptide. A fragment contains at least 10 amino acids, more preferably at least 25 amino acids, and can approach the number of amino acids in the full-length polypeptide. Further, a fragment of the present invention is characterized as having biological activity such as, e.g., cell death promoting activity and/or the ability to bind to Bcl-$X_L$ and/or Bcl-2.

Examples of a fragment are a fragment of a BAD and a fragment of a mutant BAD. A fragment of a BAD comprises an amino acid sequence of a less than full-length BAD. Preferably, a fragment of a BAD contains a domain substantially identical to a BH3 domain of a naturally-occurring or wild-type mammalian BAD, wherein the amino acid sequence of the fragment has a serine at a position corresponding to position 118 of SEQ ID NO:1, position 155 of SEQ ID NO:2, or position 113 of SEQ ID NO:3. A fragment of a mutant BAD comprises an amino acid sequence of a less than full-length mutant BAD. Preferably, a fragment of a mutant BAD contains a domain substantially identical to a BH3 domain of a naturally-occurring or wild-type mammalian BAD, wherein the amino acid sequence of the fragment of a mutant BAD has an amino acid other than serine at a position corresponding to position 118 of SEQ ID NO:1, position 155 of SEQ ID NO:2, or position 113 of SEQ ID NO:3. The position of the amino acid corresponding to position 118 of SEQ ID NO:1, position 155 of SEQ ID NO:2, or position 113 of SEQ ID NO:3, is identified by alignment of the amino acid sequence of the fragment to SEQ ID NO:1, SEQ ID NO:2, or SEQ ID NO:3, respectively.

The terms "naturally-occurring" or "wild-type" as used herein refer to a polynucleotide or polypeptide that can be found in nature and is present in an organism (including viruses) although not necessarily in a discrete or isolated form, which can be isolated from a source in nature and which has not been intentionally modified by man in the laboratory.

The term "BH3 domain" as used herein refers to the amino acids comprising from approximately residue 143 to residue 168 of the murine BAD of SEQ ID NO:2, or any portion thereof, or any sequence of amino acids that corresponds to this sequence when aligned with the murine BAD of SEQ ID NO:2, or any portion thereof.

The BAD, mutant BAD, and fragments of a BAD or mutant BAD of the present invention in one embodiment are provided in an isolated form. The term "isolated" as used herein refers to the fact that the object species such as a BAD, mutant BAD, or fragment of a BAD or mutant BAD, is substantially free of other substances which are not the object species, i.e. not in a natural environment. Generally, a substantially pure composition will comprise more than about 80 to 90 percent of all macromolecular species present in the composition. Most preferably, the object species is purified to essential homogeneity such that contaminant species cannot be detected in the composition by standard methods of detection and wherein the composition consists essentially of a single macromolecular species. Solvent species, small molecules (<500 Daltons), and elemental ion species are not considered macromolecular species.

The BAD, mutant BAD, and fragments of BAD or mutant BAD of the present invention may be derived from any naturally-occurring or wild-type BAD native to any tissue or species. Similarly, the biological activity, e.g., cell death promoting activity and/or binding to Bcl-$X_L$ and/or Bcl-2, of such BAD, mutant BAD, and fragments of BAD or mutant BAD, can be characterized using any number of biological assay systems known to those skilled in the art.

The terms "activity that promotes apoptosis" and "cell death promoting activity" as used herein mean functional activity of a protein, such as BAD, mutant BAD, and fragments of BAD or mutant BAD of the present invention, that induces, instigates, causes or triggers apoptosis or cell death, or the signal transduction pathway that leads to apoptosis or cell death.

The term "monitoring indicia of apoptosis" as used herein means examining culture cells, whether by assay or visual inspection, for one or more of loss of cellular junctions and microvilli, cytoplasmic condensation and nuclear chromatin margination, nuclear fragmentation, cytoplasmic contraction, mitochondrial and ribosomal compaction, endoplasmic reticulum dilation and fusion with the plasma membrane, and cellular break up into membrane-bound apoptotic bodies (Wyllie, 1980).

The term "biologically equivalent" as used herein means that the BAD, mutant BAD, or fragments of a BAD or mutant BAD, of the present invention are capable of demonstrating some or all of the same biological activity of a naturally-occurring or wild-type BAD, e.g., cell death promoting activity, and/or binding to Bcl-$X_L$ and/or Bcl-2, although not necessarily to the same degree as the naturally-occurring or wild-type BAD. The biological activity of a BAD, mutant BAD, or fragment of a BAD or mutant BAD, of the present invention can be determined using assays known to those skilled in the art. For example, the percent viability of cells expressing a BAD, mutant BAD, or fragment of a BAD or mutant BAD, of the present invention can be monitored as an indication of the cell death promoting activity of the expressed polypeptide. A mutant BAD, or fragment of the mutant BAD, can show increased or decreased cell death promoting activity compared to, for example, the naturally-occurring or wild-type BAD from which the mutant BAD, or fragment of the mutant BAD, was derived, depending upon the particular mutant.

The terms "percent sequence identity," "percent identity," "% sequence identity," or "% identity" as used herein are intended to mean the percentage of the same residues or nucleotides between two or more amino acid sequences or nucleic acid sequences, respectively (Higgins et al., 1992). The percentage of the same residues or nucleotides between multiple amino acid or nucleic acid sequences can be determined by aligning the amino acid or nucleic acid sequences, respectively, using sequence analysis software such as, for example, the Lasergene biocomputing software (DNASTAR, Inc., Madison, Wis.). The amino acid residue weight table used for the Lasergene alignment program is PAM250 (Dayhoff et al., 1978). Sequence alignment allows identification of regions of sequence homology, such as, for example, the BH3 domain and, in particular, it allows identification of the serine, or other amino acid, at a position corresponding to the serine at position 118 of SEQ ID NO:1, position 155 of SEQ ID NO:2, and position 113 of SEQ ID NO:3.

The term "substantially identical" as used herein is intended to mean that there is at least 75%, preferably 85%, and more preferably 90 to 95% identity between two or more amino acid sequences or between two or more nucleotide sequences, and preferably the amino acid sequence includes a BH3 domain, or the nucleotide sequence encodes a BH3 domain.

Reference to a mutant BAD herein preferably includes a mutant BAD having an amino acid sequence that is substantially identical to at least one of SEQ ID NO:1, SEQ ID NO:2, or SEQ ID NO:3.

Preferably, reference to a mutant BAD herein includes a mutant BAD having an amino acid sequence with at least 85 percent sequence identity with at least one of SEQ ID NO:1, SEQ ID NO:2, or SEQ ID NO:3.

More preferably, reference to a mutant BAD herein includes a mutant BAD having an amino acid sequence with at least 90–95 percent sequence identity with at least one of SEQ ID NO:1, SEQ ID NO:2, or SEQ ID NO:3.

The BAD, mutant BAD, and fragments of BAD and mutant BAD, of the present invention can also include synthetic, derivative, heterologous, hybrid, fusion, and modified forms of such polypeptides. The different forms of such polypeptides include forms in which certain amino acids have been deleted, added, replaced, or substituted; one or more amino acids has/have been changed to an amino acid analogue; and/or there are glycosylations of such polypeptides. Such polypeptides are characterized as having biological activity, e.g., cell death promoting activity and/or the ability to bind to Bcl-$X_L$ and/or Bcl-2. Furthermore, in the case of a BAD, mutant BAD, or fragment of a BAD or mutant BAD, having an amino acid substitution at a position corresponding to the serine at position 118 of SEQ ID NO:1, 155 of SEQ ID NO:2, or 113 of SEQ ID NO:3, such biological activity may be blocked by the phosphorylation of the amino acid at such a corresponding position.

The polynucleotides of the present invention encoding BAD, mutant BAD, or a fragment of BAD or mutant BAD include, for example, isolated or synthetic DNA, genomic DNA, mRNA, and cDNA. The isolated polynucleotides may be isolated, for example, through hybridization with the complementary sequence of genomic, subgenomic DNA, cDNA, or mRNA encoding BAD, mutant BAD, or fragments of BAD or mutant BAD. The polynucleotides may encode BAD, mutant BAD, or fragments of BAD or mutant BAD, having substituted serine residues and/or phosphorylated serine residues. It will also be appreciated by one skilled in the art that degenerate DNA sequences can encode BAD, mutant BAD, or fragments of BAD or mutant BAD having serine substitutions or having serines which can be phosphorylated. Also intended to be included within the present invention are those polynucleotides encoding allelic variants of BAD and serine substituted and/or serine phosphorylated derivatives of such BAD.

Polynucleotides of the present invention encoding a BAD, mutant BAD, or fragment of a BAD or mutant BAD, may include sequences that facilitate RNA transcription (expression sequences) and protein translation of the coding sequences, such that the encoded polypeptide product is produced. Methods for construction of such polynucleotides are known to those skilled in the art and are described, for example, in Sambrook et al., Molecular Cloning, 2nd Ed., Cold Spring Harbor Laboratory Press, 1989. For example, such polynucleotides may include a promoter, a transcription termination site, polyadenylation site, ribosome binding site, an enhancer for the use in eukaryotic expression hosts, and/or, optionally, sequences necessary for replication of a vector. A typical eukaryotic expression vector may include a polynucleotide sequence encoding a BAD, mutant BAD, or fragment of a BAD or mutant BAD, inserted in-frame and downstream of a promoter such as, e.g., the herpes simplex virus thymidine kinase ("HSV-tk") promoter or the phosphoglycerate kinase ("pgk") promoter, optionally linked in-frame to an enhancer and a downstream polyadenylation site (e.g., the SV40 large T polyadenylation site).

The degeneracy of the genetic code gives a finite set of polynucleotide sequences encoding these amino acid sequences of the BAD, mutant BAD, and fragments of the BAD or mutant BAD of the present invention. This set of degenerate sequences may be readily generated by one skilled in the art, by hand or by computer using commercially available software. Isolated polynucleotides encoding a BAD, mutant BAD, or fragment of a BAD or mutant BAD, are typically less than approximately 10,000 nucleotides, more preferably less than approximately 3,000 nucleotides, still more preferably less than approximately 1,500 nucleotides, and most preferably approximately 600 nucleotides.

Preferred polynucleotides are those polynucleotides encoding a mutant BAD, or fragment of a mutant BAD, having an amino acid sequence that is substantially identical to SEQ ID NO:1, SEQ ID NO:2, or SEQ ID NO:3.

Preferred polynucleotides also include those polynucleotides capable of hybridizing, under stringent conditions, with a polynucleotide encoding a naturally-occurring or wild-type mammalian BAD. Such stringent conditions are known to, and/or can be determined by standard methods, by those skilled in the art. Examples of such stringent conditions are provided in Sambrook et al., 1989. Such polynucleotides may be further screened, under the stringent conditions described above, to select for polynucleotides that do not hybridize to polynucleotides encoding any other members of the Bcl-2 family. Such selective hybridization can be performed using standard cross-hybridization tests known to those skilled in the art.

Polynucleotides encoding a fragment of a BAD or mutant BAD of the present invention may be short oligonucleotides, for example oligonucleotides that are 20–100 nucleotides in length, wherein such oligonucleotides have biological activity, for example, have cell death promoting activity and/or the ability to bind to Bcl-$X_L$ and/or Bcl-2.

Polynucleotides encoding a BAD, mutant BAD, or fragment of a BAD or mutant BAD of the present invention may also comprise part of a larger polynucleotide, such as, for example, a cloning vector. Also, such polynucleotides encoding a BAD, mutant BAD, or fragment of a BAD or mutant BAD, of the present invention may be fused in-frame, by polynucleotide linkage, to another polynucleotide sequence encoding a different polypeptide such as, for example, a polynucleotide encoding a heterologous polypeptide such as the Tat polypeptide (YGRKKRRQR-RRG) (SEQ ID NO:20) which facilitates intracellular delivery of the BAD, mutant BAD, or fragment of the BAD or mutant BAD. Similarly, the encoded polypeptide can be a fusion polypeptide, such as, for example, a BAD, mutant BAD, or fragment of a BAD or mutant BAD, fused to a heterologous polypeptide such as, for example, the Tat polypeptide (YGRKKRRQRRRG) (SEQ ID NO:20).

Typically, the polynucleotides encoding a mutant BAD, or fragment of a mutant BAD, comprise at least 25 consecutive nucleotides which are substantially identical to the polynucleotide sequence encoding a naturally-occurring or wild-type mammalian BAD and encoding a codon for an amino acid substitution of the serine at a position corresponding to position 118 of SEQ ID NO:1, 155 of SEQ ID NO:2, or 113 of SEQ ID NO:3. More preferably the polynucleotides encoding a mutant BAD, or fragment of a mutant BAD, comprise at least 50 to 100 consecutive nucleotides, and still more preferably at least 500 to 550 consecutive nucleotides, which are substantially identical to the polynucleotide sequence encoding a naturally-occurring or wild-type mammalian BAD and encoding an amino acid substitution of the serine at a position corresponding to position 118 of SEQ ID NO:1, 155 of SEQ ID NO:2, or 113 of SEQ ID NO:3.

Additionally, a polynucleotide encoding a mutant BAD, or fragment of a mutant BAD, can be used to construct transgenes for expressing such polypeptides at high levels, and/or under the transcriptional control of transcription control sequences which do not naturally occur adjacent to a naturally-occurring or wild-type Bad gene. For example, a constitutive promoter (e.g., a HSV-tk or pgk promoter) or a cell-lineage specific transcriptional regulatory sequence (e.g., a CD4 or CD8 gene promoter/enhancer) or tissue-specific transcriptional regulatory sequence may be operably linked to a polynucleotide encoding a mutant BAD, or fragment of a mutant BAD, to form a transgene (typically in combination with a selectable marker such as, e.g., a neo gene expression cassette). Such transgenes can be introduced into cells, such as hematopoietic stem cells and transgenic cells, and transgenic nonhuman animals can be obtained according to standard methods known to those skilled in the art. Transgenic cells and/or transgenic nonhuman animals may be used to generate models of diseases involving overexpression or inappropriate expression of BAD and to screen for agents to treat such diseases as, for example, immunodeficiency diseases, including AIDS, senescence, neurodegenerative disease, ischemic and reperfusion cell death, infertility, wound-healing, and the like. Polynucleotides encoding a BAD, or fragment of a BAD, can also be used to construct, express, and use a transgene in the same manner as described above for a mutant BAD, or fragment of a mutant BAD.

In another embodiment the present invention provides a method for producing a mutant BAD, or fragment of a mutant BAD, with increased cell death promoting activity, relative to a corresponding wild-type BAD or mutant BAD (i.e. one having the same sequence except for the particular amino acid changes) or with the ability to modulate cell death promoting activity. The method comprises preparation of a mutant BAD, or fragment of a mutant BAD, having an amino acid substitution at a serine at a position corresponding to position 118 of SEQ ID NO:1, position 155 of SEQ ID NO:2, or position 113 of SEQ ID NO:3. The mutant BAD, or fragment of a mutant BAD, can be made based upon the complete or partial sequence of a BAD from any source, for example a mammalian BAD such as the BAD of SEQ ID NO:1, SEQ ID NO:2, or SEQ ID NO:3. The position of the serine, or other amino acid, at a position corresponding to position 118 of SEQ ID NO:1, position 155 of SEQ ID NO:2, or position 113 of SEQ ID NO:3 is identified by alignment of the sequence of the mutant BAD, or fragment of a mutant BAD, with SEQ ID NO:1, SEQ ID NO:2, or SEQ ID NO:3, respectively. Such a mutant BAD, or fragment of a mutant BAD, can be prepared using standard methods known to those skilled in the art.

For example, a mutant BAD, or fragment of a mutant BAD, may be made by expression of the DNA sequence encoding the mutant BAD, or fragment of a mutant BAD, in a suitable transformed host cell. Using methods well known in the art, the DNA encoding the mutant BAD, or fragment of a mutant BAD, can be prepared and inserted into an expression vector, transformed into a host cell, and suitable conditions established for expression of the mutant BAD, or fragment of the mutant BAD, in the transformed cell. A BAD, or fragment of a BAD, can also be produced and expressed in the same manner described above for the mutant BAD, and fragment of a mutant BAD.

Any suitable expression vector may be employed to produce a recombinant BAD, mutant BAD, or fragment of a BAD or mutant BAD, such as, for example, the mammalian expression vector pCB6 (Brewer, 1994) or the E. coli pET expression vectors, for example, pET-30a (Studier et al., 1990). Other suitable expression vectors for expression in mammalian and bacterial cells that are known in the art are, for example, expression vectors for use in yeast or insect cells. For example, Baculovirus vectors and expression systems can be employed. A BAD, mutant BAD, or fragments of a BAD or mutant BAD, can also be prepared by chemical synthesis, by expression in in vitro translation systems using a polynucleotide template, or by isolation from biological samples. Chemical synthesis of a polypeptide can be performed, for example, by the classical Merrifeld method of solid phase peptide synthesis (Merrifield, 1963), or by the FMOC strategy on a Rapid Automated Multiple Peptide Synthesis System (DuPont Company, Wilmington, Del.) (Caprino and Han, 1972). Fragments, analogs, and modified forms of a BAD or mutant BAD can also be constructed or synthesized using methods well known in the art.

The terms "analog," "mutein," or "mutant" as used herein refer to polypeptides which are comprised of a segment of at least 10 amino acids that have substantial identity to a portion of the sequence of a naturally-occurring or wild-type polypeptide, for example, a naturally-occurring or wild-type BAD. Typically, analog polypeptides comprise a conservative amino acid substitution (or addition or deletion) with respect to a naturally-occurring or wild-type polypeptide sequence, or a mutant polypeptide, for example, the serine-substituted mutant BAD or fragment of a mutant BAD of the present invention. Analogs typically are at least 20 amino acids long, preferably at least 50 amino acids long or longer up to the length of a full-length naturally-occurring or wild-type polypeptide.

The discovery of the inhibitory effect of the phosphorylation of BAD on the binding of BAD to Bcl-$X_L$ and/or Bcl-2 provides a new site for intervention in the modulation of apoptosis or programmed cell death. Such intervention can involve the administration of, for example, a mutant BAD, fragment of a mutant BAD, analog of a BAD, or fusion thereof, having an amino acid other than serine at a position corresponding to position 118 of SEQ ID NO:1, position 155 of SEQ ID NO:2, or position 113 of SEQ ID NO:3, and preferably, having an amino acid sequence that is substantially identical to SEQ ID NO:1, SEQ ID NO:2, or SEQ ID NO:3, respectively.

Modulation of the phosphorylation of BAD within a cell can be accomplished by altering the intracellular phosphorylation state of BAD. The phosphorylation state of many polypeptides is dynamically controlled by both protein kinases and protein phosphatases (Cohen, 1989). The present work shows that both protein kinases and protein phosphatases can alter the phosphorylation state of BAD.

Phosphatases that dephosphorylate serine residues in polypeptides have been extensively studied and both inhibitors and activators have been reported (for reviews, see Wera and Hemmings, 1995; Shenolikar, 1995). Thus, either inhibitors or activators can be used to modulate, increase, or decrease, including diminish, the ability of intracellular phosphatase to remove the phosphate from the serine at a position corresponding to position 118 of SEQ ID NO:1, position 155 of SEQ ID NO:2, or position 113 of SEQ ID NO:3. Many phosphatase inhibitors and activators are known and these can be readily screened by one skilled in the art for activity, for example, by determining the effect of a test agent on the in vitro or in vivo cleavage, by phosphatase activity, of a radiolabeled phosphate group from the serine at position corresponding to position 118 of SEQ ID NO:1, position 155 of SEQ ID NO:2, or position 113 of SEQ ID NO:3 (see, e.g., Matthews, 1995; Shenolikar, 1995). It is preferred that the inhibitors and activators have selective actions on the phosphatase(s) acting upon the BAD, or fragments of BAD, of the present invention.

Similarly, inhibitors and activators of protein kinases are known and can be used as therapeutic agents (see, e.g., Levitski, 1994). Thus, either kinase inhibitors or activators can act to modulate, increase, or decrease, including diminish, the action of intracellular kinases which phosphorylate a BAD, or fragment of a BAD, at a serine at a position corresponding to position 118 of SEQ ID NO:1, position 155 of SEQ ID NO:2, or position 113 of SEQ ID NO:3. It is preferred that the inhibitors and activators have selective actions on the kinase(s) acting upon the BAD, or fragment of BAD, of the present invention. It has been demonstrated that kinases act selectively and that neither phosphokinase C (PKC) nor RAF1 could phosphorylate BAD, in vitro, at the serine at position 118 of SEQ ID NO:1, position 155 of SEQ ID NO:2, and position 113 of SEQ ID NO:3. However, heart muscle kinase (HMK), a form of phosphokinase A, could phosphorylate BAD, in vitro, at the serine at position 118 of SEQ ID NO:1, position 155 of SEQ ID NO:2, and position 113 of SEQ ID NO:3. Thus, inhibitors and activators effective in modulating, increasing, or decreasing, including diminishing, the phosphorylation state of BAD could be tested for their effect on BAD phosphorylation in vitro using HMK, for example, as a selective serine kinase that phosphorylates a serine at a position corresponding to position 118 of SEQ ID NO:1, position 155 of SEQ ID NO:2, or position 113 of SEQ ID NO:3. Alternatively, in vivo testing could be done using a number of experimental approaches, and one example, as reported herein, utilizes the endogenous phosphorylation of BAD upon re-addition of IL-3 after withdrawal for two hours. Such standard testing systems could be used to test candidate compounds as inhibitors or activators of BAD phosphorylation. PMA promotes BAD phosphorylation, whereas staurosporin inhibits BAD phosphorylation.

It may be desirable to modulate or decrease, including diminish, the amount of BAD that is able to bind to Bcl-$X_L$ and/or Bcl-2 in the cells. Such as in the treatment of diseases involving overexpression or inappropriate expression of BAD, or the active form of BAD, at any level for which decreasing the amount of BAD can interfere with apoptosis and promote cell survival. In such disease conditions, treatments to modulate or decrease, including diminish, non-phosphorylated BAD can be used. Such treatments can involve administration of BAD serine phosphatase inhibitors or selective serine kinase activators that phosphorylate the serine at a position corresponding to position 118 of SEQ ID NO:1, 155 of SEQ ID NO:2, and/or 113 of SEQ ID NO:3 to decrease the ability of BAD to bind to Bcl-$X_L$ and/or Bcl-2. Such treatment would be useful in diseases such as, for example, immunodeficiency diseases, senescence, neurodegenerative disease, ischemic cell death, reperfusion cell death, infertility and wound-healing.

Conversely, in the treatment of diseases involving underexpression or inappropriately low levels of active BAD, it may be desirable to modulate and increase the amount of BAD that is able to bind to Bcl-$X_L$ and/or Bcl-2 in the cells. In such disease conditions, treatments to modulate or increase the non-phosphorylated, active BAD can be used. Such treatments can involve administration of BAD serine phosphatase activators or inhibitors of kinase that phosphorylate the serine at a position corresponding to position 118 of SEQ ID NO:1, position 155 of SEQ ID NO:2, and/or position 113 of SEQ ID NO:3 to increase the ability of BAD to bind to Bcl-$X_L$ and/or Bcl-2. Such treatments would be useful in diseases such as, for example, cancer, viral infections, lymphoproliferative conditions, arthritis, infertility, inflammation and autoimmune diseases.

The BAD, mutant BAD, and fragments of BAD or mutant BAD, of the present invention can be prepared by chemical synthesis; in recombinant cells transformed with a polynucleotide encoding at least one of such polypeptides; by expression in in vitro translation systems using a polynucleotide template encoding at least one of such polypeptides; or by isolation of such polypeptides from biological samples. Phosphorylation of one or more amino acid residues, such as to produce the phosphorylated serine-containing polypeptides of the present invention, can be accomplished by well known methods in the art. For example, the amino acid residue(s) can be phosphorylated prior to polypeptide synthesis. In other methods the amino acid(s) is phosphorylated after synthesis of the polypeptide, such as in the case when a kinase such as HMK is used.

Derivatives of the BAD, mutant BAD, fragments of BAD or mutant BAD, and/or phosphorylated forms of such polypeptides, of the present invention can include non-peptide substances possessing the biological properties of the BAD, mutant BAD, fragments of BAD or mutant BAD, and/or phosphorylated forms of such polypeptides, in inducing and/or promoting an apoptotic state and/or binding to Bcl-$X_L$ or Bcl-2. The techniques for making peptide mimetics are well known to those skilled in the art (see, e.g., Navia and Peattie, 1993; Olson et al., 1993). Typically, making peptide mimetics involves identification and characterization of the polypeptide target site as well as the polypeptide ligand using X-ray crystallography and nuclear magnetic resonance. For example, the amino acid sequence of two murine BAD (SEQ ID NO:2 and SEQ ID NO:3) and a human BAD (SEQ ID NO:1), containing a BH3 domain and containing a phosphorylation site at the serine at position 155 of SEQ ID NO:1, position 118 of SEQ NO:2, and position 113 of SEQ ID NO:3, respectively, has been identified. Using this information along with computerized molecular modeling, a pharmacophore hypothesis can be developed and compounds can be made and tested in an assay system as described herein or known in the art.

The BAD, mutant BAD, and fragment of BAD or mutant BAD, of the present invention can also be used to detect new polypeptides as well as non-peptide compositions capable of associating with or binding to Bcl-$X_L$ and/or Bcl-2 and thereby acting as inhibitors to the binding of BAD to Bcl-$X_L$ and/or Bcl-2, for example, by using a standard radioligand assay system (see, e.g., Bylund and Toews, 1993). Such inhibitors could serve to remove any apoptotic inducing or modulating effect that the binding of BAD to Bcl-$X_L$ and/or Bcl-2 might have. In one embodiment, the inhibitors can be polypeptides that also contain the conserved serine residues as described above, including BAD, or a fragment of BAD. It is also possible to utilize as inhibitory polypeptides having a modified or substituted amino acid or non-amino acid residue at a position corresponding to position 118 of SEQ ID NO:1, position 155 of SEQ ID NO:2, and/or position 113 of SEQ ID NO:3, for example, in place of a serine residue, such that the polypeptide containing the modified amino acid or non-amino acid residue functions in the same way as dephosphorylated BAD, in that it binds to Bcl-$X_L$ and/or Bcl-2, and thereby displaces BAD.

The radioligand assays useful in screening for inhibitors of the binding of BAD to Bcl-$X_L$ and/or Bcl-2 can involve preparation of a radiolabeled form of BAD, mutant BAD, or fragment of BAD or mutant BAD, capable of binding to Bcl-$X_L$ and/or Bcl-2 using, for example, either a $^3$H or $^{125}$I according to standard methods. For example, the Bolton Hunter Reagent can be used (ICN Chemicals, Radioisotope Division, Irvine, Calif.). The radiolabeled BAD ligand binds to the Bcl-$X_L$ and/or Bcl-2 immobilized to a substrate such as in a standard ELISA-style plate assay. The amount of bound and/or free radiolabeled ligand is then measured (see, e.g., Slack et al., 1989; Dower et al., 1989). Alternatively, the Bcl-$X_L$ and/or Bcl-2 can be radiolabeled and the BAD, mutant BAD, or fragment of BAD or mutant BAD, immobilized to a substrate. In a variation of this approach, the binding assay is performed with soluble, non-immobilized BAD, mutant BAD, or fragments of BAD or mutant BAD, and Bcl-$X_L$ and/or Bcl-2. Competitive inhibition of the binding of the radiolabeled BAD ligand to Bcl-$X_L$ and/or Bcl-2 on addition of a test compound can be evaluated by standard methods of analysis (see, e.g., Rovati, 1993).

The present invention also includes therapeutic or pharmaceutical compositions comprising an active agent which is: a phosphatase inhibitor or activator; a kinase inhibitor or activator; or a BAD, mutant BAD, fragment of a BAD or mutant BAD; or a phosphorylated BAD, mutant BAD, or fragment of a BAD; for treating diseases or disease conditions in which the propensity for cell death can be advantageously modulated, and methods of making and using such compositions. These compositions and methods are useful for treating a number of diseases such as, for example, neoplasia, certain viral infections (e.g., Epstein-Barr virus), lymphoproliferative conditions, arthritis, inflammation, autoimmune diseases and the like resulting from an inappropriate decrease in cell death as well as diseases such as, for example, immunodeficiency diseases, senescence, neurodegenerative disease, ischemic cell death, reperfusion cell death, infertility, wound-healing and the like resulting from an inappropriate increase in cell death. Treatment can also involve administration to affected cells ex vivo.

The therapeutic or pharmaceutical compositions of the present invention can be administered by any suitable route known in the art including for example intravenous, subcutaneous, intramuscular, transdermal, intrathecal or intracerebral or administration to cells in ex vivo treatment protocols. Administration can be either rapid as by injection or over a period of time as by slow infusion or administration of a slow release formulation. For treating tissues in the central nervous system, administration can be by injection or infusion into the cerebrospinal fluid (CSF). When it is intended that the active agent be administered to cells in the central nervous system, administration can be with one or more agents capable of promoting penetration of the active agent across the blood-brain barrier (see, e.g., Friden et al., 1993). Furthermore, BAD, mutant BAD, fragments of BAD or mutant BAD, and serine-phosphorylated forms of such polypeptides, can be stably linked to a polymer such as polyethylene glycol to obtain desirable properties of solubility, stability, half-life and other pharmaceutically advantageous properties (see, e.g., Davis et al., 1978; Burnham, 1994).

Furthermore, the active agent can be in a composition which aids in delivery into the cytosol of a cell. For example, the peptide may be conjugated with a carrier moiety such as a liposome that is capable of delivering the peptide into the cytosol of a cell. Such methods are well known in the art (see, e.g., Amselem et al., 1993). Alternatively, the active agent can be modified to include specific transit peptides or fused to such transit peptides which are capable of delivering the BAD, mutant BAD, or fragment of BAD or mutant BAD, of the present invention into a cell. In addition, such polypeptides can be delivered directly into a cell by microinjection.

The phosphatase inhibitors and activators, and kinase inhibitors and activators, can also be linked or conjugated with agents that provide desirable pharmaceutical or pharmacodynamic properties as described above, such as the coupling of the active substance to a compound which promotes penetration or transport across the blood-brain barrier or stably linking the active substance to a polymer to obtain desirable properties of solubility, stability, half-life and the like.

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. The active agent can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

Dose administration can be repeated depending upon the pharmacokinetic parameters of the dosage formulation and the route of administration used.

It is also contemplated that certain formulations containing the active agent may be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in light of the relevant circumstances including the condition or conditions to be treated, the choice of composition to be administered, the age, weight, and response of the individual patient, the severity of the patient's symptoms, and the chosen route of administration. Whereas typically the patient as referenced herein is human, nevertheless, the formulations and methods herein can be suitably prepared and used for veterinary applications in addition to human applications and the term "patient" as used herein is intended to include human and veterinary patients.

In a number of circumstances it would be desirable to determine the level of a phosphorylated BAD with respect to the non-phosphorylated BAD in a cell. This would provide an assessment of the apoptotic status of the cell and allow the design of a rational treatment program designed to change the level and/or ratio of phosphorylated to non-phosphorylated BAD. A high level of non-phosphorylated BAD, or a high ratio of non-phosphorylated BAD to phosphorylated BAD, might indicate an increase in apoptotic activity in the cell, or progression of the state of apoptosis in the cell, and could indicate the need for treatment to decrease the non-phosphorylated BAD, or the ratio of non-phosphorylated BAD to phosphorylated BAD. Conversely, low levels of non-phosphorylated BAD or a low ratio of non-phosphorylated BAD to phosphorylated BAD could indicate the need to increase either the non-phosphorylated BAD or the ratio of non-phosphorylated BAD to phosphorylated BAD.

Furthermore, in the treatment of disease conditions, compositions containing BAD can be administered exogenously and it would likely be desirable to achieve certain target levels of BAD, as well as a ratio of non-phosphorylated to phosphorylated BAD in sera, in any desired tissue compartment or in the affected cells or tissue. It would, therefore, be advantageous to be able to monitor the levels of non-phosphorylated and phosphorylated BAD in a patient or in a biological sample, including a tissue biopsy sample obtained from a patient and, in some cases, it might also be desirable to monitor the level of other members of the Bcl-2 family, including Bcl-$X_L$ and/or Bcl-2. Accordingly, the present invention also provides methods for detecting the presence of BAD, and the ratio of non-phosphorylated to phosphorylated BAD, in a cell or a population of cells or in a sample from a patient.

The term "detection" as used herein, in the context of detecting the presence of non-phosphorylated and phosphorylated BAD in a patient, is intended to include the ability to determine the amount of, or distinguish, non-phosphorylated and phosphorylated BAD; to determine the amount of, or distinguish from other polypeptides, expressed and/or post-translationally modified BAD; distinguish non-phosphorylated and phosphorylated forms of BAD from each other, and from other members of the Bcl-2 family; estimate the probable outcome of a disease involving non-phosphorylated and phosphorylated BAD; estimate the prospect for recovery; determine the level of non-phosphorylated and phosphorylated BAD over a period of time as a measure of the status of a disease or condition; and/or monitor the phosphorylated and non-phosphorylated level of BAD for determining a preferred therapeutic regimen for the patient.

To detect the presence and level of non-phosphorylated and phosphorylated BAD in a cell or population of cells or patient, a sample is obtained from the population of cells or from the patient. The sample can be a population of cells, a tissue biopsy sample, a sample of blood, or a cell fraction from blood, plasma or the like. When the sample is from a patient any of a variety of tissues known to express BAD can serve as the source of cells for testing as can a sample or biopsy from a diseased tissue such as a neoplasia. When assessing peripheral levels of BAD, the sample can be a sample of cells obtained from blood or a cell-free sample such as plasma or serum.

The present invention further provides for methods to detect the presence of the non-phosphorylated and phosphorylated forms of BAD in a sample obtained from a patient. Any method known in the art for detecting proteins can be used. Such methods include, but are not limited to immunodiffusion, immunoelectrophoresis, immunochemical methods, binder-ligand assays, immunohistochemical techniques, agglutination and complement assays (for example see Sites and Terr, eds., 1991). Preferred are binder-ligand immunoassay methods, including reacting antibodies with an epitope or epitopes of BAD and competitively displacing a labeled BAD or derivative thereof. The measurement of levels of phosphorylated BAD can be by any of a variety of methods. A particularly useful method based on the work described herein would involve the determination of the amount of phosphorylated BAD bound to Bcl-$X_L$ and/or Bcl-2. This can be done by immunoprecipitation and western blot analysis using, for example, anti-BAD, anti-serine-phosphorylated-BAD, anti-Bcl-$X_L$, and/or anti-Bcl-2 antibodies, all of which can be prepared by known methods. In addition, recombinant BAD tagged with the hemagglutinin ("HA") epitope can be immunoprecipitated or probed on a western blot using anti-HA antibody. Also, recombinant BAD tagged with a glutathione S-transferase ("GST") moiety can be precipitated using glutathione beads. Alternatively, serine-phosphorylated and -unphosphorylated BAD can be determined by using anti-BAD and anti-serine-phosphorylated-BAD antibodies in an immunoassay method as described below.

Such methods of detection described above can also be used to detect the phosphorylation state and/or the presence of a mutant BAD, or fragment of a BAD or mutant BAD, including a recombinant form thereof.

Polyclonal antibodies can be prepared by immunizing rabbits or other animals by injecting antigen followed by subsequent boosts at appropriate intervals. The animals are bled and sera assayed against the purified BAD, mutant BAD, or fragments of the BAD or mutant BAD of the present invention, usually by enzyme-linked immunosorbent assay (ELISA) or by bioassay based upon the ability to accelerate apoptosis in cells. Monoclonal antibodies can be prepared by methods known in the art, such as by the method of Milstein and Kohler by fusing splenocytes from immunized mice with continuously replicating tumor cells such as myeloma or lymphoma cells (Milstein and Kohler, 1975; Gulfre and Milstein, 1981). The hybridoma cells formed in this manner are then cloned by limiting dilution methods and the supernatants assayed for antibody production ELISA, radioimmunoassay (RIA), or bioassay.

Numerous competitive and non-competitive polypeptide binding immunoassays are well known in the art. Antibodies employed in such assays may be unlabeled, for example as used in agglutination tests, or labeled for use in a wide variety of assay methods. Labels that can be used include, for example, radionucleides, enzymes, fluorescers, chemiluminescers, enzyme substrates or co-factors, enzyme inhibitors, particles, dyes and the like for use in RIA, enzyme immunoassays, e.g., ELISA, fluorescent immunoassays and the like. Polyclonal or monoclonal antibodies directed against a BAD, mutant BAD, a fragment of a BAD or mutant BAD, or an epitope thereof, can be made for use in immunoassays by any of a number of methods known in the art.

Immunoprecipitating BAD heterodimers from cells expressing BAD and other polypeptides that bind to BAD, for example, members of the Bcl-2 family, including Bcl-$X_L$, and Bcl-2, can be accomplished by methods well known in the art. For example, a polynucleotide encoding a BAD can be inserted into a plasmid expression vector encoding the GST moiety and the amino acid sequence of the heart muscle kinase (HMK) phosphorylation target sequence, so that the encoded BAD is operably linked, in-frame, to the GST moiety and HMK target sequence. Cells, for example E. coli, can then be transformed with such a plasmid vector and produce a BAD which is fused to a GST moiety and the HMK target sequence. The resulting polypeptide can be purified after overexpression in E. coli by standard methods, for example, using GST agarose beads. The purified GST-BAD can then be labeled in vitro, for example, with $\gamma$-$^{32}$P-ATP and heart muscle kinase to produce radiolabeled, phosphorylated GST-BAD.

Such methods for immunoprecipitation as described above can also be used to immunoprecipitate heterodimers in cells expressing a mutant BAD, or fragments of a BAD or mutant BAD, and polypeptides that bind to such a mutant BAD, or fragments of a BAD or mutant BAD, and forming heterodimers.

An expression library, such as a cDNA expression library, can then be screened with the radiolabeled, phosphorylated GST-BAD for clones that produce a polypeptide which binds to the GST-BAD (see Neilsen, 1991). The identified clone can then be isolated and the DNA sequence of the clone determined by standard methods known in the art. One skilled in the art would know how to predict the amino acid sequence of a potential BAD from the DNA sequence of the clone (Muslin et al., 1996).

Such methods for screening, cloning, and sequencing as described above can also be applied to phosphorylate and screen with a radiolabeled mutant BAD, or fragment of a BAD or mutant BAD.

For metabolic labeling, cells can be labeled, for example, either in phosphate-free media (e.g., RPMI 1640 media) with $^{32}$P-orthophosphate (e.g., 1 mCi/10$^6$ cells) or in methionine-free media (e.g., RPMI 1640 media) with $^{35}$S-methionine (e.g., 200 mCi/10$^6$ cells). The cells can then be lysed (e.g., in either in 137 mM NaCl, 20 mM Tris (pH 8.0), 1.5 mM MgCl$_2$, 1 mM EDTA, 50 mM NaF, 0.2%–0.5% NP40 containing aprotinin (0.15 U/ml), 20 mM leupeptin, and 1 mM phenylmethysulfonyl fluoride) for co-immunoprecipitation, or for direct immunoprecipitation (in RIPA buffer). The lysates are first cleared, for example, with protein A beads (e.g., 30 min), followed by incubation with an antibody (e.g., 1.5 hour, on ice). The antibody complexes are then captured with protein A beads (e.g., 1 hour). The immunoprecipitate is then washed (e.g., with 0.2% NP-40 lysis buffer), resuspended in loading buffer, and separated by SDS-PAGE. The gel is then treated, for example, with fluorography and visualized by autoradiography, or transferred to a nitrocellulose membrane for further immunoblot analysis. For western blots, lysates are separated by SDS-PAGE, and transferred, typically, to a nitrocellulose membrane. The membrane is first blocked with a milk solution (e.g., 3% milk solution, 1 hour), followed by incubation with primary and secondary antibodies (e.g., for one hour each), and finally developed by enhanced chemiluminescence using, for example, a commercially available kit (e.g., a kit supplied by Amersham Pharmacia Biotech, Piscataway, N.J.).

Plasmids capable of expressing a fusion polypeptide comprising a naturally-occurring or wild-type BAD, mutant BAD, or fragment of a BAD or mutant BAD; or a fusion polypeptide capable of binding to a BAD, mutant BAD, or fragment of a BAD or mutant BAD, for example, Bcl-$X_L$ or Bcl-2, can be constructed by inserting a polynucleotide encoding the amino acid sequence of at least one of such polypeptides into an expression vector. A fusion polypeptide can be constructed, for example, by inserting a polynucleotide encoding the amino acid sequence of a first polypeptide into an expression vector containing a polynucleotide encoding the amino acid sequence of a second polypeptide, such that the amino acid sequence of the first polypeptide is in-frame with, and operably linked to the amino acid sequence of the second polypeptide. For example, the amino acid sequence of a BAD, mutant BAD, or fragment of a BAD or mutant BAD, can be operably linked to the amino acid sequence of the HA epitope. In this manner a plasmid is constructed that is capable of expressing a fusion polypeptide that comprises a BAD, mutant BAD, or fragment of a BAD or mutant BAD, that is tagged with the HA epitope. Using the same approach, plasmids capable of expressing a fusion polypeptide that comprises a polypeptide that can bind to a BAD, mutant BAD, or fragment of a BAD or mutant BAD, and is operably linked with the HA epitope or other polypeptide, can be constructed. Examples of polypeptides that bind to BAD are Bcl-$X_L$ and Bcl-2. Also, plasmids capable of expressing a naturally-occurring or wild-type BAD, or polypeptide that binds to a naturally-occurring or wild-type BAD, can be constructed by inserting a polynucleotide encoding the amino acid sequence of at least one of such polypeptides into an expression vector. The methods and vectors for constructing such plasmids are well known to those skilled in the art.

Using standard methods known in the art, cells (e.g., FL$_{5,12}$ cells) can be transformed (e.g., using electroporation) with the expression plasmid containing the fusion polypeptide. More particularly, cells can be co-transformed with a plasmid capable of expressing a BAD, mutant BAD, or fragment of a BAD or mutant BAD, and another plasmid capable of expressing a polypeptide capable of binding to a BAD, mutant BAD, or fragment of a BAD or mutant BAD. Thereafter, (e.g., forty-eight hours after transformation) a limited dilution of the cells can be performed in selection medium (e.g., in medium containing G418). Single-cell clones, expressing the polypeptide encoded by the polynucleotide contained in the plasmid used to transform the cells and detected by western blot analysis, can be selected several days later (e.g., 7–10 days later). Lysates from cells expressing the fusion polypeptide can be analyzed by immunoprecipitation and/or western blot analysis using, for example, anti-BAD antibody, anti-HA antibody, anti-Bcl-$X_L$, and/or anti-Bcl-2 antibody.

The phosphorylation of a BAD, mutant BAD, or fragment of a BAD or mutant BAD, can be detected in vivo, for example, by radiolabeling the BAD, mutant BAD, or fragment of a BAD or mutant BAD expressed in cells. The cells are first transformed with a plasmid capable of expressing BAD, mutant BAD, or fragment of a BAD or mutant BAD, and then, using standard methods, the polypeptides expressed in the transformed cells are labeled, for example, with $^{32}$P-orthophosphate. Thereafter, the cells are lysed and the BAD, mutant BAD, or fragment of a BAD or mutant BAD, expressed in the transformed cells can be immunoprecipitated with, for example, anti-BAD antibody, resolved on an SDS-PAGE gel, and analyzed, for example, by fluorography. Alternatively, a sample of the labeled cell lysate can be analyzed by western blot with an anti-BAD antibody. In particular, the serine phosphorylation of a BAD, mutant BAD, or fragment of a BAD or mutant BAD can be detected, in vivo, using the methods described above.

$^{32}$P-radiolabeled BAD, mutant BAD, or fragment of a BAD or mutant BAD, bound to another polypeptide, for example, Bcl-$X_L$ or Bcl-2, can be immunoprecipitated from cells expressing BAD, mutant BAD, or a fragment of a BAD or mutant BAD, and a polypeptide that binds to BAD, mutant BAD, or fragment of a BAD or mutant BAD as described above. Using standard protocols known to those skilled in the art, the immunoprecipitated BAD, mutant BAD, or fragment of a BAD or mutant BAD, can then be treated with phosphatase.

For example, protein A-BAD complexes can be suspended in an appropriate buffer (e.g., 500 ml of 40 mM PIPES piperazine-N,N'-bis(2-thansulfonic acid) buffer (pH 6.0) containing 1 mM DTT, aprotinin (0.15 U/ml), 20 mM leupeptin, and 1 mM phenylmethysulfonyl fluoride) and treated with a commercially available phosphatase (e.g., potato acid phosphatase, Sigma). Samples containing phosphatase inhibitors can be supplemented with, for example, 50 mM sodium fluoride, 5 mM sodium phosphate, 10 mM sodium pyrophosphate, 10 mM ammonium molybdate, 5 mM EDTA and 5 mM EGTA. The protein A beads can then be pelleted by centrifugation, washed (e.g., with NP-40 lysis buffer), resuspended in a gel loading buffer, and the bound proteins can be examined by western blot analysis. BAD can resolve on a gel as a doublet; phosphorylated BAD resolves as a higher molecular weight band relative to unphosphorylated or dephosphorylated BAD, which migrates as a lower molecular weight relative to phosphorylated BAD. Treatment of immunoprecipitated BAD with potato acid phosphatase (PAP) can eliminate the higher molecular weight band by converting the higher molecular weight phosphorylated BAD to the lower molecular weight dephosphorylated BAD.

The immunoprecipitated $^{32}$P-radiolabeled BAD, mutant BAD, or fragment of a BAD or mutant BAD can be separated by SDS-PAGE and transferred to a nitrocellulose membrane. Membrane slices containing either the phosphorylated, dephosphorylated or unphosphorylated BAD, mutant BAD, or fragment of a BAD or mutant BAD, can be isolated from the membrane, and digested with trypsin under appropriate conditions. Standard methods known to those skilled in the art can be used to isolate the nitrocellulose membrane-bound BAD, mutant BAD, or fragment of a BAD or mutant BAD, and digest it with commercially available trypsin (e.g., Worthington Biochemicals). The peptides resulting from the trypsin digest can then be dried, washed, hydrolyzed, and resolved by TLC, using standard methods known to those skilled in the art (see Boyle et al., 1991). The location of phosphoamino acids can then be determined, for example, by ninhydrin staining and autoradiography. Phosphoamino acid analysis of the BAD doublet revealed that BAD was exclusively phosphorylated at serine residues.

Using methods well known in the art, for example, using two-dimensional tryptic peptide mapping, it is possible to identify the specific amino acids and their positions in the amino acid sequence of a BAD, mutant BAD, or fragment of a BAD or mutant BAD, that were phosphorylated in vivo. For example, by generating two dimensional tryptic peptidic maps of a BAD the precise sites of serine phosphorylation can be identified. After the BAD is immunoprecipitated from $^{32}$P-orthophosphate labeled cells, separated by SDS-PAGE, transferred to a nitrocellulose membrane, and enzymatically digested with trypsin, the tryptic peptides can be separated, horizontally, in the first dimension (e.g., in pH 8.9 buffer; see Boyle et al., 1991) by TLC (e.g., utilizing a HTLE-7000 apparatus and electrophoresing for 30 minutes at 1000 V at 4° C.). Separation in the second dimension can performed by ascending chromatography (e.g., in 37.5% n-butanol, 25% pyridine and 7.5% acetic acid for 10 hours). The $^{32}$P-phosphopeptides can then be visualized by autoradiography and the non-radiolabeled phosphopeptides can be visualized, for example, with ninhydrin staining. The labeled peptides can then be eluted (e.g., in pH 1.9 buffer) from the TLC plates, conjugated to membrane (e.g., Sequelon-AA membrane (Perspective Biosystem, Framingham, Mass.), using methanol:water:triethylamine:phenylisothiocyanate, in a 7:1:1:1 ratio, at 55° C.). The eluted peptides can then be either directly applied onto a TLC plate or treated with performic acid to uniformly oxidize the peptides before application to the TLC plate. The peptides are then separated according to charge in the first dimension, followed by hydrophobicity in the second dimension, as above. The 2D maps of the upper and lower molecular bands, representing phosphorylated and unphosphorylated or dephosphorylated BAD species can then be resolved. The resolved $^{32}$P-labeled tryptic peptides can then be subjected to manual Edman degradation performed as previously described (Boyle et al., 1991; Luo, et al., 1991) and the identity and position of the specific amino acids in the BAD amino acid sequence determined.

EXAMPLES

Preferred embodiments of the invention are described in the following examples. The Examples provide exemplary guidance for practicing the various aspects of the invention described above. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims that follow the examples. Unless otherwise indicated, all parts, percents and ratios are by volume.

Additional details for methods employed herein and normally used in the art can be found, for example, in the cited references. The inventions described herein are useful for investigating and controlling apoptosis events, including situations where apoptosis is desirably enhanced and situations where apoptosis is desirably inhibited. Specific utilities and applications are apparent to the ordinary skilled artisan.

Example 1

Phosphorylation of BAD at a Novel Site Renders BAD Unable to Associate with Bcl-X$_L$ In order to study the role of BAD phosphorylation in the regulation of tumor cell survival, mammalian expression vectors encoding the shorter murine BAD of SEQ ID NO:3 or a mutant BAD derived from the shorter murine BAD of SEQ ID NO:3 were constructed, wherein the amino acid sequence of the mutant BAD contained an amino acid substitution at the serine at a position corresponding to the serine at position 112 ("Ser112") and/or position 136 ("Ser136") of SEQ ID NO:2. The mutant BAD S112A has an amino acid sequence wherein the serine at a position corresponding to Ser112 is substituted with alanine; the mutant BAD S136A has an amino acid sequence wherein the serine at a position corresponding to Ser136 is substituted with alanine; and the mutant BAD S112A/S136A has an amino acid sequence wherein the serines at positions corresponding to both Ser112 and Ser136 are substituted with alanine.

Figure 1:
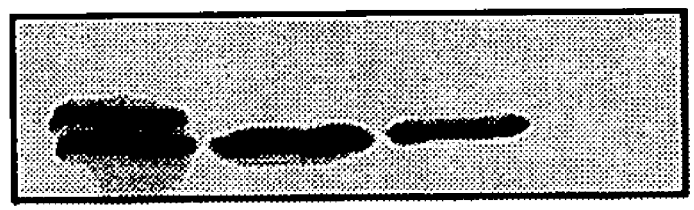
FIG. 1 is a western blot. Whole cell lysates were prepared from COS-7 cells transiently expressing the double mutant HA-BAD S112A/S136A. Lysates were treated ("+") with lambda phosphatase or a buffer control ("−") (lanes 1 and 2). Separate aliquots of the lysate were incubated with GST-Bcl-$X_L$ ("+") or a buffer control ("−") and precipitated with glutathione beads (lanes 3 and 4). Proteins were separated by SDS-PAGE. Blots were probed with an anti-HA antibody.

Mouse FL$_{5.12}$ cells were then transfected with the expression vector encoding the shorter murine BAD of SEQ ID NO:3 or one of the three BAD mutants. Total mRNA was isolated from the transfected FL$_{5.12}$ cells, and reverse transcribed into cDNA. The cDNA was then subcloned into the expression vector pcDNA3 so that the amino acid sequence of the BAD or mutant BAD, encoded by the subcloned cDNA, was in-frame and operably linked to an N-terminal hemagglutinin ("HA") epitope encoded by the expression vector. The expression vectors encoding the HA-tagged shorter murine BAD and mutant BAD were expressed in COS-7 cells. Whole cell lysates ("WCL") were then prepared from the COS-7 cells expressing the polypeptides. The phosphorylation of the shorter murine BAD of SEQ ID NO:3 and mutant BAD were detected by a western blot of the WCL, probed with an anti-HA antibody ("anti-HA antibody"). Consistent with previous observations of phosphorylated BAD (Zha et al., 1996), the phosphorylation of the shorter murine BAD resulted in a shift of a lower molecular weight band, representing unphosphorylated shorter murine BAD, to a higher molecular weight band, representing phosphorylated shorter murine BAD. Of note, each of the BAD mutants resolved as a doublet on a 16% SDS-PAGE, even though in the amino acid sequence of each of the BAD mutants one or both of the serines corresponding to Ser112 and Ser136 were mutated, i.e., substituted with alanine. The higher molecular weight band of the doublet comigrated on the SDS-PAGE with the band representing phosphorylated shorter murine BAD, and the lower molecular weight band of the doublet comigrated on the SDS-PAGE with the band representing unphosphorylated shorter murine BAD (results not shown). To verify that the higher molecular band in the doublet was a result of phosphorylation, COS-7 cells transfected with the HA-BAD S112A/S136A double mutant were lysed and treated with lambda phosphatase or a buffer control. The proteins were separated via SDS-PAGE, transfer to nitrocellulose and probed with an anti-HA antibody. The results demonstrated that the phosphatase treatment completely eliminated the higher molecular weight band of the doublet, suggesting the existence of a phosphorylation site on BAD that is distinct from either of the serines at positions corresponding to Ser112 and Ser136 (FIG. 1, compare lanes 1 and 2).

In order to test whether the additional and novel phosphorylation site on BAD has functional significance, the effect on BAD binding to Bcl-X$_L$ was examined. Recombinant Bcl-X$_L$ tagged with the glutathione S-transferase ("GST") moiety ("GST-Bcl-X$_L$") was incubated with WCL prepared from COS-7 cells expressing the double mutant HA-BAD S112A/S136A, and the HA-BAD S112A/S136A that bound to the GST-Bcl-X$_L$ was precipitated with GST beads. In a western blot of the WCL incubated with GST-Bcl-X$_L$ and probed with anti-HA antibody, only the lower molecular weight band of the doublet was detected in the WCL where HA-BAD S112A/S136A was bound to the GST-Bcl-X$_L$ and precipitated with GST beads (FIG. 1, lane 3), suggesting that the phosphorylation of BAD at the additional and novel phosphorylation site prevents BAD heterodimer formation with Bcl-X$_L$. No HA-BAD S112A/S136A was precipitated with GST beads from the WCL that were not incubated with GST-Bcl-X$_L$ (FIG. 1, lane 4).

Example 2

Localization and Identification of the Novel BAD Phosphorylation Site, Ser155

In order to localize the novel phosphorylation site, selected serine residues in the amino acid sequence of the shorter murine BAD of SEQ ID NO:3 were substituted with alanines, in addition to the serines at positions corresponding to Ser112 and Ser136. Two HA-BAD triple mutants were constructed. The triple mutant HA-BAD S112A/S134A/S136A has an amino acid sequence, wherein the serines at positions corresponding to Ser112 and Ser136, and the serine at position 134 ("Ser134"), of SEQ ID NO:2, are substituted with alanine. The triple mutant HA-BAD S112A/S136A/S155A has an amino acid sequence, wherein the serines at positions corresponding to Ser112 and Ser136, as well as the serine at position 155 ("Ser155") of SEQ ID NO:2, are substituted with alanine. The correct DNA sequence encoding BAD or a mutant BAD was confirmed by DNA sequencing. The DNA encoding BAD or a mutant BAD was then inserted into the vector pcDNA3, between the BamHI and EcoRI restriction enzyme sites, so that the encoded amino acid sequence of the BAD or mutant BAD was in-frame with and operably linked to an HA epitope at the amino terminus of the encoded BAD or mutant BAD. The DNA was then used to transform COS-7 cells.

Figure 2A:
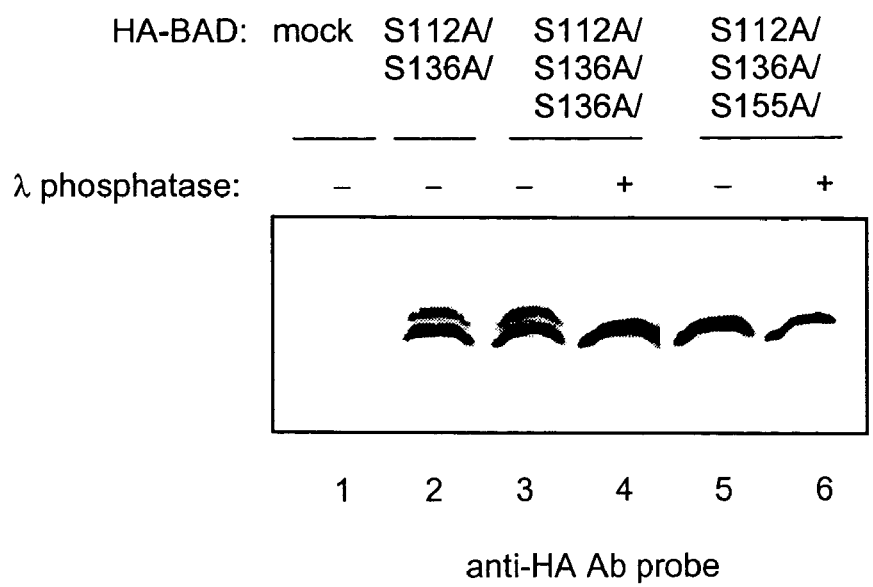
FIG. 2(A) is a western blot. Whole cell lysates were prepared from COS-7 cells transiently expressing empty pcDNA3 vector ("mock") (lane 1), the double mutant HA-BAD S112A/S136A (lane 2), the triple mutant HA-BAD S112A/S134A/S136A (lanes 3 and 4), or the triple mutant HA-BAD S112A/S136A/S155A (lanes 5 and 6). Lysates were treated ("+") with lambda phosphatase or a buffer control ("−") and precipitated with an anti-HA antibody. Proteins were separated by SDS-PAGE. Blots were probed with an anti-HA antibody.

COS-7 cells were transfected with the expression vector encoding the BAD or a mutant BAD. A western blot was performed on WCL prepared from the transfected COS-7 cells expressing HA-BAD S112A/S136A, HA-BAD S112A/S134A/S136A, or HA-BAD S112A/S136A/S155A and treated with phosphatase or a buffer control. The western blot was probed with anti-HA antibody. The results of the western blot demonstrated that mutation of the serine at a position in the amino acid sequence of the shorter murine BAD (SEQ ID NO:3) corresponding to Ser155, eliminates the phosphorylation of BAD (FIG. 2(a), lanes 5 and 6). However, mutation of the serine at a position in the amino acid sequence of the shorter murine BAD (SEQ ID NO:3) corresponding to Ser134 does not eliminate the phosphorylation of BAD (FIG. 2(a), lanes 3 and 4). Moreover, this experiment confirmed that mutation of the serines at positions in the amino acid sequence of the shorter murine BAD (SEQ ID NO:3) corresponding to Ser112 and Ser136 do not eliminate the phosphorylation of BAD (FIG. 2(a), lane 2). These results indicate that the serine corresponding to Ser155 is a third and novel BAD phosphorylation site.

Figure 2B:
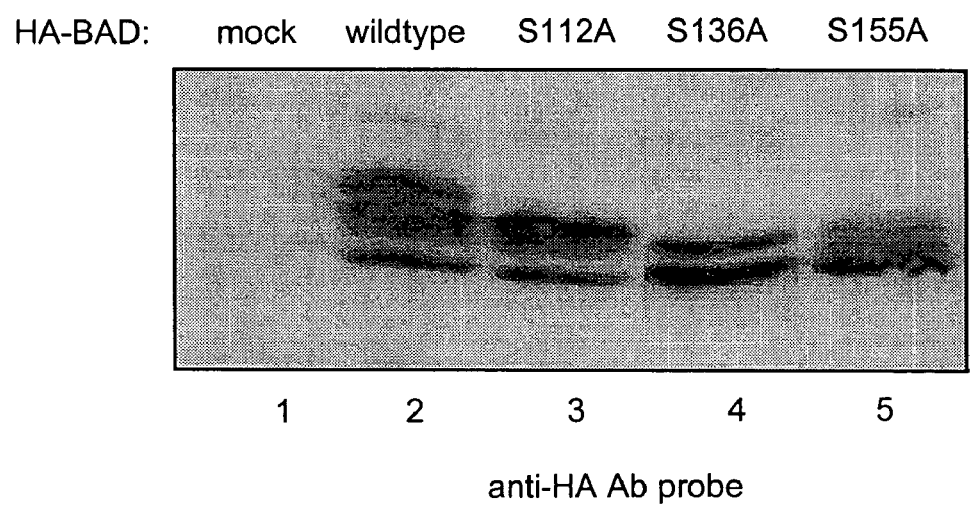
FIG. 2(B) is a western blot. Whole cell lysates were prepared from HeLa cells transiently expressing empty pcDNA3 vector ("mock") (lane 1), shorter murine HA-BAD (SEQ ID NO:3) ("wildtype") (lane 2), HA-BAD S112A (lane 3), HA-BAD S136A (lane 4), or HA-BAD S155A (lane 5). Proteins were separated by SDS-PAGE. Blots were probed with an anti-HA antibody.

A mammalian expression vector encoding mutant HA-BAD S155A, derived from the shorter murine BAD of SEQ ID NO:3, was constructed. HA-BAD S155A has an amino acid sequence wherein the serine at a position corresponding to Ser155 is substituted with alanine. A western blot was performed on WCL prepared from cells expressing the shorter murine BAD (SEQ ID NO:3), HA-BAD S112A, HA-BAD S136A, or HA-BAD S155A, and probed with anti-HA antibody. The results of the western blot analysis demonstrated that a single mutation of the amino acid sequence of the shorter murine BAD (SEQ ID NO:3), at the serine at a position corresponding to Ser155, dramatically reduced the phosphorylation of the murine BAD in HeLa cells (FIG. 2(b), lane 5), as compared to a single mutation of the serine at a position corresponding to Ser112 or Ser136 (FIG. 2(b), lanes 3 and 4, respectively). These results indicate that phosphorylation of the serine at a position corresponding to Ser155 contributed significantly to the overall phosphorylation of BAD.

Figure 2C:
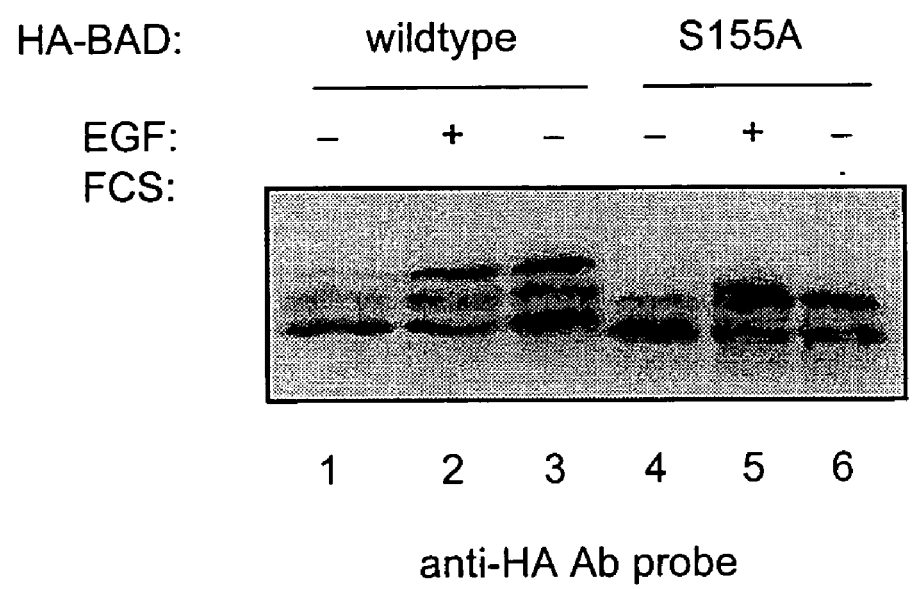
FIG. 2(C) is a western blot. Whole cell lysates were prepared from serum-starved HeLa cells expressing HA-BAD ("wildtype") or HA-BAD S155A, pretreated with epidermal growth factor ("EGF"), fetal calf serum ("FCS") or buffer control. Proteins were separated by SDS-PAGE. Blots were probed with an anti-HA antibody.

A further experiment demonstrated that growth factor-induced phosphorylation of BAD was also eliminated in the S155A mutant. HeLa cells transiently expressing HA-BAD or mutant HA-BAD S155A were cultured in the presence of epidermal growth factor (EGF), fetal calf serum (FCS), or a buffer control. A western blot was performed on whole cell lysates prepared from the cultures, and probed with anti-HA antibody. The results of the western blot analysis demonstrated that a single mutation of the amino acid sequence of the shorter murine BAD (SEQ ID NO:3), at the serine at a position corresponding to Ser155, dramatically reduced the growth factor-induced phosphorylation of the murine BAD in HeLa cells (FIG. 2(c), compare lanes 2 and 5), as well as the serum-induced phosphorylation of the murine BAD in HeLa cells (FIG. 2(c), compare lanes 3 and 6). These results further indicate that phosphorylation of the serine at a position corresponding to Ser155 contributed significantly to the overall phosphorylation of BAD.

Figure 3A:
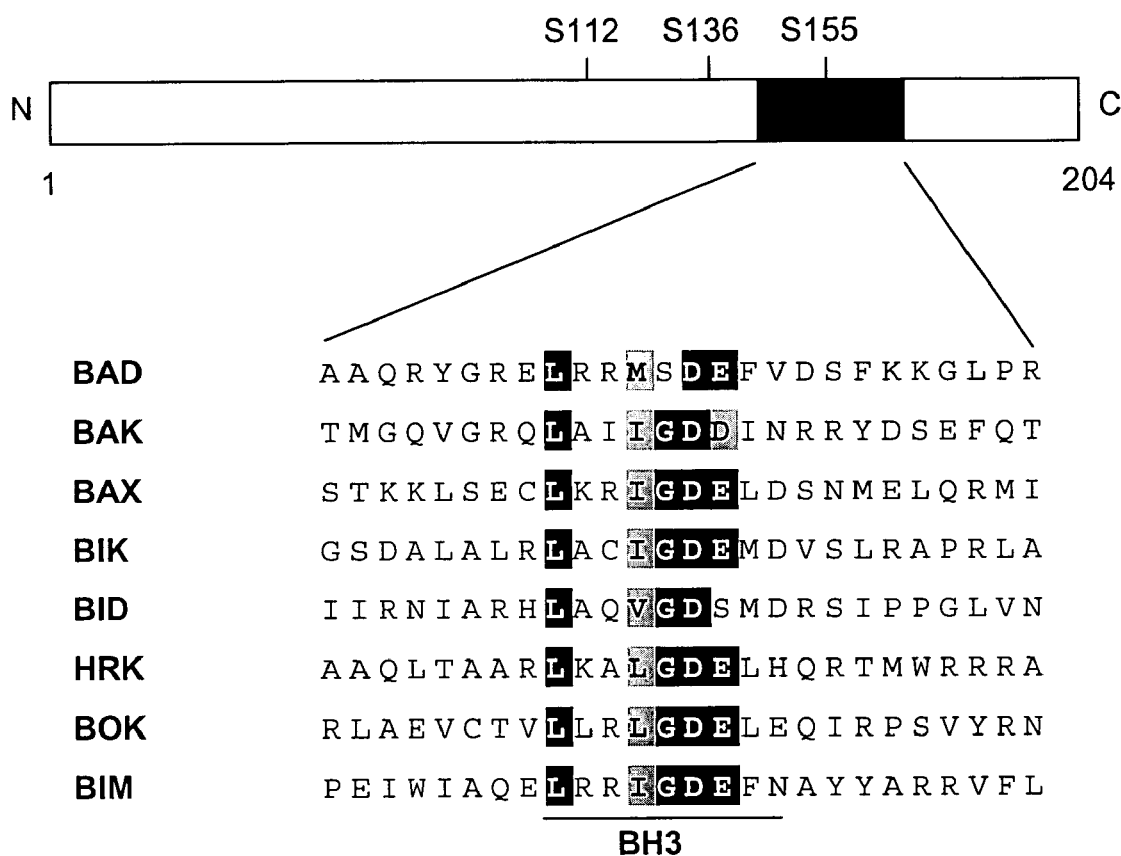
FIG. 3(A) is an amino acid sequence alignment of BH3 domains of the Bcl-family members, against the BH3 domain of human BAD (SEQ ID NO:4). The open rectangle, encompassing the closed rectangle, represents the amino acid sequence of the longer murine BAD (SEQ ID NO:2) protein. The closed rectangle represents the BH3 domain of the longer murine BAD (SEQ ID NO:2) protein. "S112," S136" and "S155" indicate the location of serine residues at positions 112, 136 and 155 of the longer murine BAD (SEQ ID NO:2) protein, respectively. The amino acid sequences are those of BAD (SEQ ID NO:4), BAK (SEQ ID NO:5), BAX (SEQ ID NO:6), BIK (SEQ ID NO:7), BID (SEQ ID NO:8), HRK (SEQ ID NO:9), BOK (SEQ ID NO:10), and BIM (SEQ ID NO:11). Residues surrounded by a black box are identical. Residues surrounded by a gray box are homologous among BH3 domains. The code for the individual residues is A=alamine, C=cysteine, D=aspartic acid, E=glutamic acid, F=phenylalanine, G

Notably, Ser155 is located at the center of the BH3 domain of the longer murine BAD (SEQ ID NO:2) (FIG. 3(a)), i.e., the domain that is involved in the association of BAD with Bcl-$X_L$ (Ottilie et al., 1997; Zha et al., 1997). In contrast to BAD, other members of the Bcl-2 family have a glycine at a position corresponding to Ser155. Ser155 is also within a PKA consensus site.

Figure 3B:
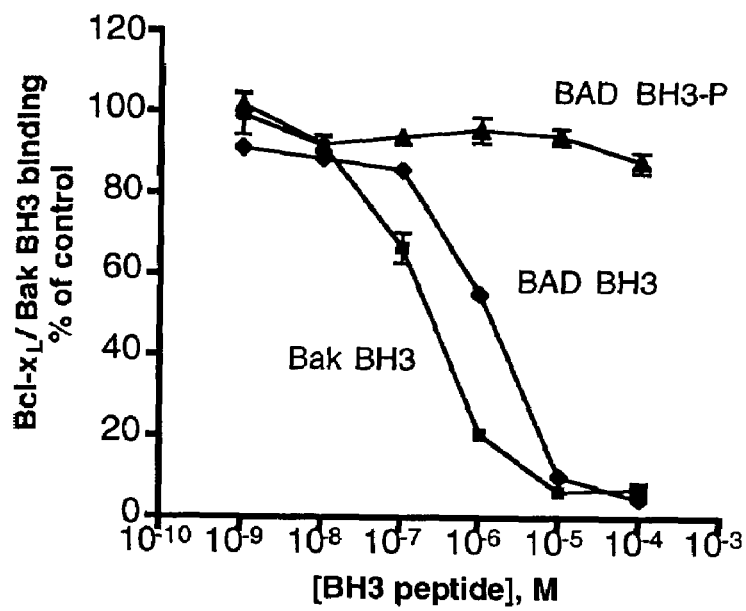
FIG. 3(B) is a graphical representation of the results of an in vitro competition binding assay. Recombinant GST-Bcl-$X_L$ was incubated with a BAD BH3 peptide (residues 143–168 of SEQ ID NO: 2) phosphorylated on Ser155 ("BAD BH3-P"), a BAD BH3 peptide (residues 143–168 of SEQ ID NO: 2) unphosphorylated on Ser155 ("BAD BH3"), or a BAK BH3 peptide (residues 71–89; residues 1–20 of SEQ ID NO: 5) as a positive control, at the indicated concentrations. The reaction mixtures were then added to microtiter plates pre-coated with BAK BH3 peptide. The amount of bound GST-Bcl-$X_L$ was determined by ELISA using an anti-GST primary antibody and a horse-radish peroxidase-conjugated anti-mouse IgG secondary antibody with ABTS as substrate.

NMR studies have revealed that BH3 forms an alpha helical structure, which binds to a hydrophobic cleft on the surface of Bcl-$X_L$ (Sattler et al., 1997). Whether the addition of a phosphate group on BAD Ser155 interferes with this interaction was tested by measuring the affinity of BAD BH3 peptides for Bcl-$X_L$ in an in vitro competition binding assay. Synthetic BAD BH3 peptide encompassing BAD residues 143 to 168, was incubated with recombinant GST-Bcl-$X_L$ at the indicated concentrations (FIG. 3(b)). The affinity of the BAD BH3 peptide for GST-Bcl-$X_L$ was measured as the ability of the peptide to block subsequent binding of GST-Bcl-$X_L$ to a BAK BH3 peptide when the reacted mixture was added to a microtiter plate pre-immobilized with a BAK BH3 peptide, as detected by ELISA (triplicate samples, +/−standard deviation). Both phosphorylated (BAD BH3-P) and unphosphorylated (BAD BH3) BAD were assayed, as was a BAK BH3 peptide (residues 71–89) as a positive control. The unphosphorylated BAD BH3 peptide bound to Bcl-$X_L$ with an affinity similar to the BAK BH3 control peptide, however, the affinity of BAD phosphorylated on Ser155 for Bcl-$X_L$ was reduced by greater than 100-fold (FIG. 3(b)).

Figure 3C:
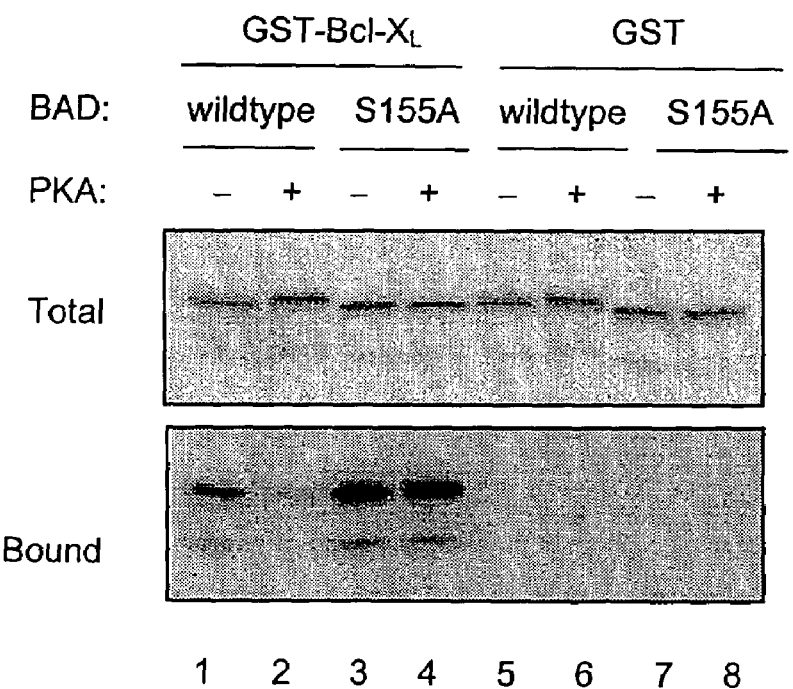
FIG. 3(C) is two autoradiographs. Full-length BAD ("wildtype") and mutant BAD S155A ("S155A") were produced by in vitro translation and labeled with $^{35}$S-methionine therein. The labeled proteins were incubated with PKA ("+") or a buffer control ("−"), and then incubated with either GST or GST-Bcl-$X_L$, followed by capture on glutathione-agarose beads. Proteins bound to the beads ("Bound") (lower panel) and samples of the reactions collected prior to incubation with the beads ("Total") (upper panel) were analyzed by SDS-PAGE followed by autoradiography.

The ability of full-length BAD and mutant BAD S155A to bind Bcl-$X_L$ was also determined (FIG. 3(c)). Full-length BAD ("WT") and mutant BAD S155A ("S155A") were produced by in vitro translation and labeled with $^{35}$S-methionine therein. The labeled proteins were then incubated with PKA ("+") in the presence of unlabeled ATP or a buffer control ("−"). Following the kinase reactions, aliquots of each sample of the four samples were incubated with either GST or GST-Bcl-$X_L$. The protein complex were captured on glutathione-agarose beads. Proteins bound to the beads ("Bound") (lower panel) and samples of the reactions collected prior to incubation with the beads ("Total") (upper panel) were analyzed by SDS-PAGE followed by autoradiography. The results demonstrate that phosphorylation by PKA induced a gel-mobility shift of wild-type BAD (FIG. 3(c), compare lanes 1 and 2, and also lanes 5 and 6, upper panel), but not mutant S155A BAD (FIG. 3(c), compare lanes 3 and 4, and also lanes 7 and 8, upper panel), and blocked the ability of BAD to bind to Bcl-$X_L$ (FIG. 3(c), lower panel). These results demonstrate that phosphorylation on Ser155 is sufficient to directly inactivate the heterodimerization function of BH3 and provide a biochemical mechanism for how the pro-apoptotic function of BAD is suppressed by Ser155 phosphorylation.

Example 3

Ser155 of BAD is Phosphorylated by PKA In Vitro

The amino acid sequence surrounding Ser155 of the longer murine BAD (SEQ ID NO:2) was examined for the presence of serine-threonine kinase recognition motifs. The amino acid sequence LRRMSD (SEQ ID NO: 19) matched well with the consensus recognition sequence of mammalian PKA, which is XRRXSX (Kemp and Pearson, 1990). Based on this finding, PKA was tested to determine whether it could phosphorylate BAD, in vitro, at the serine at a position corresponding to Ser155.

Expression vectors encoding fusion polypeptides of the shorter murine BAD (SEQ ID NO:3) and BAD mutants derived from the shorter murine BAD, were constructed such that the encoded amino acid sequence of the BAD or mutant BAD was fused in-frame and operably linked to the GST moiety. The amino acid sequence of GST-BAD encodes a GST-tagged shorter murine BAD. The amino acid sequence of GST-BAD S112A encodes a GST-tagged mutant BAD, wherein the serine at a position corresponding to Ser112 is substituted with alanine. The amino acid sequence of GST-BAD S136A encodes a GST-tagged mutant BAD, wherein the serine at a position corresponding to Ser136 is substituted with alanine. The amino acid sequence of GST-BAD S155A encodes a GST-tagged mutant BAD, wherein the serine at a position corresponding to Ser155 is substituted with alanine. The amino acid sequence of GST-BAD S112A/S136A encodes a GST-tagged mutant BAD, wherein the serines at positions corresponding to Ser112 and Ser136 are substituted with alanine. The amino acid sequence of GST-BAD S112A/S136A/S155A encodes a GST-tagged mutant BAD, wherein the serines at positions corresponding to position 112, position 136, and position 155 of SEQ ID NO:2 are substituted with alanine.

The GST-tagged BAD and BAD mutants were then expressed individually in cells and the purified GST-tagged polypeptides incubated with purified PKA, in the presence of $^{32}$P radiolabel. A western blot, probed with anti-BAD antibody, was performed on the incubated GST-tagged BAD and BAD mutants to determine whether PKA could phosphorylate the BAD and/or mutant BAD in vitro. The GST-tagged BAD and BAD mutants phosphorylated by PKA could be detected directly by autoradiography due to the incorporation of $^{32}$P radiolabel when the polypeptides were phosphorylated (FIG. 4, upper panel), whereas the total amount of BAD and mutant BAD present in the in vitro reaction was detected by the anti-BAD antibody probe (FIG. 4, lower panel).

Figure 4:
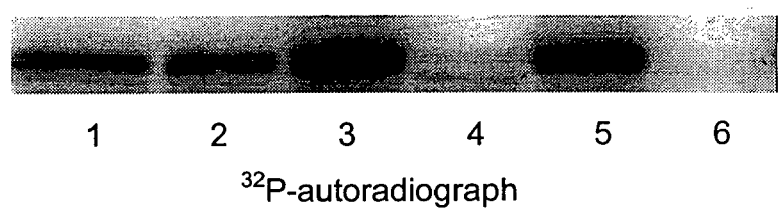
FIG. 4 is a western blot and an autoradiograph. Whole cell lysates were prepared from COS-7 cells expressing GST-tagged shorter murine BAD (SEQ ID NO:3) ("wildtype") (lane 1), GST-BAD S112A ("S112A") (lane 2), GST-BAD S136A ("S136A") (lane 3), GST-BAD S155A ("S155A") (lane 4), GST-BAD S112A/S136A ("S112A/S136A") (lane 5), and GST-BAD S112A/S136A/S155A ("S112A/S136A/S155A") (lane 6). Lysates were precipitated with glutathione beads, and the purified GST-tagged polypeptides were incubated with PKA in the presence of γ-$^{32}$P-ATP radiolabel. Proteins were separated by SDS-PAGE, and phosphorylation was judged by autoradiograph (upper panel), while equivalent loading was confirmed by probing with an anti-BAD antibody (lower panel) on the same membrane.
Figure 4:
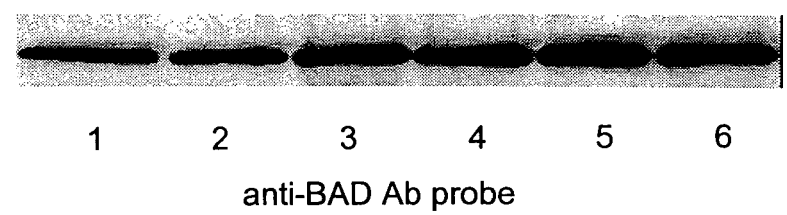

The results of the western blot demonstrate that the shorter murine BAD, and BAD mutants containing mutations at the serine at a position corresponding to Ser112 and/or Ser136, were good in vitro substrates for PKA (FIG. 4, lanes 1–3 and 5). However, in contrast, the BAD mutants containing a mutation at the serine at a position corresponding Ser155 were poor in vitro substrates for PKA. The mutation at the serine at a position corresponding to Ser155 dramatically reduced the phosphorylation of the single mutant GST-BAD S155A and abolished phosphorylation of the triple mutant GST-BAD S112A/S135A/S155A (FIG. 4, lanes 4 and 6, respectively). Thus, the serine at a position in the amino acid sequence of the shorter murine BAD, corresponding to Ser155 is a major site of PKA phosphorylation.

The same western blot was then probed with anti-BAD antibody to confirm that a similar amount of BAD and mutant BAD was added to each kinase reaction (FIG. 4, lower panel).

Moreover, the in vitro phosphorylation of BAD by PKA was completely inhibited by PKI (data not shown), a PKA-specific inhibitor (Chijiwa et al., 1990). These results indicate that Ser155, of the longer murine BAD, is a major phosphorylation site of BAD by PKA in vitro.

Example 4

Forskolin Induces Phosphorylation of BAD Ser155

The fact that PKA preferentially phosphorylated BAD at the serine at a position corresponding to Ser155 in vitro suggested that PKA may be the cellular kinase responsible for the phosphorylation of BAD at this phosphorylation site as well. To test this possibility, HA-BAD and mutants HA-BAD S112A/S136A and HA-BAD S112A/S136A/S155A were transiently expressed in HeLa cells, and samples of the transfected cells were treated with Forskolin, an activator of adenylate cyclase (and, ultimately, PKA) (Fischer et al., 1981).

A western blot analysis, probed with anti-HA antibody, was performed on lysates produced from the Forskolin treated and untreated (control) cells to determine whether Forskolin could induce the phosphorylation BAD or mutant BAD. The results of the western blot demonstrated that treatment with Forskolin induced a significant band-shift of HA-BAD S112A/S136A (FIG. 5(a), lanes 2 and 3) that was rapid and sustained (FIG. 5(b)). Because Forskolin is a known activator of the pathway leading to PKA activation, these results indicate that cellular PKA is responsible for phosphorylation of Ser155 of BAD. Consistent with this observation, treatment of the cells with the cell permeant cAMP analog, 6-Bnz-cAMP, in place of Forskolin, also led to Ser155 phosphorylation of BAD (see FIG. 9(a)).

Figure 5A:
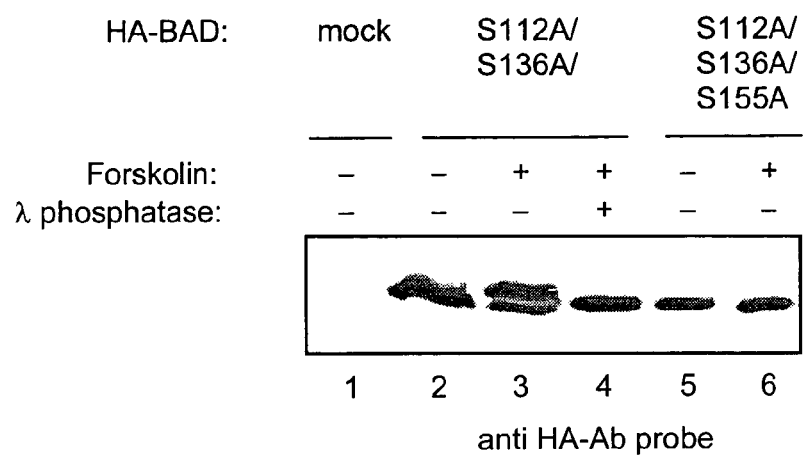
FIG. 5(A) is a western blot. Whole cell lysates were prepared from HeLa cells transiently expressing empty expression vector ("mock") (lane 1), HA-BAD S112A/S136A (lanes 2, 3 and 4), and HA-BAD S112A/S136A/S155A (lanes 5 and 6), pretreated with Forskolin ("+") or a buffer control ("−") and then lambda phosphatase ("+") or a buffer control ("−") prior to lysis. Proteins were separated by SDS-PAGE. Blots were probed with an anti-HA antibody.
Figure 5B:
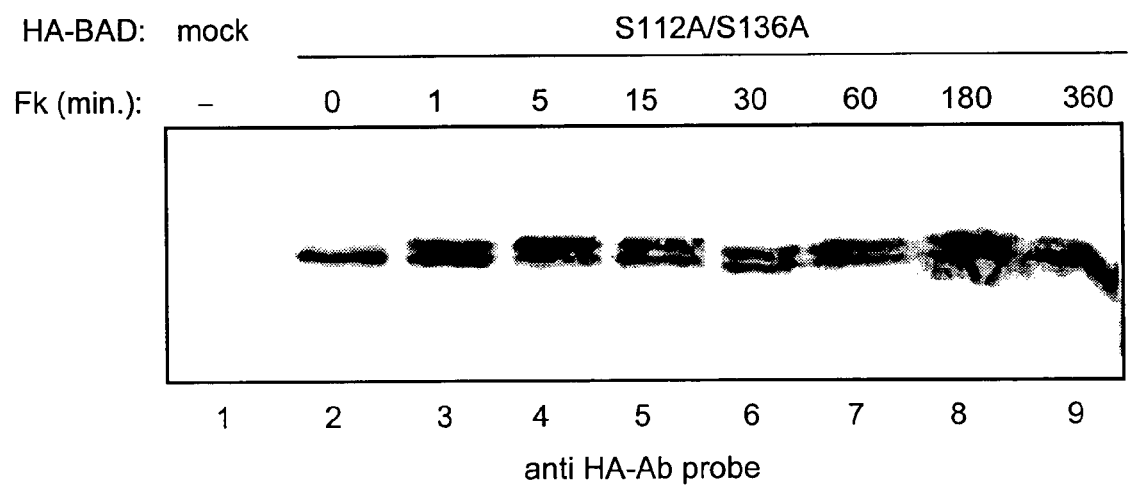
FIG. 5(B) is a western blot. Whole cell lysates were prepared from HeLa cells transiently expressing empty expression vector ("mock") (lane 1), or HA-BAD S112A/S136A (lanes 2–9), treated with Forskolin ("Fk") for the indicated time periods prior to lysis. Proteins were separated by SDS-PAGE. Blots were probed with an anti-HA antibody.

In contrast, the BAD triple mutant HA-BAD S112A/S136A/S155A failed to show such a band-shift, again indicating that Ser155 is the likely site of PKA phosphorylation of BAD in cells (FIG. 5(a), lanes 5 and 6).

Figure 5C:
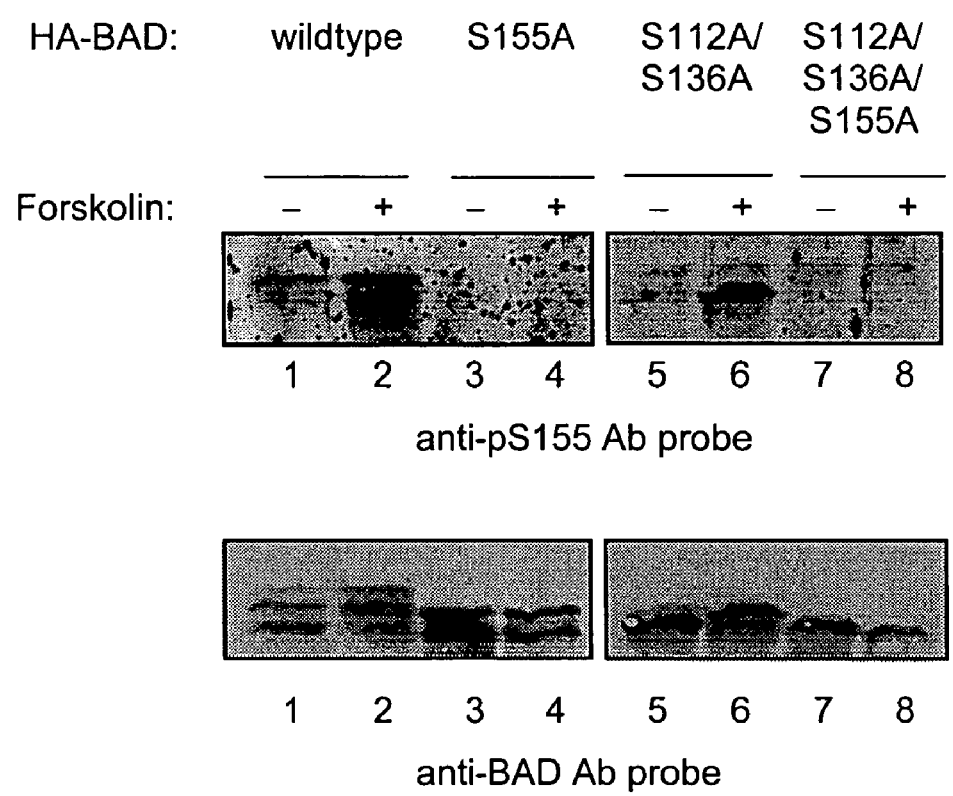
FIG. 5(C) is a series of western blots. Whole cell lysates were prepared from HeLa cells transiently expressing HA-BAD ("wildtype") (lanes 1 and 2), HA-BAD S155A ("S155A") (lanes 3 and 4), HA-BAD S112A/S136A ("S112A/S136A") (lanes 5 and 6), or HA-BAD S112A/S136A/S155A ("S112A/S136A/S155A") (lanes 7 and 8), pretreated with Forskolin ("+") or a buffer control ("−") prior to lysis. Proteins were separated by SDS-PAGE. Blots were probed with anti-phospho-Ser155 specific BAD antibody ("anti-pS155 Ab probe") (upper panels), followed by stripping and reprobing with an anti-BAD antibody ("anti-BAD Ab probe") (lower panels).

An anti-phospho-Ser155 specific BAD antibody (see Materials and Methods) was used to provide direct evidence for BAD phosphorylation on Ser155. HeLa cells transiently expressing HA-BAD, HA-BAD S155A, HA-BAD S112A/S136A, or HA-BAD S112A/S136A/S155A were treated with Forskolin or a buffer control. A western blot analysis was performed on lysates prepared from these cells and probed with either anti-phospho-Ser155 specific BAD antibody (FIG. 5(c), upper panels) or an anti-BAD antibody (FIG. 5(c), lower panels). The failure of the anti-phospho-Ser155 specific BAD antibody to react with BAD S155A and the BAD triple mutant, although the expression of BAD and BAD mutants were at similar levels (FIG. 5c, lower panels), provides direct evidence for BAD phosphorylation on Ser155.

Example 5

G-Protein Coupled Receptor Ligand Induces Phosphorylation of BAD Ser155

Additional experiments were conducted to further identify extracellular signaling molecules that promote BAD phosphorylation on Ser155. Because adenylate cyclase is known to be a target of G protein-coupled receptors (GPCRs) (Linder and Gilman, 1992), which in turn catalyzes the formation of cAMP and eventual activation of PKA, three GPCR ligands were tested for their effect on BAD Ser155 phosphorylation: thyroid stimulating hormone (TSH), L-epinephrine (L-epi), and adrenocorticotropic hormone (ACTH).

Figure 6A:
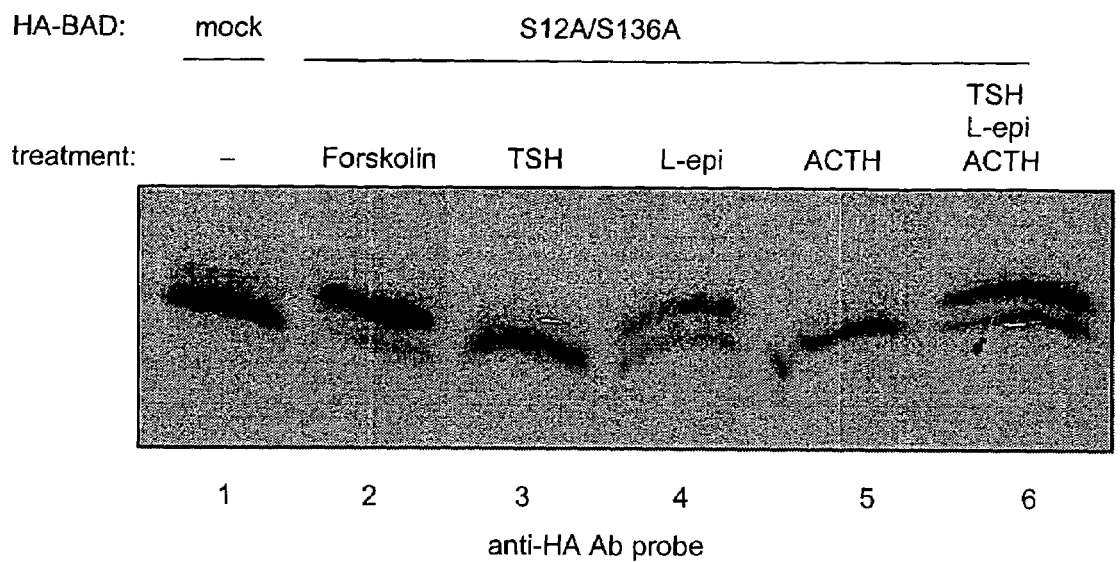
FIG. 6(A) is a western blot. Whole cell lysates were prepared from HeLa cells transiently expressing empty expression vector ("−") (lane 1), or HA-BAD S112A/S136A (lanes 2–6), pretreated with Forskolin (lane 2), thyroid stimulating hormone ("TSH") (lane 3), L-epinephrine ("L-epi") (lane 4), adrenocorticotropic hormone ("ACTH") (lane 5), or a combination of thyroid stimulating hormone, L-epinephrine and adrenocorticotropic hormone ("TSH L-epi ACTH") (lane 6) prior to lysis. Proteins were separated by SDS-PAGE. Blots were probed with an anti-HA antibody.
Figure 6B:
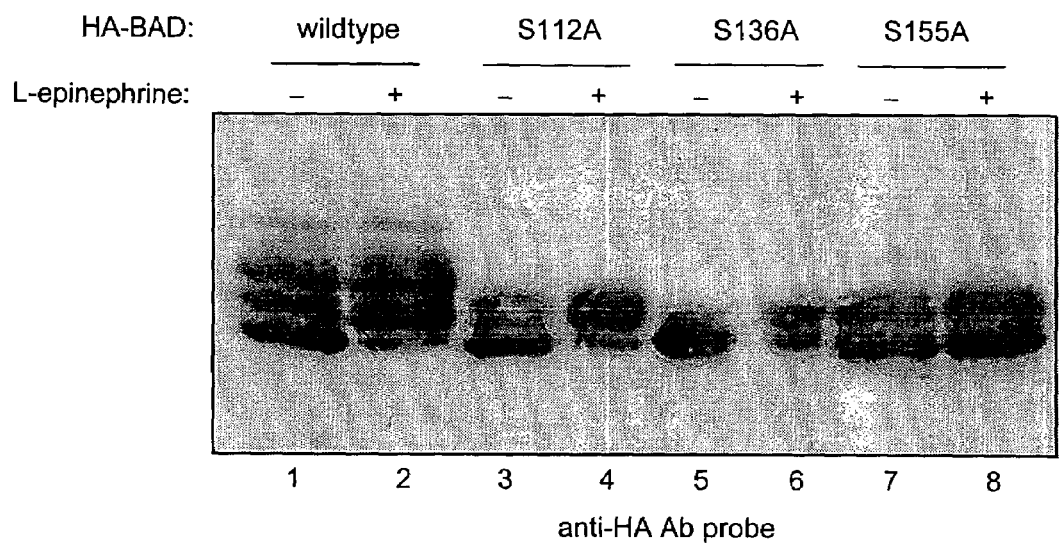
FIG. 6(B) is a western blot. Whole cell lysates were prepared from HeLa cells transiently expressing HA-BAD ("wildtype") (lanes 1 and 2), HA-BAD S112A ("S112A") (lanes 3 and 4), HA-BAD S136A ("S136A") (lanes 5 and 6) and HA-BAD S155A ("S155A") (lane 7 and 8), pretreated with L-epinephrine ("+") or a buffer control ("−") prior to lysis. Proteins were separated by SDS-PAGE. Blots were probed with an anti-HA antibody.

The HA-BAD S112A/S136A double mutant was transiently expressed in HeLa cells, and transfected cell cultures were treated with each of the GPCR ligands, individually and as a group. A western blot analysis, probed with anti-HA antibody, was performed on lysates produced from the treated and untreated (negative control) cells. The results of the western blot demonstrated that treatment with L-epinephrine, either alone, or in combination with TK and ACTH, induced a significant band-shift of HA-BAD S112A/S136A (FIG. 6(a) lanes 4 and 6). In contrast, neither TK (FIG. 6(a), lane 3) nor ACTH (FIG. 6(b), lane 5) alone induces a similar band-shift of the BAD double mutant, an indication that the activation of adenylate cyclase by GPCR is specific to particular GPCR ligands (FIG. 5(a) lanes 5 and 6). Forskolin (FK) and no treatment (−) were positive and negative controls, respectively (FIG. 6(a), lanes and 1, respectively). These results indicate that L-epinephrine is an effective inducer of BAD phosphorylation.

To determine whether the effects of L-epinephrine were due to non-specific phosphorylation of the BAD double mutant, four HA-BAD constructs (HA-BAD, HA-BAD S112A, HA-BAD S136A, and HA-BAD S155A) were transiently expressed in HeLa cells, and samples of the transfected cells were treated with L-epinephrine. Untreated controls received no L-epinephrine. A western blot analysis, probed with anti-HA antibody, was performed on lysates produced from the treated and untreated (control) cells. The results of the western blot demonstrated that while HA-BAD, HA-BAD S112A, and HA-BAD S136A all showed a significant band-shift in response to L-epinephrine stimulation, the S155A single mutant only had a limited response (FIG. 6(b)), suggesting that Ser155, and not Ser112 or Ser136, is the major phosphorylation site in cells in response to L-epinephrine. This result was consistent with the in vitro phosphorylation of BAD at Ser155 by PKA and with the induction of Ser155 phosphorylation by Forskolin, which together suggest the cellular BAD Ser155 kinase is a cAMP-dependent protein kinase that may be activated by G protein-coupled receptors. For HeLa cells as a particular example, the Ser155 kinase could be activated, sequentially, by the L-epinephrine receptor, i.e. the β-adrenergic receptor (Linder and Gilman, 1992), stimulatory G proteins, adenylate cyclase and elevated intracellular cAMP.

Example 6

Forskolin and L-Epinephrine Induces Phosphorylation of Endogenous BAD

Figure 7A:
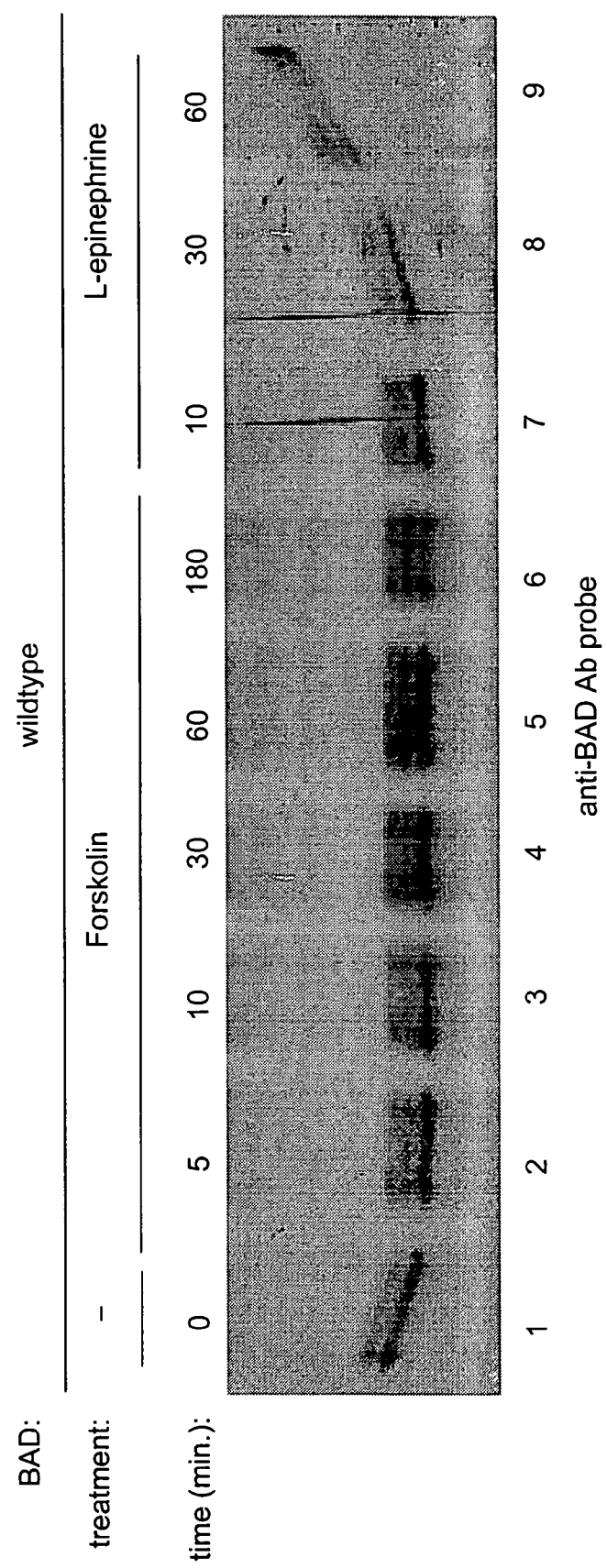
FIG. 7(A) is a western blot. Whole cell lysates were prepared from HeLa cells expressing endogenous wild-type BAD, and untreated (lane 1), pretreated with Forskolin (lanes 2–6) or L-epinephrine (lanes 7–9) for different lengths of time prior to lysis. Proteins were separated by SDS-PAGE. Blots were probed with an anti-BAD antibody.

To rule out the possibility that the evidence for Forskolin- or L-epinephrine-induced BAD Ser155 phosphorylation was an artifact of BAD overexpression, the effects of these agents on endogenous BAD were examined. Non-transfected HeLa cells were treated with Forskolin or L-epinephrine, followed by western blot analysis of cell lysates using anti-BAD antibodies. In untreated HeLa cells, a portion of BAD exhibited retarded migration, suggesting that there was some basal BAD phosphorylation in quiescent cells (FIG. 7(a), lane 1). However, treatment with Forskolin or L-epinephrine resulted in a new band-shift, seen as a third band, as shown in the time course in FIG. 7(a).

Figure 7B:
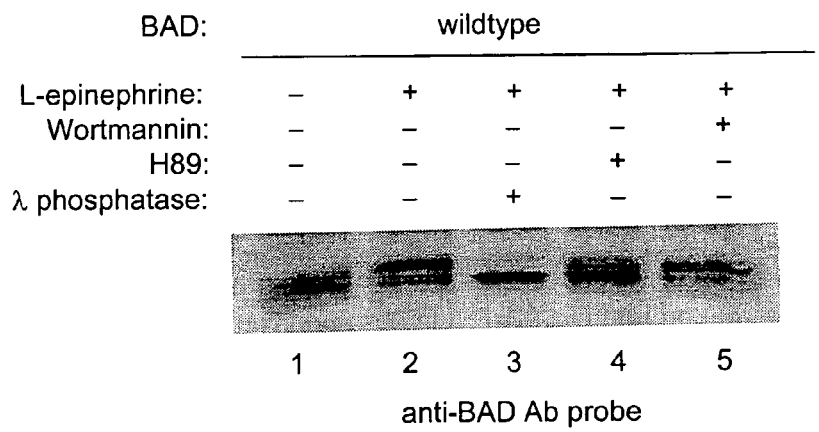
FIG. 7(B) is a western blot. Whole cell lysates were prepared from HeLa cells expressing endogenous wild-type BAD, and untreated (lane 1), pretreated with L-epinephrine alone (lane 2), L-epinephrine and lambda phosphatase (lane 3), L-epinephrine and H89 (lane 4) or L-epinephrine an d Wortmannin (lane 5) prior to lysis. Proteins were separated by SDS-PAGE. Blots were probed with an anti-BAD antibody.

The results shown in FIG. 7(b) demonstrate that the band-shift was sensitive to the PKA inhibitor, H89 (FIG. 7(b), lane 4), but not to Wortmannin, a PI 3-kinase inhibitor (FIG. 7(b) lane 5). Furthermore, both upper bands were sensitive to phosphatase, indicating that they represent phosphorylated BAD (FIG. 7(b), lane 3).

Figure 7C:
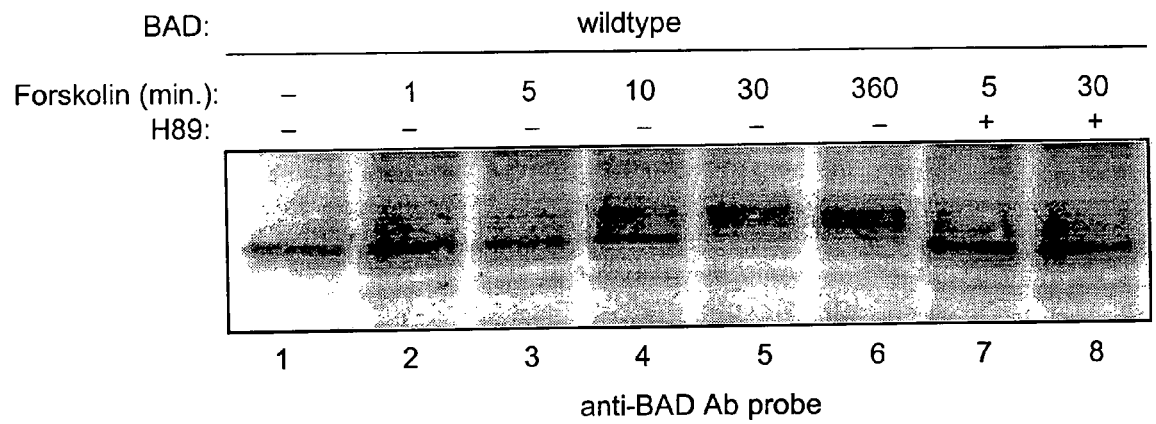
FIG. 7(C) is two western blots. Whole cell lysates were prepared from Rat-1 cells expressing endogenous wild-type BAD, untreated ("−") (lane 1, upper panel), pretreated with Forskolin for various times (lanes 2–6, upper panel) or treated with Forskolin and H89 for 5 minutes (lane 7, upper panel) or 30 minutes (lane 8, upper panel) prior to lysis. Proteins were separated by SDS-PAGE. Blots were probed with an anti-BAD antibody.
Figure 7C:
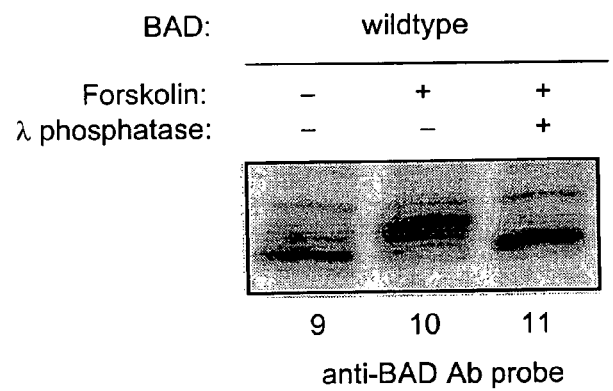

Forskolin treatment also resulted in a BAD band-shift in Rat-1 cells that was sensitive to the PKA inhibitor H89 (FIG. 7(c) lanes 7 and 8), but not to Wortmannin (not shown). The upper band induced by Forskolin was sensitive to phosphate (FIG. 7(c), lane 3, lower panel), again indicating that it represents phosphorylated BAD. In the absence of a phospho-Ser155 antibody, it was difficult to conclude that this band-shift was solely the result of the phosphorylation of Ser155. However, it appeared that this response was at least primarily due to the phosphorylation at this site. This was based on the combined evidence, both in vitro and in cells, as described above (FIGS. 1, 2 and 4–7) and the fact that Ser155 is the only site of BAD homologous to the substrate consensus sequence of PKA. These results also suggest that cAMP-dependent induction of BAD phosphorylation does not require overexpression of BAD in cells, nor does it require mutations of Ser112 or Ser136.

Example 6

PKI Inhibition of L-Epinephrine Induces Phosphorylation of the BAD Double Mutant To further verify that the cAMP-dependent BAD Ser155 kinase is PKA, cDNA encoding PKI, the highly specific endogenous PKA inhibitor (Day et al., 1989), was derived from HeLa cells, and HeLa cells were co-transfected with HA-PKI and HA-BAD S112A/S136A. Transformants were treated with L-epinephrine, then lysed and subjected to anti-HA western blot analysis. Overexpressed PKI blocked L-epinephrine induction of Ser155 phosphorylation (FIG. 8(a)). This result is consistent with the inhibitory effect of H89 (FIG. 8(b)), and together indicate that PKA is a BAD Ser155 kinase that is activated by elevated intracellular cAMP.

Example 7

Growth Factor Induction of BAD Phosphorylation in Fibroblasts

Growth factors also have been shown to confer protection from apoptosis. Whether the BAD Ser155 kinase, PKA, is also activated by growth factors, and if so, whether such activation is PI 3-kinase dependent, was investigated. Rat-1 cells transiently expressing HA-BAD S112A/S136A were treated with platelet-derived growth factor (PDGF), epidermal growth factor (EGF), insulin-like growth factor 1 (IGF-1), N6-Benzoyl-Adenosine 3',5'-cyclic monophosphate (6-Bnz-cAMP) and Forskolin (FIG. 9(a)). Cell lysates were analyzed via western blot analysis, probed using anti-HA antibody. IGF-1, EGF and PDGF induced a band-shift in the BAD double mutant in Rat-1 fibroblasts. However, the magnitude of phosphorylation was weaker and may be more transient, than the effect of Forskolin (FIG. 9(a)). Of note, Ser155 phosphorylation following IGF-1, EGF, or PDGF stimulation was not detected in HeLa cells (results not shown).

It has been documented that Akt kinase activity, the serine kinase shown to phosphorylate BAD Ser136, is induced by growth factors and is dependent on PI 3-kinase activation (Datta et al., 1997; del Peso et al., 1997). In related experiments, Rat-1 cells were pretreated with either the PKA inhibitor H89, or the PI 3-kinase inhibitor Wortmannin (available, e.g., from Sigma, St. Louis, Mo.), followed by stimulation with Forskolin (also available from Sigma) or PDGF. Resulting western blot analyses of cell lysates demonstrated that a PDGF-induced BAD band-shift was significantly reduced by H89 pretreatment. This indicated the shift was PKA dependent (FIG. 9(b), lower panel, compare lanes 5 and 6). However, this PKA inhibitor had no effect on PDGF-induced Akt activation, indicating Akt activation was not PKA dependent (FIG. 9(b), upper panel, compare lanes 5 and 6). It therefore presumably had no effect on PDGF-induced activation of PI 3-kinase. This result suggested that PKA is activated by PDGF in Rat-1 cells, and this activation does not appear to depend on activation of PI 3-kinase and Akt.

In contrast, pretreatment of cells with Wortmannin completely blocked PDGF-induced Akt activation (as expected) (FIG. 9(b), upper panel, compare lanes 5 and 7), yet it only partially inhibited PDGF-induced BAD phosphorylation (FIG. 9(b), lower panel, compare lanes 5 and 7). This suggested that part of the phosphorylation of BAD in response to PDGF is PI 3-kinase and Akt independent.

To examine whether endogenous BAD is phosphorylated on Ser155 in response to growth factors, serum-starved Rat-1 fibroblasts were stimulated with PDGF. Whole cell lysates were prepared and endogenous BAD was immunoprecipitated. Proteins were separated by SDS-PAGE, and Ser155 phosphorylation was analyzed by Western blot using the phospho-S155 antibody and an anti-BAD antibody. As demonstrated in FIG. 9(c), PDGF induced the phosphorylation of endogenous BAD on Ser155 (FIG. 9(c)).

To determine whether growth factor-induced Ser155 phosphorylation of BAD is sensitive to the PKA inhibitor protein PKI, HeLa cells were co-transfected with HA-BAD S112A/S136 and either the PKI expression vector or empty expression vector, and then treated with EGF. Western blots probed with anti-HA antibody demonstrate that while EGF stimulated the phosphorylation of BAD on Ser155, this phosphorylation was blocked by co-expression of PKI (FIG. 10(a)).

To further test whether phosphorylation of Ser155 is dependent on the PI 3-kinase/Akt pathway, HeLa cells were transfected with the mutant HA-BAD S155A and pretreated with Wortmannin, an inhibitor of PI 3-kinase. These cells were then stimulated with epidermal growth factor (EGF), lysed and analyzed by western blot analysis. Wortmannin treatment prevented the activation of endogenous Akt by PI-3 kinase following EGF stimulation (FIG. 10(b), compare lanes 2 and 4, panel B), but did not impair EGF-induced phosphorylation of BAD on Ser155 (FIG. 10(b), compare lanes 2 and 4, panel D). In parallel assays, BAD Ser155 phosphorylation was prevented by the addition of the PKA inhibitor H89 (FIG. 10(b), compare lanes 2 and 5, panel D) without affecting the phosphorylation of Akt (FIG. 10(b), compare lanes 2 and 5, panel B). The EGF receptor (EGFR) kinase inhibitor AG1478 (AG) blocked the phosphorylation of both Akt (FIG. 10(b), compare lanes 2 and 3, panel B) and BAD Ser155 (FIG. 10(b), compare lanes 2 and 3, panel D). These results demonstrate that EGF stimulates the phosphorylation of BAD Ser155 through a PKA-dependent mechanism that is distinct from the PI-3 kinase/Akt pathway.

PDGF-induced Ser155 phosphorylation of endogenous BAD was also significantly reduced by pretreatment of cells with the PKA inhibitor H89, but not the PI 3-kinase inhibitor Wortmannin (FIG. 10(c)).

Taken together, these results suggest that Akt, the Ser136 BAD kinase, and PKA, the putative Ser155 BAD kinase, are both downstream of activated growth factor receptors, and both contribute to the overall phosphorylation of BAD following growth factor stimulation, and the former, but not the latter, is dependent on PI 3-kinase.

Example 8

Mutation of BAD Ser155 to a Non-Phosphorylatable Residue Promotes Cell Death

Because BAD Ser155 phosphorylation, like Ser136 phosphorylation, prevents BAD from binding to Bcl-$X_L$ (FIG. 1), it was possible that by analogy, Ser155 dephosphorylation promotes cell death. To test this idea, HeLa cells were co-transfected with BAD or various BAD serine mutants and a β-gal reporter plasmid. Twenty-four hours post-transfection, cell viability was analyzed by β-gal ELISA.

Of the three single serine mutations, the mutation of Ser155 (BAD S155A) had the greatest effect on cellular survival, with a significant increase in cell death compared to the control (FIG. 11(a)). Mutation of Ser136 (BAD S136A) had the next greatest effect, followed by mutation of Ser112 (BAD S112A). The BAD triple mutant (BAD S112A/S136A/S155A) had a greater effect than the BAD double mutant (BAD S112A/S136A), suggesting that these phosphorylation sites may not be functionally redundant. To ensure that the greater pro-apoptotic activity of the Ser155 mutants was not due to higher expression levels of these mutant BADs, cells transfected in parallel were lysed 24 hours after transfection and BAD expression levels probed on a western blot with anti-HA antibody (FIG. 11(b)). Although the S155A mutations enhanced apoptotic activity of mutants BAD S155A and BAD S112A/S136A/S155A, the expression levels of these mutants were actually lower than their counterparts without the S155A mutation (compare FIG. 11(b), lanes 3 and 4 to lane 5, and lane 6 to lane 7), a result that appeared to be consistent with the apoptosis data.

Example 9

Phosphorylation of BAD Ser155 Promotes Cell Survival

Based on the observation that substitution of BAD Ser155 with a nonphosphorylatable residue enhances the pro-apoptotic activity of BAD, it was thought that induced phosphorylation of Ser155 might promote cell survival.

To test this idea, HeLa cells were again co-transfected with BAD or various BAD serine mutants and a β-gal reporter plasmid. Forskolin was then added to half of the cultures while the other half was left untreated. Beta-gal ELISAs were performed 24 hours post transfection. As shown in FIG. 12(a), Forskolin was able to reduce apoptosis in wild-type BAD and the BAD S112A/S136A double mutant, but not in the BAD S155A mutant or the BAD S112A/S136A/S155A triple mutant transfected cells. Thus, phosphorylation of Ser155 rescues cells from BAD-induced apoptosis, while substitution of Ser155 with a nonphosphorylatable residue results in increased cell death and the failure of cells to be protected from induced PKA activity.

Like BAD phosphorylated on Ser112 or Ser136, Ser155-phosphorylated BAD is deficient in binding to Bcl-$X_L$. When introduced into HeLa cells, the BAD S155A mutant showed enhanced apoptotic activity compared with the wild-type mammalian BAD, suggesting that phosphorylation on Ser155 is anti-apoptotic (FIGS. 11(a) and 12(a)). In addition to and consistent with this result, the BAD S112A/S136A/S155A triple mutant was more toxic to transfected HeLa cells than the S112A/S136A double mutant, suggesting the apoptotic effect of Ser155 dephosphorylation is additive to those of Ser112 and Ser136 (FIG. 11(a)).

EGF stimulation also suppressed the pro-apoptotic function of BAD in transfected HeLa cells. HeLa cells were co-transfected with the β-galactosidase gene and either wild-type BAD, BAD S155A, BAD S112A/S136A or BAD S112A/S136A/S155A. Transfected cells were then cultured in serum-free medium (SFM) or SFM supplemented with EGF for 12 hours. Cell lysates were prepared and BAD-induced cell death was measured by the loss of β-galactosidase activity in a fluorescence-based assay. The results demonstrate that mutation of Ser155 to alanine alone does not eliminate the protective effect of EGF, consistent with the ability of EGF to inactivate BAD through the phosphorylation of Ser112 and/or Ser136 (FIG. 12(b)). However, the pro-apoptotic activity of a BAD S112A/S136A double mutant was also suppressed by EGF stimulation, revealing the ability of EGF to inactivate BAD through a distinct mechanism. This mechanism involves Ser155, since mutation of Ser155 to alanine in the context of S112A/S136A completely inhibited the anti-apoptotic effect of EGF stimulation (S112A/S136A/S155A triple mutant) (FIG. 12b, "AAA"). The β-gal reporter assay was valid as a measurement of apoptosis, since BAD-induced reduction of β-gal activity was reversed by the treatment of cells with z-VAD, a broad-spectrum caspase inhibitor (results not shown). These results indicate that the anti-apoptotic effects of EGF can be mediated through Ser155 phosphorylation, independently of Ser112/Ser136 phosphorylation, and are consistent with the distinct EGF-activated signaling pathways that lead to the phosphorylation of BAD on Ser136 and on Ser155.

To further evaluate the impact of Ser155 phosphorylation on the anti-apoptotic activity of BAD, Ser155 was replaced with aspartic acid (S155D) to mimic the negatively charged phospho-Ser155 residue. HeLa cells were co-transfected with β-gal and either an empty vector, wild-type BAD, the BAD S155A mutant or the BAD S155D mutant. The results of the assay demonstrated that BAD S155D showed no pro-apoptotic activity compared to wild-type BAD (FIG. 12(c)). These results further supported the notion that phosphorylation of Ser155 leads to inactivation of BAD in cells.

In summary, Ser155 is the major site of phosphorylation by PKA in vitro. A single S155A mutation reduced PKA catalyzed $^{32}$P-ATP incorporation by more than 90%, compared to the wild-type mammalian BAD substrate (FIG. 4). Because mutations of Ser112 or Ser136 did not result in reduced phosphorylation, and the BAD S112A/S136A/S155A triple mutant failed to show detectable phosphorylation by PKA (FIG. 4), Ser155 is likely to be the only major in vitro PKA phosphorylation site. The low, but detectable level of BAD S155A mutant phosphorylation, compared with the almost undetectable level of BAD triple mutant phosphorylation suggested that Ser112 and/or Ser136 might be minor in vitro PKA phosphorylation site(s).

Activation of PKA in vitro also resulted in phosphorylation of BAD on Ser155. Treatment of BAD S112A/S136A transfected HeLa cells with the membrane-permeable cAMP analog 6-Bnz-cAMP, a PKA activator, led to marked Ser155 phosphorylation (FIG. 9(a)). Stimulation of the BAD double mutant transfected cells with Forskolin, an adenylate cyclase activator that induces cAMP production, also led to a rapid and sustained phosphorylation of BAD on Ser155 (FIG. 5). Consistent with this result, treatment of cells with L-epinephrine, the ligand for a G protein-coupled receptor (β-adrenergic receptor) that sequentially activates the receptor, stimulatory G proteins and adenylate cyclase (Birnbaumer et al., 1990), activated the BAD Ser155 kinase and resulted in the phosphorylation of this site (FIG. 6). This is thought to be the first connection found between G protein-coupled receptors and the regulation of a Bcl-2 family member.

Similar to the results obtained in vitro, Ser155 appeared to be the only major in vivo phosphorylation site of BAD in response to treatment with Forskolin or L-epinephrine. The S155A single mutation significantly reduced L-epinephrine-induced BAD phosphorylation (measured by phosphatase-sensitive band-shift), whereas mutations on Ser112 or Ser136 did not (FIG. 6(b)). Ser155 phosphorylation was not triggered by transfection, since MCF-7 cells stably expressing BAD S112A/S136A also showed a similar response to Forskolin stimulation (data not shown). The phosphorylation of BAD following elevation of intracellular cAMP was not an artifact of overexpression of the BAD in cells since endogenous BAD responded similarly to such treatment and the phosphorylation was sensitive to the PKA inhibitor H89 (FIG. 7).

Overexpression of PKI, an endogenous PKA inhibitor, completely blocked L-epinephrine-induced Ser155 phosphorylation in transfected HeLa cells (FIG. 8(a)). H89 also had a similar effect (FIG. 8(b)). Together these results indicate that the BAD Ser155 phosphorylation following elevated intracellular cAMP is mediated by PKA. Importantly, treatment of HeLa cells with H89 for one hour, not only blocked L-epinephrine-induced BAD phosphorylation, but also reduced basal phosphorylation of endogenous BAD (FIG. 7(a)). This suggests that PKA is also a BAD kinase in quiescent HeLa cells.

Consistent with the failure of Ser155-phosphorylated BAD to bind to Bcl-$X_L$ (FIG. 1) and the enhanced apoptotic activity of BAD that was mutated at Ser155 (FIG. 11(a)), induced phosphorylation of BAD on Ser155 seemed to promote cell survival (FIG. 12(a)). Approximately 50% more cells survived the transient expression of wild-type mammalian BAD, than the BAD S155A mutant, in the presence of Forskolin after 24 hours. A similar observation was made with the BAD double mutant- and triple mutant-transfected cells: additional mutations on BAD abolished the protective function of Forskolin. In fact, Forskolin also protected control (pcDNA3-GST) transfected cells from the toxicity of lipid-mediated transfection, presumably by phosphorylating Ser155 of endogenous BAD (also see FIG. 7(a)). Using β-gal activity as the measure of cell survival, the effect of endogenous BAD should be minimal in untransfected or BAD mutant-transfected cells; BAD and the reporter β-gal were introduced into cells at a ratio of 5:1, therefore the exogenous BAD or BAD mutants were expected to be dominant over endogenous BAD. The transient expression of BAD-induced apoptosis appeared to depend on activation of caspases, treatment of the transfected cells with a caspase inhibitor z-VAD, efficiently protected the cells (data not shown).

The protection of cells from apoptosis via PI 3-kinase/Akt-mediated BAD phosphorylation has been documented (Datta et al., 1997; del Peso et al., 1997). An additional BAD phosphorylation site, Ser155, that suppresses BAD-induced apoptosis in a PI 3-kinase/Akt-independent manner was demonstrated herein. The PKA inhibitor H89, but not the PI 3-kinase inhibitor Wortmannin, blocked growth factor-induced BAD phosphorylation in HeLa cells (FIG. 10(b)) and in Rat-1 cells (FIG. 10(c)), and Forskolin-induced BAD phosphorylation in Rat-1 cells (FIG. 7(b)). In Rat-1 cells, PDGF appears to activate both PKA- and Akt-mediated phosphorylation of BAD. The PKA inhibitor blocked a part of the growth factor-induced phosphorylation without interrupting the activation of PI 3-kinase and Akt; the PKA activator Forskolin induced BAD phosphorylation without activating Akt; and the PI 3-kinase inhibitor only partially blocked PDGF-induced BAD phosphorylation (FIG. 9(b)). Together, these results suggest that in Rat-1 cells, the BAD kinases Akt and PKA are both activated by PDGF, but are likely to function independently.

Kulik and Weber (1998) suggested an IGF-1-induced, Akt-independent survival signaling pathway was present in Rat-1 cells overexpressing the IGF-1 receptor, although the components of this pathway were not known. Results shown herein now suggest that in fibroblasts, the Akt-independent survival pathway activated by growth factor stimulation includes activated PKA. Exactly how growth factors activate PKA in Rat-1 cells is not clear, although there have been reports showing transactivation of G proteins by growth factors (Malbon and Karoor, 1998) and MAP kinase-dependent activation of PKA by PDGF (Graves et al., 1996).

Mutational studies, as taught herein, have provided strong evidence that BAD promotes apoptosis by dimerizing with Bcl-$X_L$ and related proteins, emphasizing the importance of understanding how phosphorylation regulates this interaction. The findings presented here suggest that phosphorylation on different sites within BAD have mechanistically distinct consequences: Ser155 phosphorylation directly prevents heterodimerization by abolishing the affinity of BAD BH3 for Bcl-$X_L$, whereas phosphorylation on Ser112 or Ser136, located outside the BH3 domain, may inhibit dimerization with Bcl-$X_L$ indirectly. In particular, phosphorylation on Ser112 or Ser136, but not Ser155, generates a consensus binding site for the cytosolic protein, 14-3-3, which may bind and alter the sub-cellular distribution of BAD to prevent interaction with Bcl-$X_L$ at mitochondrial membranes.

The discovery of the novel phosphorylation site, Ser155, of BAD, and the possible cellular regulatory mechanisms that lead to its phosphorylation, indicate that cells have the ability to protect themselves via multiple survival pathways.

Which pathway is used could be dependent on the intrinsic properties of the cells, such as the distribution of cell membrane receptors, as well as the extracellular environment.

MATERIAL AND METHODS

Isolation of BAD cDNA, Plasmid Construction and Mutagenesis

The cDNA encoding the murine BAD of SEQ ID NO:2 ("longer murine BAD") was obtained by the Reverse Transcription Polymerase Chain Reaction ("RT-PCR") of mRNA isolated from $FL_{5.12}$ cells using the primers:

5'-GCCTCCAGGATCCAAGATGGGAACC-3' (SEQ ID NO:12); and

5'-GGAGCGGGTAGAATTCCGGGATG-3' (SEQ ID NO:13).

The open-reading frame of the RT-PCR product was predicted to encode a protein of 204 amino acids (aa) (Yang et al., 1995). The cDNA encoding the longer murine BAD was cloned into the pcDNA3 vector (Invitrogen), expressed in $FL_{5.12}$ cells, and the expressed longer murine BAD detected with an anti-BAD antibody (C-20, Santa Cruz). The expressed longer murine BAD was significantly larger in molecular weight than the endogenous BAD (approximately 30 kD and 23 kD, respectively) (FIG. 13, compare lane 1 against lanes 2 and 3, left panel). It was discovered that there is a methionine residue at position 43 of the amino acid sequence of the longer murine BAD that, when aligned with the amino acid sequence of the human BAD, corresponds to the first residue (a methionine) in the human BAD amino acid sequence of SEQ ID NO:1.

Therefore, a second murine BAD cDNA construct was produced, the murine BAD of SEQ ID NO:3 ("shorter murine BAD"). A PCR primer having a sequence complementary to and upstream of the sequence encoding residue 43 of the murine BAD sequence of SEQ ID NO:2

5'-TGGAGACCAGGATCCCAGAGTAGCT-3' (SEQ ID NO:14) and the same downstream primer as above (i.e., SEQ ID NO:13) were used to generate the cDNA of SEQ ID NO:3, which was then cloned into the pcDNA3 vector. This construct, when expressed in $FL_{5.12}$ cells, co-migrated with the endogenous BAD (FIG. 13, compare lanes 4 and 5, left panel, with lane 1, right panel), suggesting that the shorter murine BAD, which is 162 aa in length, is likely to be the major translation product of BAD in $FL_{5.12}$ cells.

BAD mutants have been produced where one or more serine residues were changed to alanine residues using PCR-mediated mutagenesis (Ge and Rudolph, 1997). Herein, BAD mutants were also produced, where one or more of the serine residues at positions 112, 134, 136, and 155, corresponding to the amino acid positions of the longer murine BAD of SEQ ID NO:2, were changed to alanine or aspartic acid. These positions correspond to serine residues in positions 75, 99, 101 and 118 in SEQ ID NO:1 and positions 70, 94, 96 and 113 in SEQ ID NO: 3. One of ordinary skill in the art would understand how to use PCR-mediated mutagenesis to make such changes. Correct DNA sequences encoding for BAD and its mutants were confirmed by DNA sequencing. Resulting BAD mutant cDNAs were then inserted into the pcDNA3 expression vector. Epitope-tagged BAD and BAD mutants were produced by subcloning each of the cDNAs in-frame into a second pcDNA3 vector, between BamHI and EcoRI sites, that already contained the HA epitope sequence upstream to the insertion site.

The cDNA encoding human protein kinase inhibitor (PKI) was isolated from total mRNA of HeLa cells by RT-PCR. The primers used for the reaction were:

5'-CTATGTGGATCCTTGGTAGCAATG (SEQ ID NO:15); and

5'-CCTCATAGACCTTAAGTAAACAAA (SEQ ID NO:16).

The product of the RT-PCR was then digested with the restriction enzymes BamHI and EcoRI, and the sequence encoding the PKI was inserted into the polylinker region of the pcDNA3 vector, so that the nucleotide sequence encoding PKI was in-frame with and operably linked to an HA epitope at the amino ("N") terminus of the encoded PKI. The correct DNA sequence encoding the HA-tagged PKI was confirmed by DNA sequencing.

Expression and Purification of Glutathione s-Transferase (GST) Fusions of Wild-Type and Mutant BAD DNA encoding BAD and various mutant BAD were excised from pcDNA3 as a BamHI-EcoRI fragment and inserted into BamHI-EcoRI cloning sites of pGEX-2T (Pharmacia), downstream of and in-frame with the GST coding region. GST-BAD constructs were then transfected into $E.\ Coli$ strain DH5α. Cells (500 ml) were grown to an $OD_{595}$ of 0.7–0.9 at 37° C. and induced with 2 mM isopropyl β-D-thiogalactopyranoside (Bachem) at 30° C. overnight. Cells were collected by centrifugation and resuspension in 20 ml of HEPES-buffered saline (HBS) (10 mM HEPES, pH 7.5, 3.4 mM EDTA, 150 mM NaCl) plus 1% (vol/vol) Triton X-100 and 10 mM β-mercaptoethanol (BME). Cells were then lysed by two passages through a Microfluidizer M110S (Microfluidics) and cellular debris was removed by centrifugation for 30 minutes at 20,000×g. A 20% ammonium sulfate precipitation was performed on the cell lysate to remove aggregated polypeptide, and GST-BAD was purified from the supernatant by glutathione agarose chromatography (Smith and Johnson, 1988). The fractions containing GST-BAD were pooled and concentrated using a Centriprep 3 (Amicon), and the polypeptide concentration determined by Bradford assay (Bio-Rad). Polypeptide was stored on ice for immediate use or frozen in liquid nitrogen and stored at −80° C.

Cell Culture and Transfections

The Rat-1, COS-7, HeLa and MCF-7 cell lines were cultured in glutamine-free DMEM supplemented with 10% fetal calf serum (FCS), 1% glutamine and 1% penicillin/ streptomycin (GIBCO). $FL_{5.12}$ cells were cultured in glutamine-free IMEM supplemented with 10% FCS, 10% WEHI-conditioned media (collected from WEHI cell cultures), 1% glutamine and 1% penicillin/streptomycin. Transfections were carried out by using the Superfection Kit from Qiagen or the GenePROTOR transfection reagent from Gene Therapy Systems. MCF-7 cells stably expressing BAD or mutant BAD were isolated by G418 selection at 1 mg/ml; G418-resistant clones were then pooled and used for further assays.

Antibodies, Immunoprecipitation and Western Blotting Analyses

Anti-BAD antibody (C-20) was from Santa Cruz Biotechnology, Inc. and anti-HA antibody (3F10) was from Boehringer Mannheim.

An antibody specific against phospho-Ser155 BAD was generated using an 18 aa phosphopeptide from the BAD BH3 domain region (aa 108–125) by Bio-Synthesis Incorporated (Lewisville, Tex.). The sequence of this region is:

QRYGRELRRMSDESVDSF (SEQ ID NO:17).

A phosphopeptide of the sequence
NH$_2$-(GC)QRYGRELRRMpSDESVDSF-COOH (SEQ ID NO:18)
was synthesized at >70% purity and conjugated to keyhole limpet hemocyanin. This antigen was injected into two rabbits, from which serum was collected. The serum included pre-bleed, 6$^{th}$, 8$^{th}$ and 10$^{th}$ week bleeds. The GC in parenthesis represent the linker amino acids. When used at 1:500 dilution, the 10$^{th}$ week bleed from one of the animals was reactive with Ser155-phosphorylated BAD in western blot analysis. The pre-bleed was not reactive. FIG. 14 shows the results of a western blot probe with the polyclonal antibody. The anti-serum was found to recognize both forms of phosphorylated murine BAD and human BAD, as well as fragments of all three proteins and mutant BAD where the serine residue corresponding to Ser155 was not mutated to alanine. In a separate experiment, HeLa cells transiently expressing HA-BAD S112A/S136A were kept in culture for two days in the absence or presence of Forskolin. Lysates were then prepared. Following SDS-PAGE separation, lysate samples were probed with either the anti-HA antibody or the rabbit anti-serum. Lysates from cells prepared in the presence and absence of Forskolin show a band reactive with anti-HA antibody (M$_r$~30 kD). In contrast, for lysates probed with the rabbit anti-human BAD phospho-Ser155 anti-serum, only the Forskolin (a PKA activator) treated cells reacted to display a band at M$_r$~30 kD, demonstrating that the rabbit anti-human BAD phospho-Ser155 antibody is specific to phosphorylated BAD.

For the generation of cell lysates, cells were washed with ice-cold PBS and lysed in RIPA buffer (50 mM HEPES, pH 7.5, 1% deoxycholate, 1% NP-40, 0.1% SDS, 150 mM NaCl, 1 mM Na$_3$(VO)$_4$, 1 mM NaO$_3$P$_7$, 1 mM PMSF, 10 µg/ml leupeptin and 20 µg/ml aprotinin). Lysates were centrifuged at 16,000×g for 15 min at 4° C. and the cleared supernatant was transferred to new tubes.

For immunoprecipitation of all HA-BAD species, 1 µg of the anti-HA antibody was added to the cell lysates, and incubated at 4° C. for one hour. Protein G agarose (Pierce) was then added (50 µl/fraction of 50% slurry) and followed by a one hour incubation at 4° C. Beads were washed with RIPA buffer, boiled in loading buffer (2% SDS, 10% glycerol, 5% β-ME, 60 mM Tris, pH 6.8, 0.002% Bromophenol Blue) and loaded onto polyacrylamide gels. After electrophoresis, proteins were transferred to nitrocellulose membranes, and blots blocked in western wash buffer (40 mM Tris, pH 8.0, 150 mM NaCl, 0.2% NP-40) with 5% BSA for one hour at room temperature. Blots were incubated with primary antibody diluted in western wash buffer with 3% BSA at room temperature for 1–2 hours, washed with western wash buffer and incubated with secondary HRP-coupled antibody diluted in western wash buffer with 1.5% BSA, and washed extensively. Polypeptides were detected with the ECL chemiluminescence according to the manufacturers instructions (Amersham).

In Vitro Polypeptide Binding, Phosphatase Treatment, and In Vitro Kinase Assays

Phosphoserine BADs can be used in assays to screen for inhibitors or activators of serine-phosphatase agents in which a test agent converts the serine-phosphorylated BAD to the non-phosphorylated BAD death promoter. The polypeptides can also be used to screen for and identify serine phosphatase agents that are capable of participating in the control of apoptosis.

For Bcl-X$_L$ binding studies, GST-Bcl-X$_L$ (1 mg/ml final concentration) was added to cell lysates derived from BAD expressing cells, and incubated with rotation for two hours at 4° C. GST-Bcl-X$_L$ and any associated BAD were then isolated using glutathione beads (Pharmacia) that were added to lysate/GST-Bcl-X$_L$ mixture, and incubated for an hour. The beads were then washed with RIPA buffer, the proteins were separated by SDS-PAGE and associated BAD detected by probing the blot with anti-HA antibody.

For phosphatase treatments, cells were lysed in RIPA buffer without phosphatase inhibitors. Lambda protein phosphatase (New England Biolabs) was added to the lysate at 4 U/ml, supplemented with MnCl$_2$ and phosphatase reaction buffer (50 mM Tris-HCl, pH 7.8, containing 5 mM dithiothreitol). The reaction proceeded for 30 min. at 30° C.

In vitro kinase assays were carried out in 30 µl volumes containing 10 mM HEPES buffer, pH 7.5, 100 mM NaCl, 12 mM MgCl$_2$, 1 mM dithiothreitol, 15 mCi γ$^{32}$P-ATP (6000 Ci/mol, NEN), 11 units PKA (catalytic subunit from bovine heart, Calbiochem), and 1 µg purified GST-BAD. Reactions were incubated for 30 min at 30° C. and terminated by the addition of SDS-PAGE sample buffer. Samples were run on a 4–20% SDS-PAGE gel (Novex), transferred to a nitrocellulose membrane and phosphorylated GST-BAD was visualized by autoradiography. To verify that equal amounts of GST-BAD substrates were used, the nitrocellulose was subjected to western blot analysis with 133 ng/ml anti-BAD antibody (C-20).

Apoptosis Assays

Beta-gal ELISA assays were performed using the β-gal ELISA system from Boehringer Mannheim, according to manufacture's instructions. Cells were transfected with BAD (or BAD mutant) and β-gal in a ratio of 5:1. The transfected cells were trypsinized and distributed into 96-well tissue culture plates. Twenty-four hours after transfection, cell extracts were obtained by lysing the cells in lysis buffer. Cell extracts (200 µl) were then added to anti-β-gal-coated microtiter plates (MTP). The MTPs were foil-covered and incubated for one hour at 37° C. Solutions were then decanted and the MTPs were washed, followed by the addition of 200 µl of anti-β-gal-DIG working solution, and incubation for an additional hour as described above. Solutions were again decanted, the MTPs washed and 200 µl of DIG-POD working solution were added. The MTPs were incubated for another hour at 37° C., the solution decanted, and the wells washed. 200 µl of substrate with enhancer were added to each well and incubated at room temperature until color development. The β-gal activity was measured by the absorbance of the sample at 410 nM. Data were based on triplicate wells with standard deviations calculated.

To measure β-gal activity, HeLa cells were plated in 12-well plates at 5×10$^4$ cells/well one day prior to transfection. Cells were transfected with BAD (or BAD mutants) and β-gal expression plasmids in a ratio of 4:1 (0.6 µg:0.15 µg) using the Superfect transfection reagent (Qiagen). Twenty-four hours after transfection, cells were cultured in serum-free medium (SFM) or in SFM plus EGF, for additional 12 hours. Beta-gal activity was measured in extracts using a fluorogenic substrate (MUG, BIO-RAD FluorAce™ β-gal Reporter Assay, #170–3150). Loss of β-gal activity in these assays reflects apoptosis and elimination of the transfected cells, and the β-gal reductions were reversed by the addition of a broad spectrum caspase inhibitor, z-VAD-fmk.

Competition Binding Assay

Immunlon 2 (Dynatech) microtiter plates were coated with 5 µg/ml neutravidin (50 µl/well; Pierce) in sodium bicarbonate buffer, pH 9.0, overnight at 4° C. All remaining steps were conducted at room temperature. Plates were washed twice with PBS containing 0.1% Tween 20 (wash buffer) and blocked for 1 hour with 0.2 ml/well of 1% normal goat serum in PBS. Following two additional washes, 1.25 µg/ml of a BAK BH3 peptide 19-mer (residues 71–89) biotinylated at the amino terminus was added to the wells in 50 µl of 10 mM HEPES buffer, pH 7.2 containing 150 mM KCl, 5 mM MgCl$_2$, 1 mM EGTA, and 0.2% NP-40 (NP-40 buffer). After 30 min, the wells were washed twice with wash buffer and GST-Bcl-X$_L$ (0.25 µM in 50 µl of NP-40 buffer) was added in the absence or presence of BAD or BAK BH3 peptides. Following a one hour incubation, the plates were washed twice with wash buffer and the amount of bound GST-Bcl-X$_L$ was determined by ELISA using an anti-GST primary antibody and an HRP-conjugated anti-mouse IgG secondary antibody (Jackson) with ABTS (Zymed) as substrate. Five washes were conducted following each one hour antibody incubation. GST-Bcl-X$_L$ fusion protein was produced in *E. coli* by a similar procedure described for the production of GST-BAD (see above).

REFERENCE LIST

Amselem et al. *Chem. Phys Lipids* 64:219–237, 1993.
Bakhshi et al. *Cell* 41:899–906, 1985.
Birnbaumer et al. *Biochimica Et Biophysica Acta* 1031: 163–224, 1990.
Blanar and Rutter. *Science* 256:1014–1018, 1992.
Boyd et al. *Oncogene* 11:1921–1928, 1995.
Boyle et al. *Methods Enzymol.* 201:110–149, 1991.
Brewer. *Meth. Cell. Biol.* 43:233–245, 1994.
Burnham. *Am. J. Hosp. Pharm.* 51:210–218, 1994.
Bylund and Toews. *Am. J. Physiol.* 265:L421–429, 1993.
Caprino and Han. *J. Org. Chem.* 37:3404, 1972.
Chijiwa et al. *J. Biol. Chem.* 265:5267–72, 1990.
Chittenden et al. *EMBO J.* 14:5589–5596, 1995.
Chittenden. *Mammalian Bcl-2 Family Genes*, J. W. Wilson, C. Booth and C. S. Potten, eds. Kluwer Academic Publishers, 1998.
Cleary and Sklar. *Proc. Natl. Acad. Sci. USA* 82:7439–7443, 1985.
Cohen. *Ann. Rev. Biochem.* 58:453–508, 1989.
Datta et al. *Cell* 91:231–41, 1997.
Davis et al. *Enzyme Eng.* 4:169–73, 1978.
Day et al. *J. Biol. Chem.* 264:431–6, 1989.
Dayhoff et al. *Atlas of Protein Sequence and Structure*, Dayhoff, Ed., NBRF, Washington, 5(3):345, 1978.
del Peso et al. *Science* 278:687–689, 1997.
Dower et al. *J. Immunol.* 142:4314–4320, 1989.
Farrow and Brown. *Curr. Opin. Genet. Dev.* 6:45–49, 1996.
Fischer et al. *Acta Biol. Med. Ger.* 40:747–55, 1981.
Friden, et al. *Science* 259:373–377, 1993.
Ge and Rudolph. *BioTechniques* 22:28–30, 1997.
Graves et al. *J. Biol. Chem.* 271:505–11, 1996.
Gulfre and Milstein. *Methods Enzymol.* 73:1–46, 1981.
Harada et al. *Mol. Cell Biol.* 3:413–422, 1999.
Hengartner and Horvitz. *Cell* 76:1107–1114, 1994.
Higgens et al. *Cabios* 8:189–191, 1992.
Kemp and Pearson. *TIBS* 15:342–346, 1990.
Korsmeyer. *Blood* 80:879–886, 1992.
Kulik and Weber. *Mol. Cell. Biol.* 18:6711–8, 1998.
Levitski. *Eur. J. Biochem.* 226:1–13, 1994.
Linder and Gilman. *Scientific American* 56–65, 1992.
Luo et al. *Methods Enzymol.* 201:149–152, 1991.
Malbon and Karoor. *Cell. Sig.* 10:523–7, 1998.
Matthews. *Pharmac. Ther.* 67:323–350, 1995.
Merrifeld. *J. Am. Chem. Soc.* 85:2149, 1963.
Milstein and Kohler. *Nature* 256:495–497, 1975.
Muslin et al. *Cell* 84:889–897, 1996.
Navia and Peattie. *Trends Pharm. Sci.* 14:189–195, 1993.
Nielsen. *Biochem. Biophys.* 1088:425–428, 1991.
Olson et al. *J. Med. Chem.* 36:3039–3049, 1993.
Oltvai et al. *Cell* 74:609–619, 1993.
Oltvai and Korsmeyer. *Cell* 79:189–192, 1994.
Ottili et al. *J. Biol. Chem.* 272:30866–72, 1997.
Raff. *Nature* 356:397–400, 1992.
Reed. *Nature* 387:773–776, 1997.
Rovati. *Pharmacol. Res.* 28:277–299, 1993.
Sambrook et al., *Molecular Cloning: A Laboratory Manual*, Cold Spring Harbor Labortory Press, Second Ed., 1989.
Sattler et al. *Science* 275:983–986, 1997.
Scheid and Duronio. *Proc. Natl. Acad. Sci. USA* 95:7439–44, 1998.
Shenolikar. *Cancer Biol.* 6:219–227, 1995.
Sites and Terr, eds. *Basic and Clinical Immunology*, Appleton & Lange, Norwalk, Conn. 217–262, 1991.
Slack et al. *BioTechniques* 7:1132–1138, 1989.
Smith and Johnson. *Gene* 67:31–40, 1988.
Studier et al. *Methods Enzymol.* 185:60–89, 1990.
Thompson. *Science* 267:1456–1462, 1995.
Tsujimoto et al. *Science* 229:1390–1393, 1985.
Wang and Reed. *Biofactors* 8:13–6, 1998.
Wera and Hemmings. *Biochem. J.* 311:17–29, 1995.
Wyllie. *Int. Rev. Cytol.* 68:251–306, 1980.
Yang et al. *Cell* 80:285–91, 1995.
Yin et al. *Nature* 369:321–323, 1994.
Zha et al. *J. Biol. Chem.* 272:24101–4, 1997.
Zha et al. *Cell* 87:619–28, 1996.

What is claimed is:

1. An isolated polypeptide comprising amino acids 103–123 of SEQ ID NO:1, wherein:
   (a) serine-118 is replaced with alanine or glycine;
   (b) said polypeptide has at least 85% sequence identity with SEQ ID NO: 1; and
   (b) said polypeptide has in vitro cell death promoting activity.

2. The isolated polypeptide of claim 1, wherein said polypeptide has at least 90% sequence identity with SEQ ID NO:1.

3. The isolated polypeptide of claim 1, wherein said polypeptide has at least 95% sequence identity with SEQ ID NO:1.

4. The isolated polypeptide of any one of claims 1, 2, or 3, wherein said serine-118 is replaced with alanine.

5. The isolated polypeptide of any one of claims 1, 2, or 3, wherein said serine-118 is replaced with glycine.

6. An isolated polypeptide comprising amino acids 106–132 of SEQ ID NO:1, wherein:
   (a) serine-118 is replaced with alanine or glycine;
   (b) said polypeptide has at least 85% sequence identity with SEQ ID NO: 1; and
   (b) said polypeptide has in vitro cell death promoting activity.

7. The isolated polypeptide of claim 6, wherein said polypeptide has at least 90% sequence identity with SEQ ID NO:1.

8. The isolated polypeptide of claim 6, wherein said polypeptide has at least 95% sequence identity with SEQ ID NO:1.

9. The isolated polypeptide of any one of claims 6, 7 or 8, wherein said serine-118 is replaced with alanine.

10. The isolated polypeptide of any one of claims 6, 7 or 8, wherein said serine-118 is replaced with glycine.

11. An isolated polypeptide comprising SEQ ID NO:1, except that serine-118 is replaced with alanine or glycine.

12. The isolated polypeptide of claim 11, wherein serine-118 is replaced with alanine.

13. The isolated polypeptide of claim 11, wherein serine-118 is replaced with glycine.

14. An isolated polypeptide consisting of SEQ ID NO:1, except that serine-118 is replaced with alanine or glycine.

15. The isolated polypeptide of claim 14, wherein serine-118 is replaced with alanine.

16. The isolated polypeptide of claim 14, wherein serine-118 is replaced with glycine.

* * * * *

SEQUENCE LISTING

<160> NUMBER OF SEQ ID NOS: 20

<210> SEQ ID NO 1
<211> LENGTH: 168
<212> TYPE: PRT
<213> ORGANISM: Homo sapiens

<400> SEQUENCE: 1

Met Phe Gln Ile Pro Glu Phe Glu Pro Ser Glu Gln Glu Asp Ser Ser
 1               5                  10                  15

Ser Ala Glu Arg Gly Leu Gly Pro Ser Pro Ala Gly Asp Gly Pro Ser
            20                  25                  30

```
Gly Ser Gly Lys His His Arg Gln Ala Pro Gly Leu Leu Trp Asp Ala
            35                  40                  45

Ser His Gln Gln Glu Gln Pro Thr Ser Ser His His Gly Gly Ala
 50                  55                  60

Gly Ala Val Glu Ile Arg Ser Arg His Ser Ser Tyr Pro Ala Gly Thr
 65                  70                  75                  80

Glu Asp Asp Glu Gly Met Gly Glu Glu Pro Ser Pro Phe Arg Gly Arg
                 85                  90                  95

Ser Arg Ser Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
            115                 120                 125

Leu Pro Arg Pro Lys Ser Ala Gly Thr Ala Thr Gln Met Arg Gln Ser
            130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165

<210> SEQ ID NO 2
<211> LENGTH: 204
<212> TYPE: PRT
<213> ORGANISM: Mus musculus

<400> SEQUENCE: 2

Met Gly Thr Pro Lys Gln Pro Ser Leu Ala Pro Ala His Ala Leu Gly
 1               5                  10                  15

Leu Arg Lys Ser Asp Pro Gly Ile Arg Ser Leu Gly Ser Asp Ala Gly
            20                  25                  30

Gly Arg Arg Trp Arg Pro Ala Ala Gln Ser Met Phe Gln Ile Pro Glu
            35                  40                  45

Phe Glu Pro Ser Glu Gln Glu Asp Ala Ser Ala Thr Asp Arg Gly Leu
 50                  55                  60

Gly Pro Ser Leu Thr Glu Asp Gln Pro Gly Pro Tyr Leu Ala Pro Gly
 65                  70                  75                  80

Leu Leu Gly Ser Asn Ile His Gln Gln Gly Arg Ala Ala Thr Asn Ser
                 85                  90                  95

His His Gly Gly Ala Gly Ala Met Glu Thr Arg Ser Arg His Ser Ser
            100                 105                 110

Tyr Pro Ala Gly Thr Glu Glu Asp Glu Gly Met Glu Glu Glu Leu Ser
            115                 120                 125

Pro Phe Arg Gly Arg Ser Arg Ser Ala Pro Pro Asn Leu Trp Ala Ala
            130                 135                 140

Gln Arg Tyr Gly Arg Glu Leu Arg Arg Met Ser Asp Glu Phe Glu Gly
145                 150                 155                 160

Ser Phe Lys Gly Leu Pro Arg Pro Lys Ser Ala Gly Thr Ala Thr Gln
                165                 170                 175

Met Arg Gln Ser Ala Gly Trp Thr Arg Ile Ile Gln Ser Trp Trp Asp
            180                 185                 190

Arg Asn Leu Gly Lys Gly Gly Ser Thr Pro Ser Gln
            195                 200

<210> SEQ ID NO 3
<211> LENGTH: 162
<212> TYPE: PRT
```

<213> ORGANISM: Mus musculus

<400> SEQUENCE: 3

```
Met Phe Gln Ile Pro Glu Phe Pro Ser Glu Gln Glu Asp Ala Ser
  1               5                  10                  15

Ala Thr Asp Arg Gly Leu Gly Pro Ser Leu Thr Glu Asp Gln Pro Gly
             20                  25                  30

Pro Tyr Leu Ala Pro Gly Leu Leu Gly Ser Asn Ile His Gln Gln Gly
         35                  40                  45

Arg Ala Ala Thr Asn Ser His His Gly Gly Ala Gly Ala Met Glu Thr
     50                  55                  60

Arg Ser Arg His Ser Ser Tyr Pro Ala Gly Thr Glu Asp Glu Gly
 65                  70                  75                  80

Met Glu Glu Leu Ser Pro Phe Arg Gly Arg Ser Arg Ser Ala Pro
                 85                  90                  95

Pro Asn Leu Trp Ala Ala Gln Arg Tyr Gly Arg Glu Leu Arg Arg Met
            100                 105                 110

Ser Asp Glu Phe Glu Gly Ser Phe Lys Gly Leu Pro Arg Pro Lys Ser
        115                 120                 125

Ala Gly Thr Ala Thr Gln Met Arg Gln Ser Ala Gly Trp Thr Arg Ile
    130                 135                 140

Ile Gln Ser Trp Trp Asp Arg Asn Leu Gly Lys Gly Gly Ser Thr Pro
145                 150                 155                 160

Ser Gln
```

<210> SEQ ID NO 4
<211> LENGTH: 26
<212> TYPE: PRT
<213> ORGANISM: Artificial Sequence
<220> FEATURE:
<223> OTHER INFORMATION: Description of Artificial Sequence: BAD BH3
      consensus sequence

<400> SEQUENCE: 4

```
Ala Ala Gln Arg Tyr Gly Arg Glu Leu Arg Arg Met Ser Asp Glu Phe
  1               5                  10                  15

Val Asp Ser Phe Lys Lys Gly Leu Pro Arg
             20                  25
```

<210> SEQ ID NO 5
<211> LENGTH: 26
<212> TYPE: PRT
<213> ORGANISM: Artificial Sequence
<220> FEATURE:
<223> OTHER INFORMATION: Description of Artificial Sequence: BAK BH3
      consensus sequence

<400> SEQUENCE: 5

```
Thr Met Gly Gln Val Gly Arg Gln Leu Ala Ile Ile Gly Asp Asp Ile
  1               5                  10                  15

Asn Arg Arg Tyr Asp Ser Glu Phe Gln Thr
             20                  25
```

<210> SEQ ID NO 6
<211> LENGTH: 26
<212> TYPE: PRT
<213> ORGANISM: Artificial Sequence
<220> FEATURE:
<223> OTHER INFORMATION: Description of Artificial Sequence: BAX BH3
      consensus sequence -continued

```
<400> SEQUENCE: 6

Ser Thr Lys Lys Leu Ser Glu Cys Leu Lys Arg Ile Gly Asp Glu Leu
  1               5                  10                  15

Asp Ser Asn Met Glu Leu Gln Arg Met Ile
             20                  25

<210> SEQ ID NO 7
<211> LENGTH: 26
<212> TYPE: PRT
<213> ORGANISM: Artificial Sequence
<220> FEATURE:
<223> OTHER INFORMATION: Description of Artificial Sequence: BIK BH3
      consensus sequence

<400> SEQUENCE: 7

Gly Ser Asp Ala Leu Ala Leu Arg Leu Ala Cys Ile Gly Asp Glu Met
  1               5                  10                  15

Asp Val Ser Leu Arg Ala Pro Arg Leu Ala
             20                  25

<210> SEQ ID NO 8
<211> LENGTH: 26
<212> TYPE: PRT
<213> ORGANISM: Artificial Sequence
<220> FEATURE:
<223> OTHER INFORMATION: Description of Artificial Sequence: BID BH3
      consensus sequence

<400> SEQUENCE: 8

Ile Ile Arg Asn Ile Ala Arg His Leu Ala Gln Val Gly Asp Ser Met
  1               5                  10                  15

Asp Arg Ser Ile Pro Pro Gly Leu Val Asn
             20                  25

<210> SEQ ID NO 9
<211> LENGTH: 26
<212> TYPE: PRT
<213> ORGANISM: Artificial Sequence
<220> FEATURE:
<223> OTHER INFORMATION: Description of Artificial Sequence: HRK BH3
      consensus sequence

<400> SEQUENCE: 9

Ala Ala Gln Leu Thr Ala Ala Arg Leu Lys Ala Leu Gly Asp Glu Leu
  1               5                  10                  15

His Gln Arg Thr Met Trp Arg Arg Arg Ala
             20                  25

<210> SEQ ID NO 10
<211> LENGTH: 26
<212> TYPE: PRT
<213> ORGANISM: Artificial Sequence
<220> FEATURE:
<223> OTHER INFORMATION: Description of Artificial Sequence: BOK BH3
      consensus sequence

<400> SEQUENCE: 10

Arg Leu Ala Glu Val Cys Thr Val Leu Leu Arg Leu Gly Asp Glu Leu
  1               5                  10                  15

Glu Gln Ile Arg Pro Ser Val Tyr Arg Asn
             20                  25

<210> SEQ ID NO 11
<211> LENGTH: 26
```

<212> TYPE: PRT
<213> ORGANISM: Artificial Sequence
<220> FEATURE:
<223> OTHER INFORMATION: Description of Artificial Sequence: BIM BH3
      consensus sequence

<400> SEQUENCE: 11

Pro Glu Ile Trp Ile Ala Gln Glu Leu Arg Arg Ile Gly Asp Glu Phe
 1               5                  10                  15

Asn Ala Tyr Tyr Ala Arg Arg Val Phe Leu
             20                  25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: BAD primer
      (murine)

<400> SEQUENCE: 12
gcctccagga tccaagatgg gaacc                                      25

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: BAD primer
      (murine)

<400> SEQUENCE: 13
ggagcgggta gaattccggg atg                                        23

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: BAD primer
      (murine short)

<400> SEQUENCE: 14
tggagaccag gatcccagag tagct                                      25

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Human PKI
      primer

<400> SEQUENCE: 15
ctatgtggat ccttggtagc aatg                                       24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Human PKI
      primer

<400> SEQUENCE: 16
cctcatagac cttaagtaaa caaa                                       24

```
<210> SEQ ID NO 17
<211> LENGTH: 18
<212> TYPE: PRT
<213> ORGANISM: Homo sapiens

<400> SEQUENCE: 17

Gln Arg Tyr Gly Arg Glu Leu Arg Arg Met Ser Asp Glu Ser Val Asp
 1               5                  10                  15

Ser Phe

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: antibody
      generating phosphopeptide

<400> SEQUENCE: 18

Gly Cys Gln Arg Tyr Gly Arg Glu Leu Arg Arg Met Ser Asp Glu Ser
 1               5                  10                  15

Val Asp Ser Phe
            20

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: ST-kinase
      recognition motif

<400> SEQUENCE: 19

Leu Arg Arg Met Ser Asp
 1               5

<210> SEQ ID NO 20
<211> LENGTH: 12
<212> TYPE: PRT
<213> ORGANISM: Human immunodeficiency virus
<220> FEATURE:
<223> OTHER INFORMATION: Description of Artificial Sequence: Tat
      polypeptide

<400> SEQUENCE: 20

Tyr Gly Arg Lys Lys Arg Arg Gln Arg Arg Arg Gly
 1               5                  10
```